(12) United States Patent
Hayoz et al.

(10) Patent No.: US 9,362,508 B2
(45) Date of Patent: Jun. 7, 2016

(54) DIKETOPYRROLOPYRROLE OLIGOMERS FOR USE IN ORGANIC SEMICONDUCTOR DEVICES

(75) Inventors: Pascal Hayoz, Hofstetten (CH); Natalia Chebotareva, Hagenthal le Bas (FR)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/123,975

(22) PCT Filed: Jun. 20, 2012

(86) PCT No.: PCT/EP2012/061777
§ 371 (c)(1),
(2), (4) Date: Dec. 5, 2013

(87) PCT Pub. No.: WO2012/175530
PCT Pub. Date: Dec. 27, 2012

(65) Prior Publication Data
US 2014/0128618 A1    May 8, 2014

Related U.S. Application Data

(60) Provisional application No. 61/499,700, filed on Jun. 22, 2011.

(30) Foreign Application Priority Data

Jun. 22, 2011   (EP) .................................... 11170877

(51) Int. Cl.
| | |
|---|---|
| C07D 519/00 | (2006.01) |
| C08G 61/12 | (2006.01) |
| H01L 51/00 | (2006.01) |
| H01B 1/12 | (2006.01) |
| C09B 69/10 | (2006.01) |
| B82Y 10/00 | (2011.01) |
| H01L 51/42 | (2006.01) |
| H01L 27/30 | (2006.01) |

(52) U.S. Cl.
CPC ............ *H01L 51/0074* (2013.01); *B82Y 10/00* (2013.01); *C07D 519/00* (2013.01); *C08G 61/12* (2013.01); *C08G 61/124* (2013.01); *C08G 61/125* (2013.01); *C08G 61/126* (2013.01); *C09B 69/101* (2013.01); *C09B 69/102* (2013.01); *C09B 69/109* (2013.01); *H01B 1/12* (2013.01); *H01B 1/127* (2013.01); *H01L 51/00* (2013.01); *H01L 51/0072* (2013.01); *C08G 2261/124* (2013.01); *C08G 2261/1412* (2013.01); *C08G 2261/226* (2013.01); *C08G 2261/3222* (2013.01); *C08G 2261/3223* (2013.01); *C08G 2261/3243* (2013.01); *C08G 2261/344* (2013.01); *C08G 2261/364* (2013.01); *C08G 2261/411* (2013.01); *C08G 2261/91* (2013.01); *C08G 2261/92* (2013.01); *C08G 2261/95* (2013.01); *H01L 27/302* (2013.01); *H01L 51/0047* (2013.01); *H01L 51/4253* (2013.01); *Y02E 10/549* (2013.01); *Y02P 70/521* (2015.11)

(58) Field of Classification Search
None
See application file for complete search history.

(56) References Cited

U.S. PATENT DOCUMENTS

| | | | | |
|---|---|---|---|---|
| 5,847,156 | A * | 12/1998 | Eldin | C07D 487/04 544/144 |
| 5,919,944 | A * | 7/1999 | Eldin | C07D 487/04 106/150.1 |
| 7,910,684 | B2 * | 3/2011 | Li | 528/163 |
| 7,932,344 | B2 | 4/2011 | Li | |
| 8,008,507 | B2 * | 8/2011 | Yamamoto | C09K 11/06 252/301.16 |
| 8,598,448 | B2 * | 12/2013 | Lu et al. | 136/263 |
| 8,598,450 | B2 * | 12/2013 | Pan et al. | 136/263 |
| 8,624,232 | B2 | 1/2014 | Sonar et al. | |

(Continued)

FOREIGN PATENT DOCUMENTS

| | | |
|---|---|---|
| EP | 2 033 983 A2 | 3/2009 |
| EP | 2033983 A2 * | 3/2009 |

(Continued)

OTHER PUBLICATIONS

Loser et al. JACS (2011) 133, 8142-8145.*

(Continued)

*Primary Examiner* — Nyeemah A Grazier
(74) *Attorney, Agent, or Firm* — Oblon, McClelland, Maier & Neustadt, L.L.P.

(57) ABSTRACT

The present invention relates to oligomers of the formula (I), and their use as organic semiconductor in organic devices, especially in organic photovoltaics (solar cells) and photodiodes, or in a device containing a diode and/or an organic field effect transistor. High efficiency of energy conversion, excellent field-effect mobility, good on/off current ratios and/ or excellent stability can be observed, when the oligomers according to the invention are used in organic field effect transistors, organic photovoltaics (solar cells) and photodiodes.

(I)

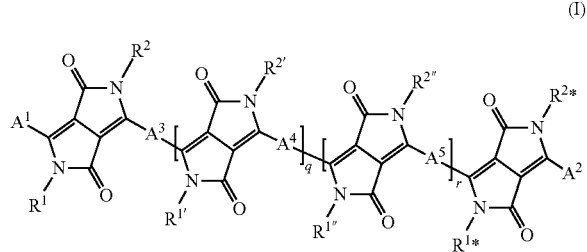

18 Claims, No Drawings

(56) References Cited

U.S. PATENT DOCUMENTS

| | | | | |
|---|---|---|---|---|
| 8,629,238 B2 * | 1/2014 | Dueggeli | ............ | C08G 61/124 528/377 |
| 8,796,469 B2 * | 8/2014 | Hayoz | ................ | C07D 487/04 257/40 |
| 8,912,305 B2 * | 12/2014 | Duggeli | ................ | C08G 61/12 257/40 |
| 8,975,359 B2 * | 3/2015 | Duggeli | ............ | C08G 61/124 257/40 |
| 2008/0217581 A1 * | 9/2008 | Yamamoto | ............ | C09K 11/06 252/301.16 |
| 2009/0065878 A1 * | 3/2009 | Li | ................ | 257/411 |
| 2011/0284826 A1 * | 11/2011 | Hayoz et al. | .................. | 257/40 |
| 2012/0142872 A1 | 6/2012 | Lamatsch et al. | | |
| 2013/0234075 A1 * | 9/2013 | Kim | .................... | C07D 519/00 252/510 |
| 2014/0217329 A1 * | 8/2014 | Hayoz | .................. | C09B 23/148 252/500 |
| 2015/0028142 A1 * | 1/2015 | Coray | .................... | B02C 17/22 241/300 |

FOREIGN PATENT DOCUMENTS

| | | |
|---|---|---|
| JP | 2006 310538 A | 11/2006 |
| WO | 2006/061343 A1 | 6/2006 |
| WO | 2010/136352 A1 | 12/2010 |
| WO | 2011/025454 A1 | 3/2011 |
| WO | WO 2011025454 A1 * | 3/2011 |

OTHER PUBLICATIONS

English Language abst. of JP2006310538 Nov. 9, 2006.
Li et al., Journal of Materials Chemistry, vol. 21, No. 29 (Jan. 1, 2011) pp. 10829-10831.
Woo et al., Journal of the American Chemical Society, vol. 132, No. 44 (Nov. 10, 2010) pp. 15547-15549.
Bijleveld et al., Journal of Materials Chemistry, The Royal Society of Chemistry, No. 21, Jan. 1, 2011 pp. 1600-1606.
The International Search Report dated Oct. 8, 2012.
The EP Search Report dated Dec. 30, 2011.
The Int. Prel. Report on Patentability dated Dec. 23, 2013.
U.S. Appl. No. 14/385,696, filed Sep. 16, 2014, Welker, et al.
U.S. Appl. No. 14/386,123, filed Sep. 18, 2014, Hayoz.

* cited by examiner

DIKETOPYRROLOPYRROLE OLIGOMERS FOR USE IN ORGANIC SEMICONDUCTOR DEVICES

The present invention relates to 1,4-diketopyrrolo[3,4-c] pyrrole (DPP) derivatives of formula I, to their manufacture; and to their use as organic semiconductors, e.g. in semiconductor devices, especially a sensor, a diode, a photodiode, an organic field effect transistor, a transistor for flexible displays, and/or a solar cell (photovoltaic cell).

Examples of DPP polymers and their synthesis are, for example, described in US6451459B1, WO05/049695, WO2008/000664, EP2034537A2, EP2075274A1, WO2010/049321, WO2010/049323, WO2010/108873, WO2010/115767, WO2010/136353, WO2010/136352 and WO2011/144566 (PCT/EP2011/057878).

Matthias Horn et al., Eur. Polymer J. 38 (2002) 2197-2205 describes the synthesis and characterisation of thermomesogenic polysiloxanes with 2,5-dihydropyrrolo[3,4-c]pyrrole units in the main chain.

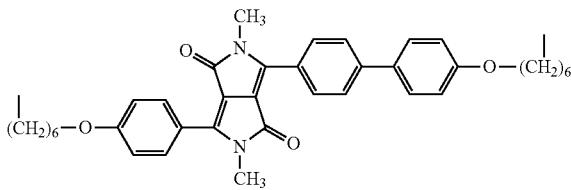

M. Smet et al., Tetrahedron Letters 42 (2001) 6257-6530 describes oligomers, which are prepared by a stepwise sequence of suzuki couplings using brominated 1,4-dioxo-3,6-diphenylpyrrolo[3,4c]pyrrole (DPP derivatives) and 1,4-dibromo-2,5-di-n-hexylbenzene as the monomers. The resulting oligomers contained three, five and seven DPP units, respectively.

WO2003048268 relates to an organic electroluminescent device comprising a perylene derivative and a diketopyrrolopyrrole derivative, such as, for example,

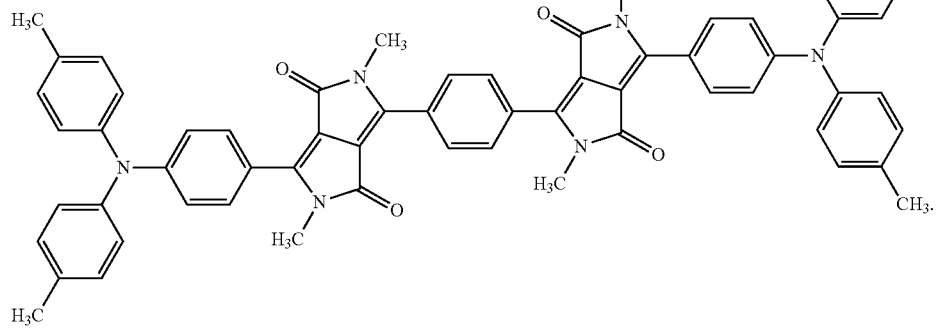

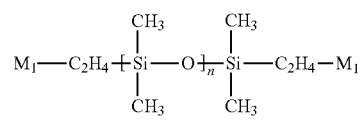

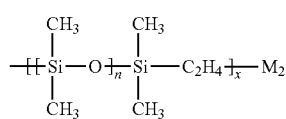

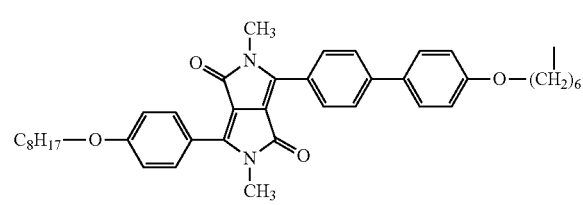

WO06/061343 discloses fluorescent diketopyrrolopyrroles of the formula

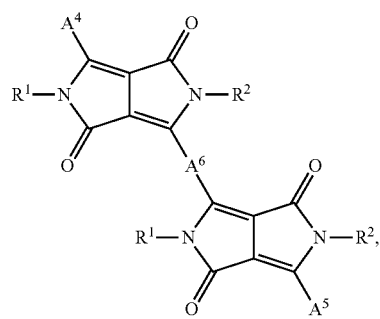

wherein $R^1$ and $R^2$ may be the same or different and are selected from a $C_1$-$C_{25}$alkyl group, an allyl group, which can be substituted one to three times with $C_1$-$C_3$alkyl, a cycloalkyl group, which can optionally be substituted one to three times with $C_1$-$C_8$alkyl and/or $C_1$-$C_8$alkoxy, a cycloalkyl group, which is condensed one or two times by phenyl which can be substituted one to three times with $C_1$-$C_4$-alkyl, halogen, nitro, or cyano, an alkenyl group, a cycloalkenyl group, an alkynyl group, a heterocyclic group, haloalkyl, haloalkenyl, haloalkynyl, a heterocyclic group, a ketone or aldehyde group, an ester group, a carbamoyl group, a silyl group, a siloxanyl group, aryl, heteroaryl, or —$CR^3R^4$—$(CH_2)_m$-$A^3$ wherein $R^3$ and $R^4$ independently from each other stand for hydrogen or $C_1$-$C_4$alkyl, or phenyl which can be substituted one to three times with $C_1$-$C_3$alkyl, $A^3$ stands for aryl, or heteroaryl, in particular phenyl or 1- or 2-naphthyl, which can be substituted one to three times with $C_1$-$C_8$alkyl and/or $C_1$-$C_8$alkoxy, and m stands for 0, 1, 2, 3 or 4, $A^4$ and $A^5$ independently of each other stands for

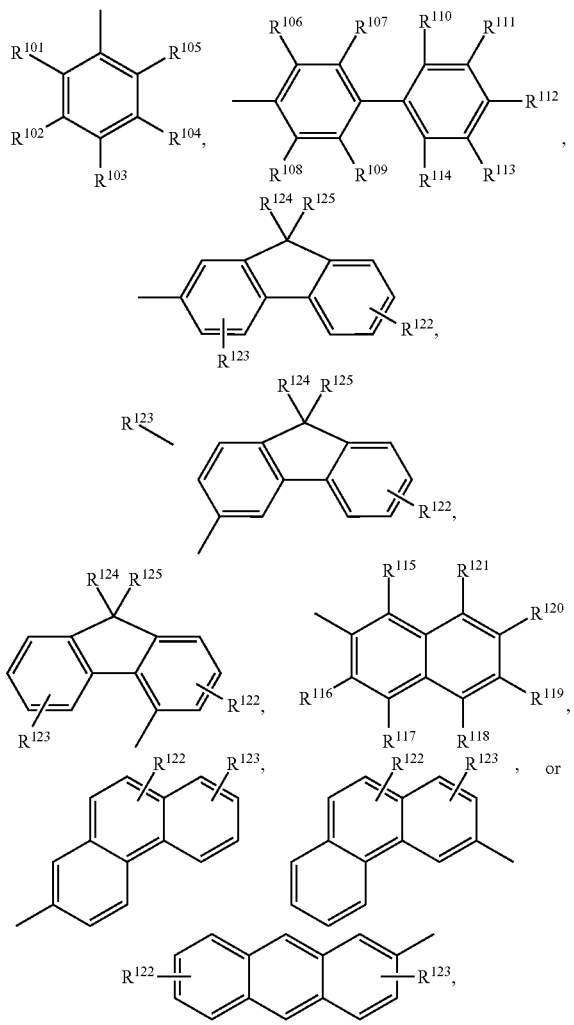

wherein $R^{101}$ to $R^{123}$ may be the same or different and are selected from hydrogen, $C_1$-$C_{25}$alkyl group, cycloalkyl, aralkyl, alkenyl, cycloalkenyl, alkynyl, hydroxyl, a mercapto group, alkoxy, alkylthio, an aryl ether group, an aryl thioether group, aryl, a heterocyclic group, halogen, haloalkyl, haloalkenyl, haloalkynyl, a cyano group, an aldehyde group, a carbonyl group, a carboxyl group, an ester group, a carbamoyl group, a group $NR^{27}R^{28}$, wherein $R^{27}$ and $R^{28}$ are as defined above, a nitro group, a silyl group, a siloxanyl group, a substituted or unsubstituted vinyl group, or at least two adjacent substituents $R^{115}$ to $R^{121}$ form an aromatic, heteroaromatic or aliphatic fused ring system, $R^{124}$ and $R^{125}$ may be the same or different and are selected from $C_1$-$C_{18}$alkyl; $C_1$-$C_{18}$alkoxy, $A^3$, $C_6$-$C_{18}$aryl; $C_7$-$C_{18}$aralkyl; or $R^{124}$ and $R^{125}$ together form a ring especially a five-, six- or seven-membered ring, which can optionally be substituted by $C_1$-$C_8$alkyl, or which can optionally be condensed one or two times by phenyl which can be substituted one to three times with $C_1$-$C_8$-alkyl, $C_1$-$C_8$-alkoxy, halogen and cyano; or a heteroaromatic group, especially

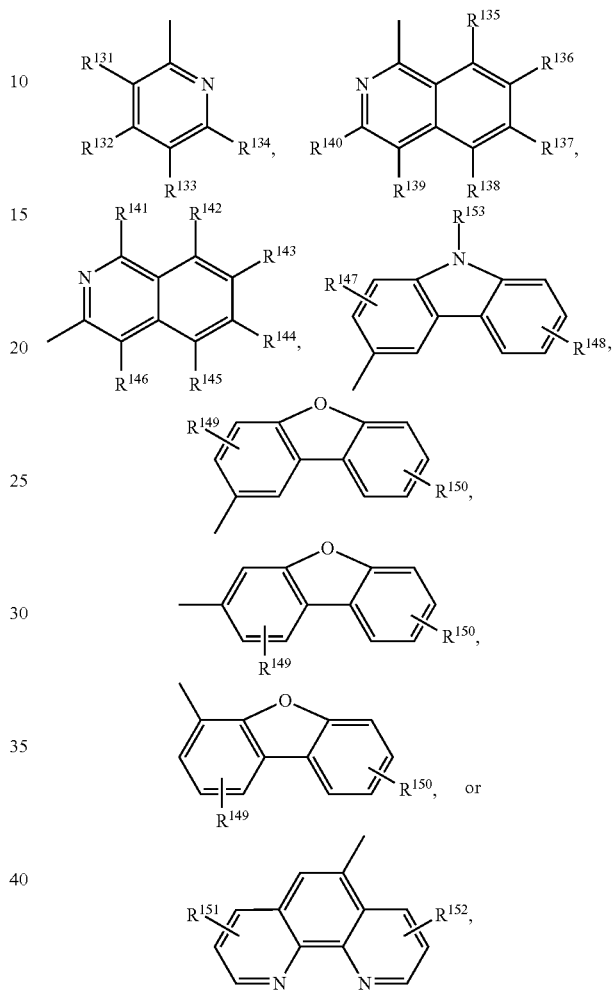

wherein $R^{131}$ to $R^{152}$ may be the same or different and are selected from hydrogen, $C_1$-$C_{25}$alkyl group, cycloalkyl, aralkyl, alkenyl, cycloalkenyl, alkynyl, hydroxyl, a mercapto group, alkoxy, alkylthio, an aryl ether group, an aryl thioether group, aryl, a heterocyclic group, halogen, haloalkyl, haloalkenyl, haloalkynyl, a cyano group, an aldehyde group, a carbonyl group, a carboxyl group, an ester group, a carbamoyl group, a group $NR^{27}R^{28}$, wherein $R^{27}$ and $R^{28}$ are as defined above, a nitro group, a silyl group, a siloxanyl group, a substituted or unsubstituted vinyl group, $R^{153}$ is a hydrogen atom, a $C_1$-$C_{25}$alkyl group, which might be interrupted by —O—, a cycloalkyl group, an aralkyl group, an aryl group, or a heterocyclic group, and $A^6$ is cycloalkyl, arylene, or heteroarylene, which are optionally substituted one to three times with $C_1$-$C_8$-alkyl, or $C_1$-$C_8$-alkoxy; and their use for the preparation of inks, colorants, pigmented plastics for coatings, non-impact-printing material, color filters, cosmetics, polymeric ink particles, toners, as fluorescent tracers, in color changing media, in solid dye lasers, EL lasers and electroluminescent devices.

The following compounds are explicitly mentioned in WO06/061343:

| Cpd. | $A^4 = A^5$ | $A^6$ | $R^1 = R^2$ |
|---|---|---|---|
| D-1 | 1-naphthyl | 1,4-phenylene | CH₃ |
| D-2 | 1-naphthyl | 1,4-naphthylene | CH₃ |
| D-3 | 1-naphthyl | 1,4-naphthylene | CH₃ |
| D-4 | 1-naphthyl | 1,3-phenylene (methyl) | CH₃ |
| D-5 | 1-naphthyl | 3,5-di-tert-butylphenyl | CH₃ |
| D-6 | 1-naphthyl | (phenylene)₂ | CH₃ |
| D-7 | 1-naphthyl | (phenylene)₃ | CH₃ |

JP2006310538 discloses fluorescent diketopyrrolopyrroles of the formula

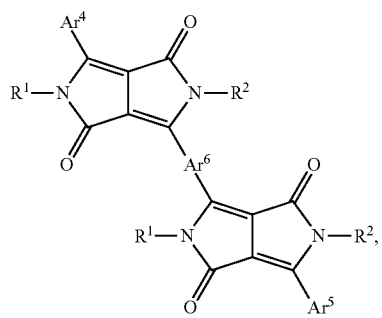

wherein $Ar^6$ may be aryl, or heteroryl, and its use in light emitting elements.

WO2007/003520 relates to fluorescent compounds, such as, for example,

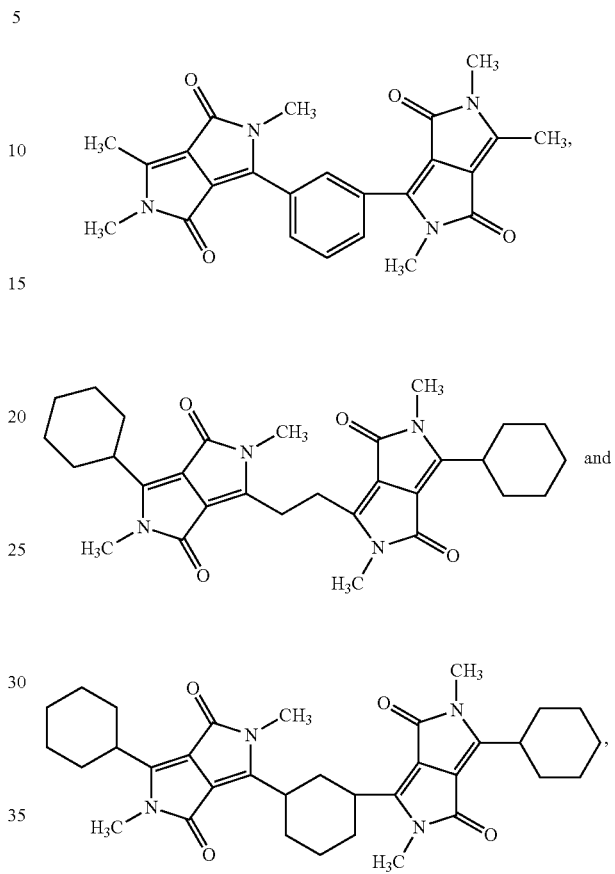

a process for their prepn. and their use for the prepn. of inks, colorants, pigmented plastics for coatings, non-impact-printing material, color12 filters, cosmetics, polymeric ink particles, toners, as fluorescent tracers, in color changing media, dye lasers and electroluminescent devices.

US2010/0326525 relates to optoelectronic devices, such as photovoltaic devices, comprising:
a) a first hole-collecting electrode;
b) an optional hole-transporting layer;
c) a layer comprising a mixture of an electron donor material and an electron acceptor material; and
d) a second electron-collecting electrode,
wherein the electron donor material comprises a compound of Formula (I):

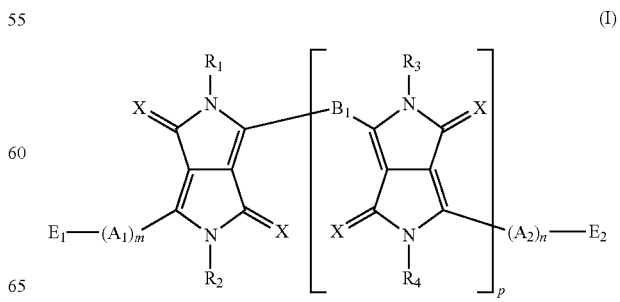

wherein X is oxygen or sulfur;

$A_1$ and $A_2$ are independently selected from substituted and unsubstituted aryl or heteroaryl groups, wherein each individual $A_1$ within the $(A_1)m$ moiety can be independently selected from a substituted or unsubstituted aryl or heteroaryl group, and each individual $A_2$ within the $(A_2)n$ moiety can be independently selected from a substituted or unsubstituted aryl or heteroaryl group;

$B_1$ is independently selected from substituted and unsubstituted aryl or heteroaryl groups;

m is independently selected from 1, 2, 3, 4, 5, 6, 7, 8, or 9;

n is independently selected from 1, 2, 3, 4, 5, 6, 7, 8, or 9;

p is independently selected from 0 or 1;

$E_1$ and $E_2$ are independently selected from a nonentity, H, or a substituted or unsubstituted aryl or heteroaryl group or a $C_1$-$C_{12}$ alkyl group; and $R_1$, $R_2$, $R_3$, and $R_4$ are independently selected from H, $C_1$-$C_{12}$ alkyl, and —C(=O)—O—$C_1$-$C_{12}$ alkyl.

The following dimeric DPP compound is explicitly disclosed:

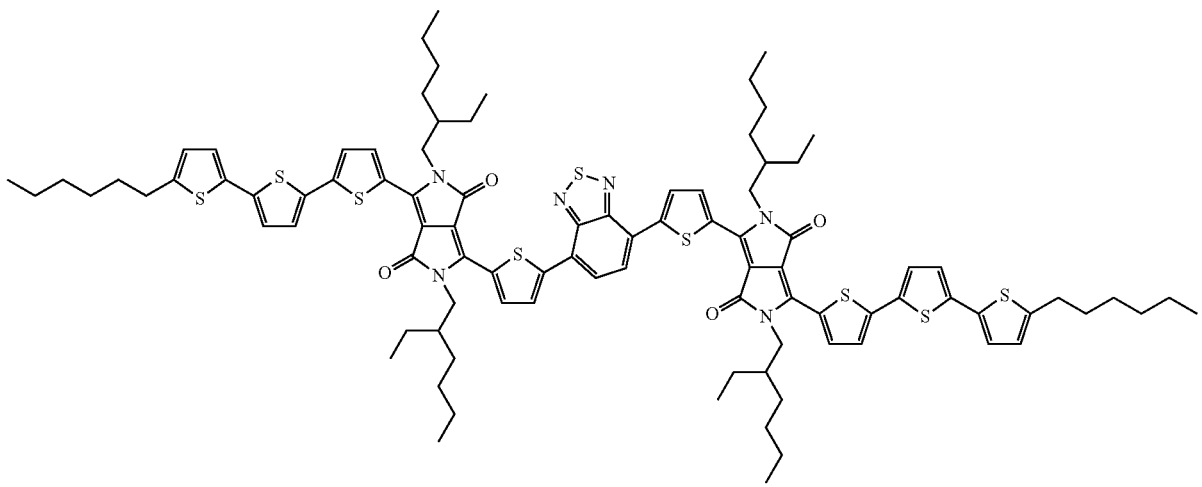 [SMILES: CCCCCCc1ccc(-c2ccc(-c3ccc(C4=C5C(=O)N(CC(CC)CCCC)C(c6ccc(-c7ccc(-c8ccc(C9=C%10C(=O)N(CC(CC)CCCC)C(c%11ccc(-c%12ccc(-c%13ccc(CCCCCC)s%13)s%12)s%11)=C%10C(=O)N9CC(CC)CCCC)s8)c8nsnc78)s6)=C5C(=O)N4CC(CC)CCCC)s3)s2)s1]

Y. Xu et al., Synthetic Metals 160 (2010) 2135-2142 reports the synthesis of DPP-containing oligomers:

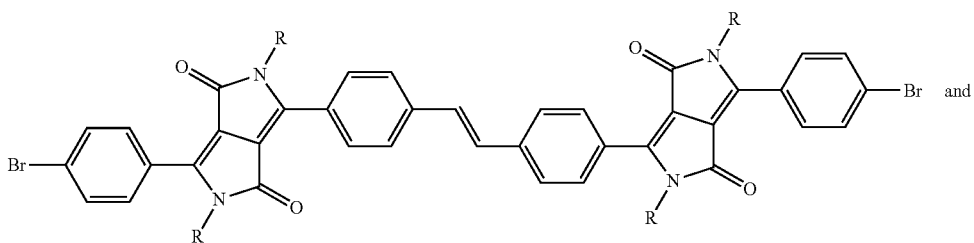

and

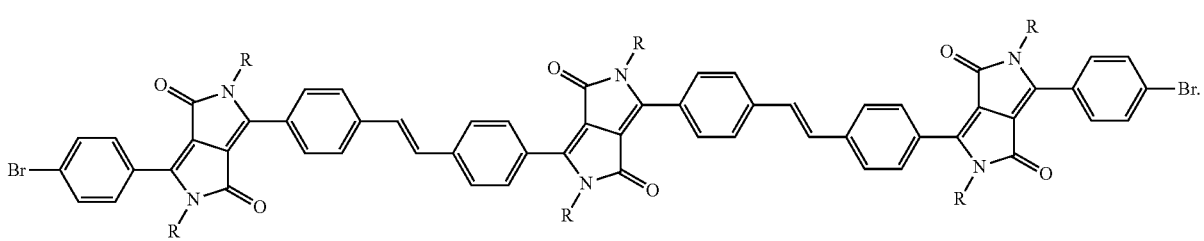

The monomers were copolymerized with benzothiadiazole, dioctyloxybenzene and fluorene through fluoride-mediated Suzuki polymerization to give copolymers with low content of DPP (1 mol %). The copolymers were used as the emitting layers in the light-emitting diodes.

R. A. J. Janssen et al., Macromol. Chem. Phys. 2011, 212, 515-520 disclose diketopyrrolopyrrole-based oligomers of formula

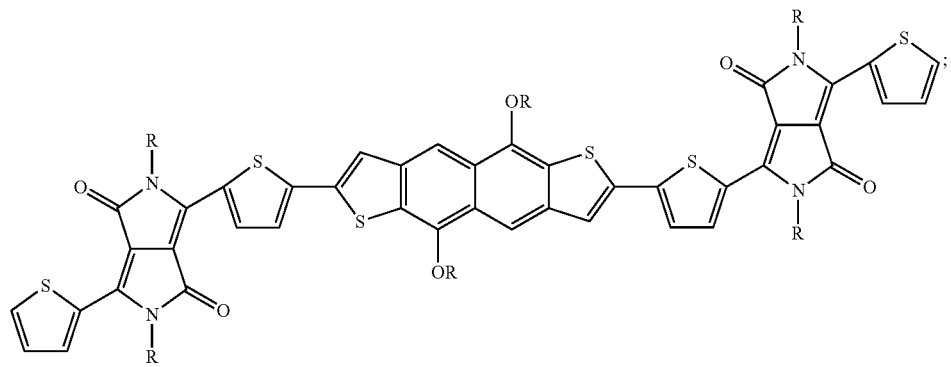

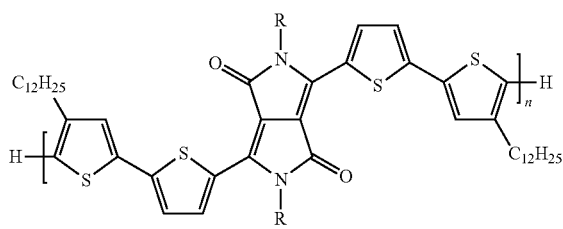

(R=2-hexyldecyl; n=1 to 4), which were prepared nickel (0)-mediated Yamamoto coupling reaction of a mixture of mono- and dibrominated monomers

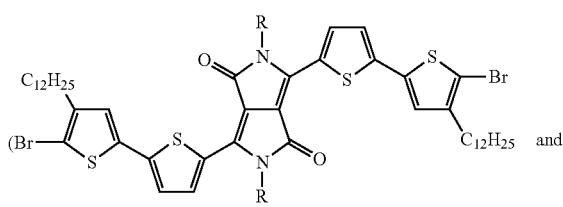

and

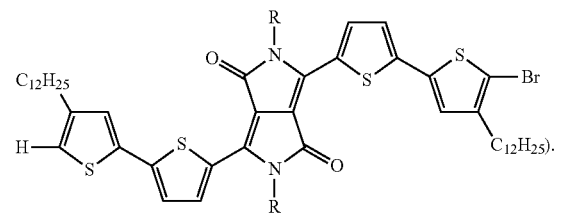

Monodisperse oligomers were obtained from the resulting mixture by separation of the oligomers using recycling GPC. Their optical and electrochemical properties were investigated. For all properties, measured in solution, no clear change was observed upon increase of the chain length, leading to the conclusion that conjugation in this system is only very limited.

Stephen Loser et al., J. Am. Chem. Soc., DOI: 10.1021/ja202791n•Publication Date (Web): 5 May 2011 describes the synthesis, characterization, and first implementation of a naphtho[2,3-b:6,7-b']dithiophene (NDT)-based donor molecule in highly efficient organic photovoltaics (OPVs). When NDT(TDPP)$_2$ (TDPP=thiophene-capped diketopyrrolopyrrole:

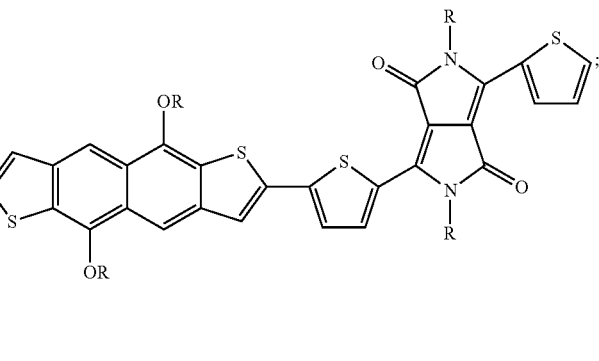

R=2-ethylhexyl)) is combined with the electron acceptor PC61BM, a power conversion efficiency (PCE) of 4.06±0.06% is achieved.

Yuning Li et al., J. Mater. Chem. 21 (2011) 10829 [published on web: 9 Jun. 2011] discloses the synthesis of the following polymer

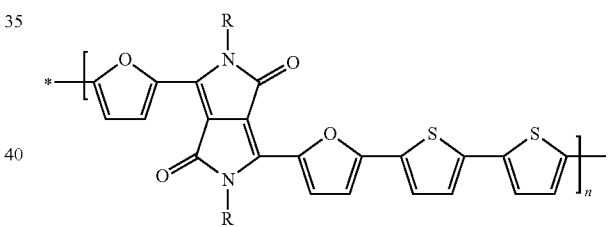

(R=2-octyldodecyl) and its use in OFETs.

C. H. Woo et al., J. Am. Chem. Soc. 132 (2010) 15547 [published on web: 14 Oct. 2010] discloses the synthesis of the following polymers

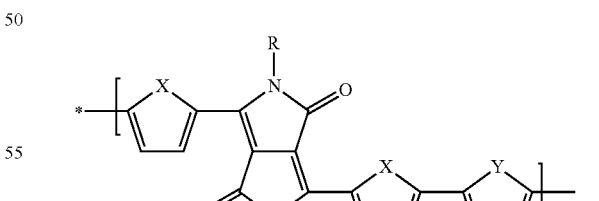

R=2-ethylhexyl,
X=S, Y=S; X=O, Y=S; or X=O, Y=O; and its use in solar cells.

R. A. J. Janssen et al., J. Mater. Chem. 21 (2011) 1600 [published on web: 6 Dec. 2010] discloses the synthesis of the following polymers

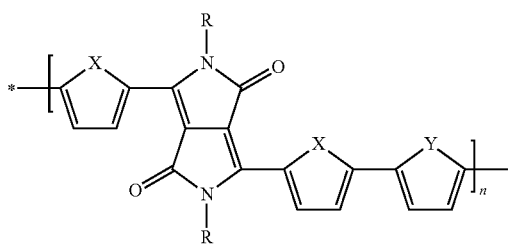

R=2-hexyldecyl, X=O, Y=S; X=O, Y=O; or X=S, Y=O; and its use in OFETs and solar cells.

EP2033983A2 is directed to DPP polymers having a structure represented by:

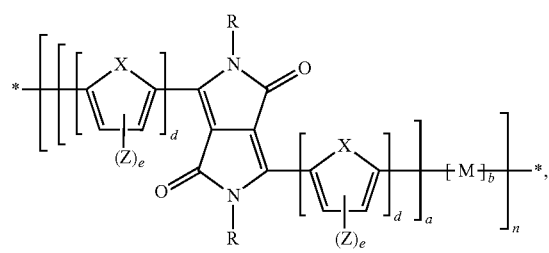
(IV)

wherein each X is independently selected from S, Se, O, and NR", each R" is independently selected from hydrogen, an optionally substituted hydrocarbon, and a hetero-containing group, each Z is independently one of an optionally substituted hydrocarbon, a hetero-containing group, and a halogen, d is a number which is at least 1, e is a number from zero to 2; a represents a number that is at least 1; b represents a number from 0 to 20; each M is an optional, conjugated moiety and n represents a number that is at least 1.

Among others the following polymers are disclosed:

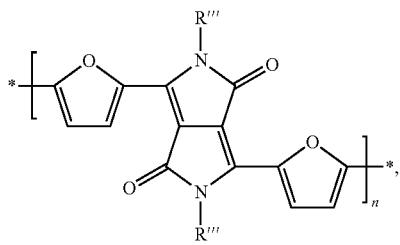
(22)

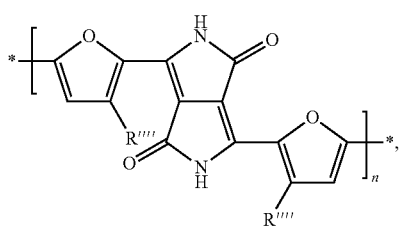
(23)

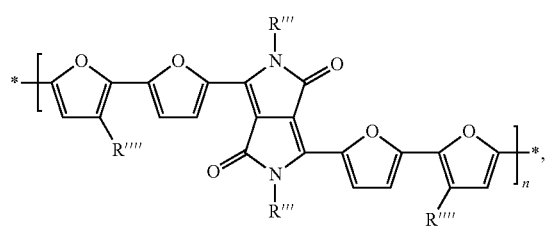
(24)

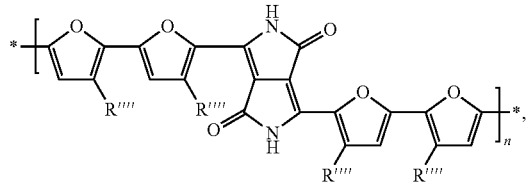
(25)

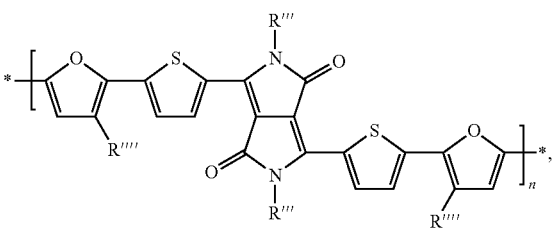
(44)

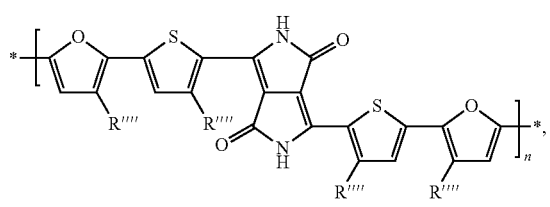
(45)

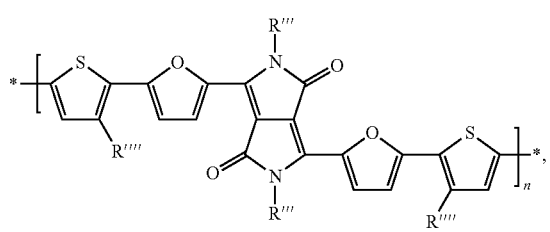
(46)

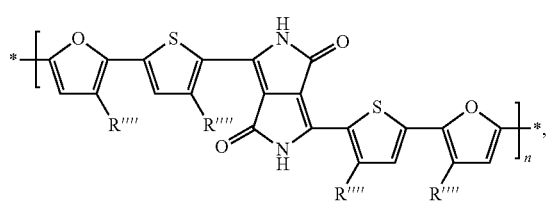
(47)

wherein n is the number of repeat units and can be from about 2 to about 5000, R''', R'''' and R''''' can be the same or different substituent, and wherein the substituent is independently selected from the group consisting of an optionally substituted hydrocarbon group and a heteroatom-containing group. For n is 2 no end group is defined.

WO2011025454A1 discloses compounds of formula

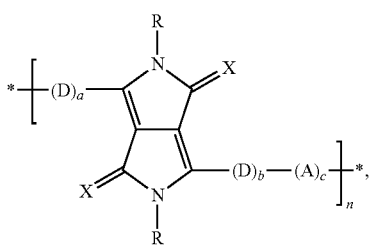

and its use in electronic devices. X is O, S or Se. D can be among others

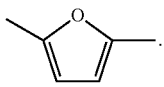

Among others the following polymers are disclosed:

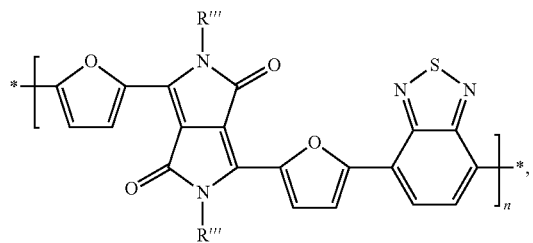

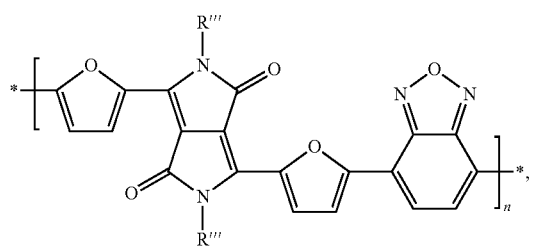

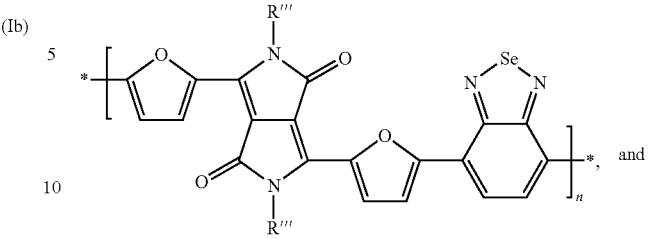

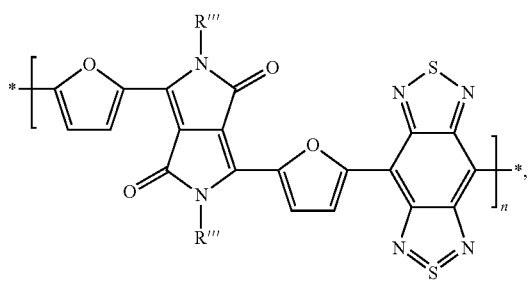

wherein n is 2 to 15000. For n is 2 no end group is defined.

It is the object of the present invention to provide compounds, which show high efficiency of energy conversion, excellent field-effect mobility, good on/off current ratios and/or excellent stability, when used in organic field effect transistors, organic photovoltaics (solar cells) and photodiodes.

It has surprisingly been found that certain dimeric, trimeric and quatermeric diketo-pyrrolopyrrol derivatives can be used as organic semiconductors. Said derivatives have excellent solubility in non-halogenated organic solvents (allowing easy handling). They can be synthesized easier than polymers (allowing cost savings), and they are easy to purify (allowing very pure products to be obtained at low cost).

Accordingly, the present invention relates to compounds of the formula

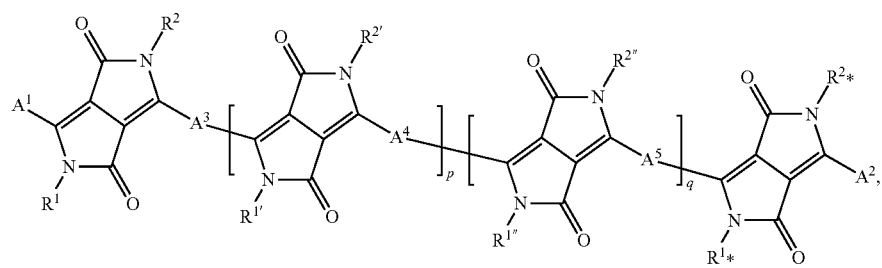

wherein
p is 0, or 1, q is 0, or 1,
$A^1$ and $A^2$ are independently of each other a group of formula

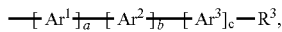

$A^3$, $A^4$ and $A^5$ are independently of each other a group of formula

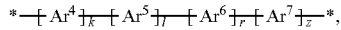

a is 1 or 2; b is 0, 1 or 2; c is 0, 1 or 2;
k is 0, 1, or 2; l is 1, 2, or 3; r is 0, or 1; z is 0, 1 or 2;
$R^1$, $R^2$, $R^{1'}$, $R^{2'}$, $R^{1''}$, $R^{2''}$, $R^{1*}$ and $R^{2*}$ may be the same or different and are selected from hydrogen, a $C_1$-$C_{100}$alkyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group or a siloxanyl group and/or can optionally be interrupted by —O—, —S—, —$NR^{39}$—, —COO—, —CO— or —OCO—,
a $C_2$-$C_{100}$ alkenyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group or a siloxanyl group and/or can optionally be interrupted by —O—, —S—, —$NR^{39}$—, —COO—, —CO— or —OCO—,
a $C_3$-$C_{100}$alkinyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group or a siloxanyl group and/or can optionally be interrupted by —O—, —S—, —$NR^{39}$—, —COO—, —CO— or —OCO—,
a $C_3$-$C_{12}$cycloalkyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group or a siloxanyl group and/or can optionally be interrupted by —O—, —S—, —$NR^{39}$—, —COO—, —CO— or —OCO—,
a $C_6$-$C_{24}$aryl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group or a siloxanyl group,
a $C_2$-$C_{20}$heteroaryl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group or a siloxanyl group,
—CO—$C_1$-$C_{18}$alkyl, —CO—$C_5$-$C_{12}$cycloalkyl, —COO—$C_1$-$C_{18}$alkyl;
$R^3$ is hydrogen, halogen, cyano, $C_1$-$C_{25}$alkyl, $C_1$-$C_{25}$alkyl which is substituted one or more times by E and/or interrupted one or more times by D,

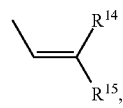

COO—$C_1$-$C_{18}$alkyl, a $C_4$-$C_{18}$cycloalkyl group, a $C_4$-$C_{18}$cycloalkyl group, which is substituted by G, $C_2$-$C_{18}$alkenyl, $C_2$-$C_{18}$alkynyl, $C_1$-$C_{18}$thioalkoxy, $C_1$-$C_{18}$alkoxy, $C_1$-$C_{18}$alkoxy which is substituted by E and/or interrupted by D, $C_7$-$C_{25}$aralkyl, or $C_7$-$C_{25}$aralkyl, which is substituted by G, or a

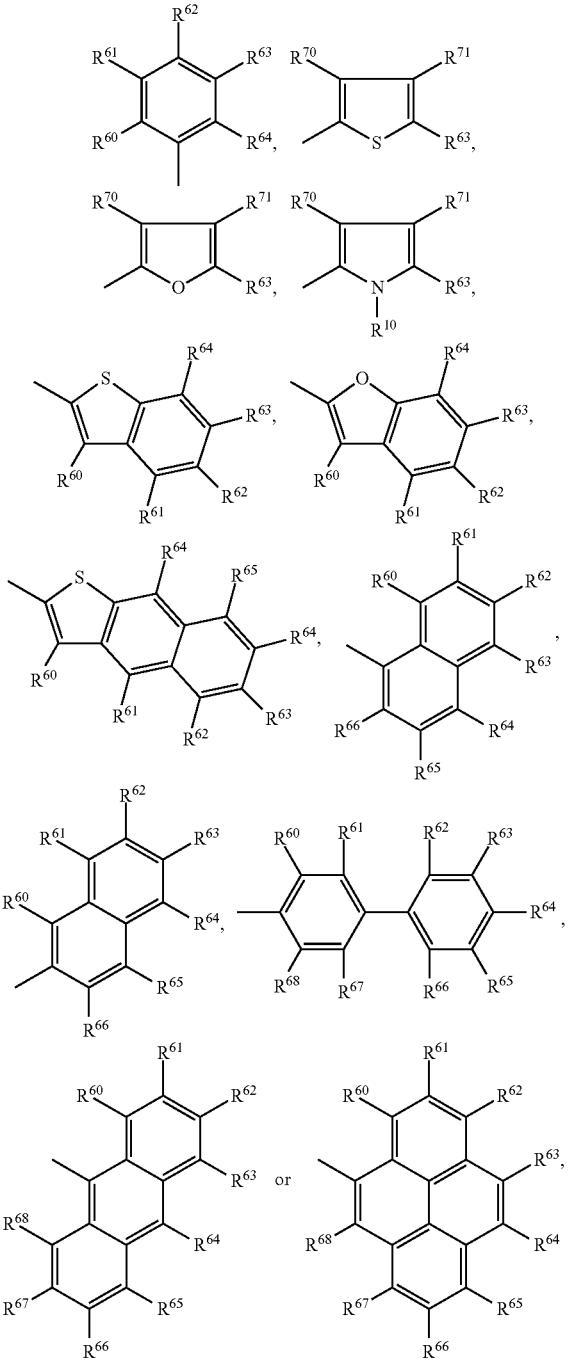

$Ar^1$, $Ar^2$, $Ar^3$, $Ar^4$, $Ar^5$, $Ar^6$ and $Ar^7$ are independently of each other a bivalent group of formula

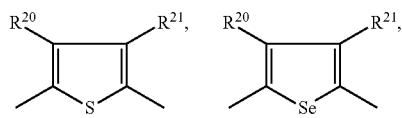

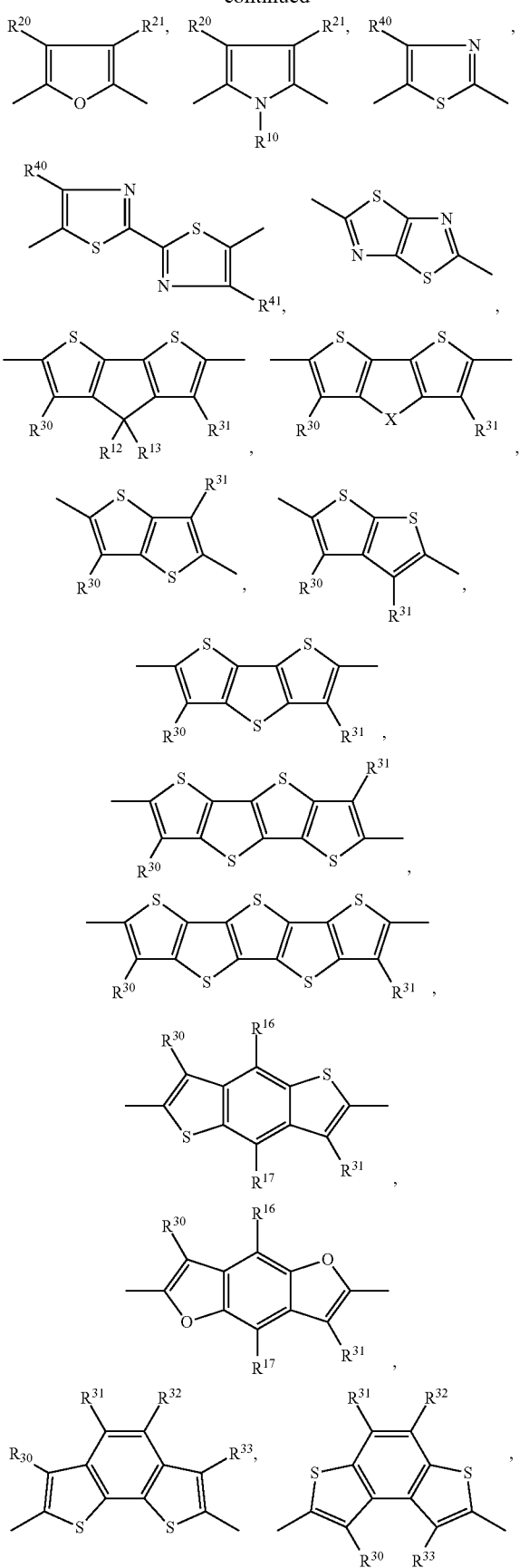
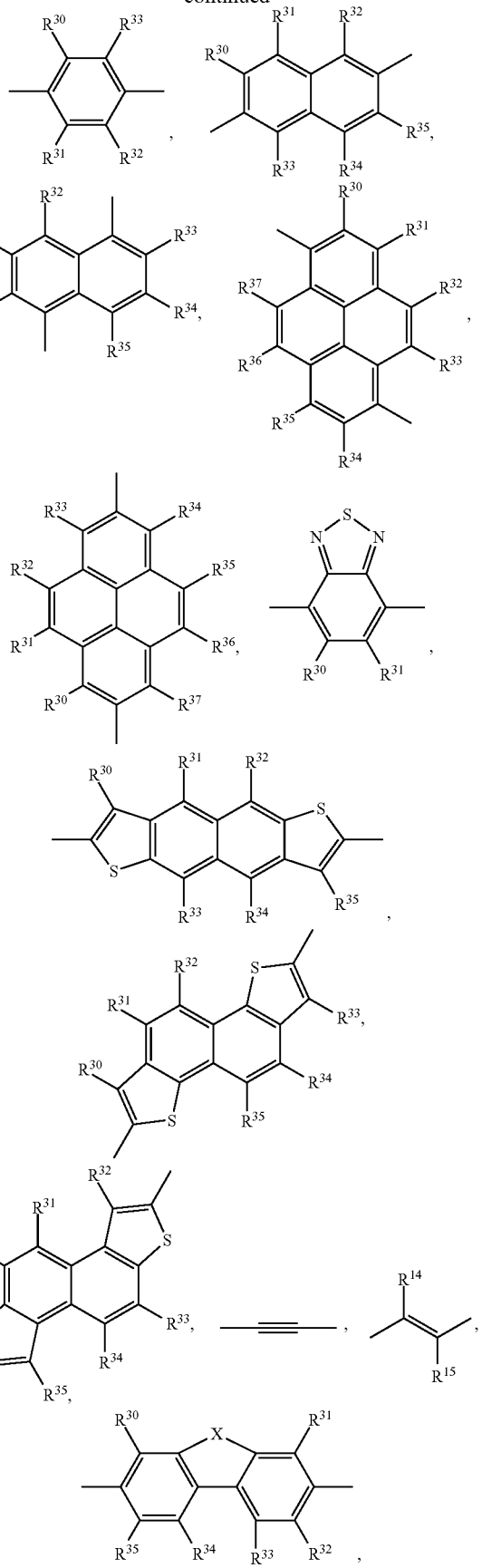

-continued

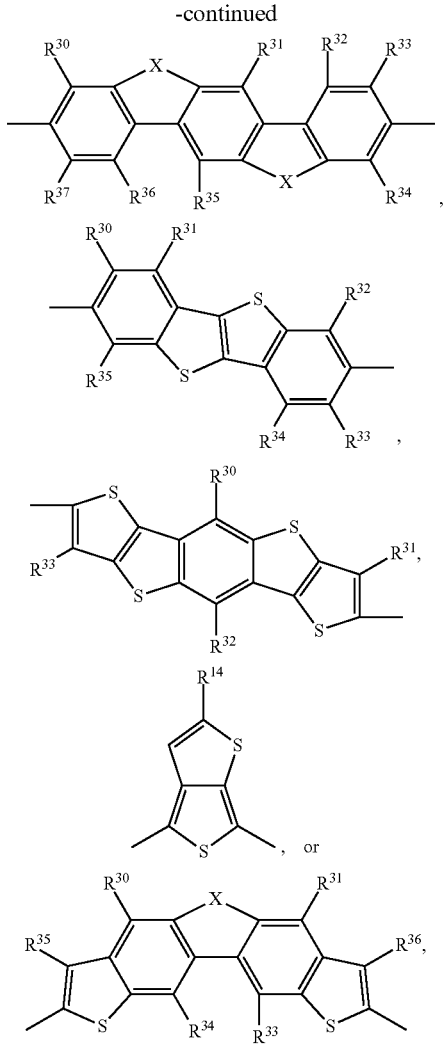

X is —O—, —S—, —NR$^{10}$—, —Si(R$^{18}$)(R$^{19}$)—, —Ge(R$^{18}$)(R$^{19}$)—, —C(R$^{12}$)(R$^{13}$)—, —C(=O)—, —C(=CR$^{14}$R$^{15}$)—,

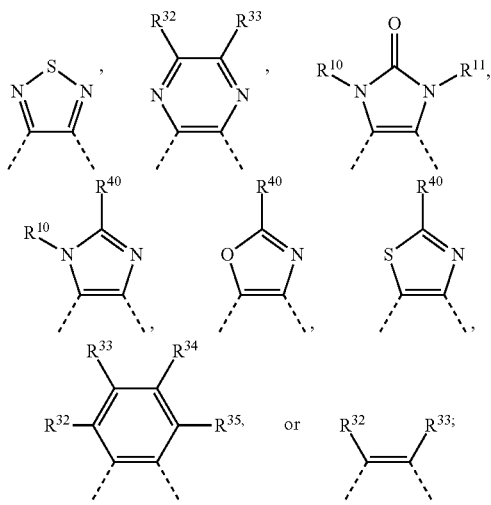

R$^{10}$ and R$^{11}$ are independently of each other hydrogen, C$_1$-C$_{18}$alkyl, C$_1$-C$_{18}$haloalkyl, C$_7$-C$_{25}$arylalkyl, or C$_1$-C$_{18}$alkanoyl, R$^{12}$ and R$^{13}$ are independently of each other hydrogen, C$_1$-C$_{18}$alkyl, C$_1$-C$_{18}$haloalkyl, C$_7$-C$_{25}$arylalkyl, C$_6$-C$_{24}$aryl, or 2-C$_{20}$heteroaryl, or R$^{12}$ and R$^{13}$ together represent oxo,

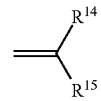

or form a five or six membered ring, which is unsubstituted or substituted by C$_1$-C$_{18}$alkyl and/or C$_1$-C$_{18}$alkoxy;

R$^{14}$ and R$^{15}$ are independently of each other hydrogen, C$_1$-C$_{18}$alkyl, C$_6$-C$_{24}$aryl, C$_2$-C$_{20}$heteroaryl, —CN or COOR$^{50}$;

R$^{16}$ and R$^{17}$ are independently of each other hydrogen, halogen, C$_1$-C$_{25}$alkyl, C$_1$-C$_{25}$alkoxy, C$_7$-C$_{25}$arylalkyl, or

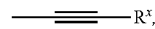

R$^x$ is a C$_1$-C$_{12}$alkyl group, or a tri(C$_1$-C$_8$alkyl)silyl group,

R$^{18}$ and R$^{19}$ are independently of each other hydrogen, C$_1$-C$_{18}$alkyl, C$_7$-C$_{25}$arylalkyl, or a phenyl group, which optionally can be substituted one to three times with C$_1$-C$_8$alkyl and/or C$_1$-C$_8$alkoxy, R$^{20}$ and R$^{21}$ are independently of each other hydrogen, C$_1$-C$_{25}$alkyl, C$_2$-C$_{25}$alkenyl, C$_2$-C$_{25}$alkyl which is interrupted by one or more —O— or —S—, COOR$^{50}$, cyano, C$_1$-C$_{18}$ alkoxy, C$_6$-C$_{24}$aryl, C$_7$-C$_{25}$arylalkyl, halogen or C$_2$-C$_{20}$heteroaryl, or R$^{20}$ and R$^{21}$ together represent alkylene or alkenylene which may be both bonded via oxygen and/or sulfur to the (hetero)aromatic residue and which may both have up to 4 carbon atoms, R$^{30}$ to R$^{37}$ are independently of each other hydrogen, C$_1$-C$_{25}$alkyl, C$_2$-C$_{25}$alkenyl, C$_2$-C$_{25}$alkyl which is interrupted by one or more —O— or —S—, COOR$^{50}$, cyano, C$_1$-C$_{25}$alkoxy, C$_6$-C$_{24}$aryl, C$_7$-C$_{25}$arylalkyl, halogen or C$_2$-C$_{20}$heteroaryl, R$^{40}$ and R$^{41}$ are independently of each other hydrogen, C$_1$-C$_{25}$alkyl, C$_2$-C$_{25}$alkenyl, C$_2$-C$_{25}$alkyl which is interrupted by one or more —O— or —S—, COOR$^{50}$, cyano, C$_1$-C$_{18}$alkoxy, C$_6$-C$_{24}$aryl, C$_7$-C$_{25}$arylalkyl, halogen or C$_2$-C$_{20}$heteroaryl, R$^{50}$ is C$_1$-C$_{25}$alkyl, C$_1$-C$_{25}$haloalkyl, C$_7$-C$_{25}$arylalkyl, C$_6$-C$_{24}$aryl or C$_2$-C$_{20}$heteroaryl;

R$^{60}$ to R$^{68}$ represent independently of each other H, halogen, cyano, C$_1$-C$_{25}$alkyl, C$_1$-C$_{25}$alkyl which is substituted by E and/or interrupted by D, C$_6$-C$_{24}$aryl, C$_6$-C$_{24}$aryl which is substituted by G, C$_2$-C$_{20}$heteroaryl, C$_2$-C$_{20}$heteroaryl which is substituted by G, a C$_4$-C$_{18}$cycloalkyl group, a C$_4$-C$_{18}$cycloalkyl group, which is substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, C$_7$-C$_{25}$aralkyl, or C$_7$-C$_{25}$aralkyl, which is substituted by G, R$^{70}$ and R$^{71}$ are independently of each other hydrogen, C$_1$-C$_{25}$alkyl, or C$_7$-C$_{25}$aralkyl, or R$^{70}$ and R$^{71}$ together represent alkylene or alkenylene which may be both bonded via oxygen and/or sulfur to the thienyl residue and which may both have up to 25 carbon atoms, D is —CO—, —COO—, —S—, —O—, —NR$^{39}$—, or —C(=O)NR$^{39}$—, E is $C_1$-$C_8$thioalkoxy, COO—$C_1$-$C_{18}$alkyl, $C_1$-$C_8$alkoxy, CN, —$NR^{39}R^{39'}$, —$CONR^{39}R^{39'}$, or halogen, G is E, or $C_1$-$C_{18}$alkyl, $R^{39}$ and $R^{39'}$ are independently of each other hydrogen, $C_1$-$C_{18}$alkyl, $C_1$-$C_{18}$haloalkyl, $C_7$-$C_{25}$arylalkyl, or $C_1$-$C_{18}$alkanoyl, with the proviso that at least one of the groups $Ar^1$, $Ar^2$, $Ar^3$, $Ar^4$, $Ar^5$, $Ar^6$ and $Ar^7$ is a group of formula:

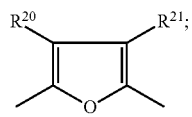

and the further proviso that $Ar^5$ is different from a group

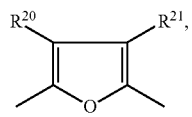

if q is 0, p is 0, k is 0, r is 0, z is 0 and l is 1.

The molecules of formula (I) consist preferably of a mirror-symmetrical sequence of building blocks selected from $Ar^1$ to $Ar^7$ and the diketopyrrolopyrrole basic skeletons.

The compound of formula I is preferably a compound of formula

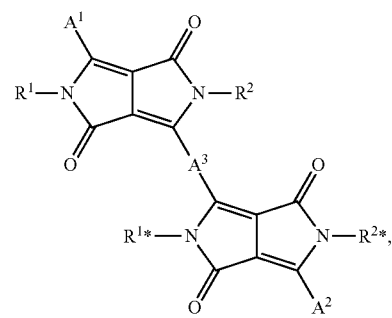

(Ia)

(Ib)

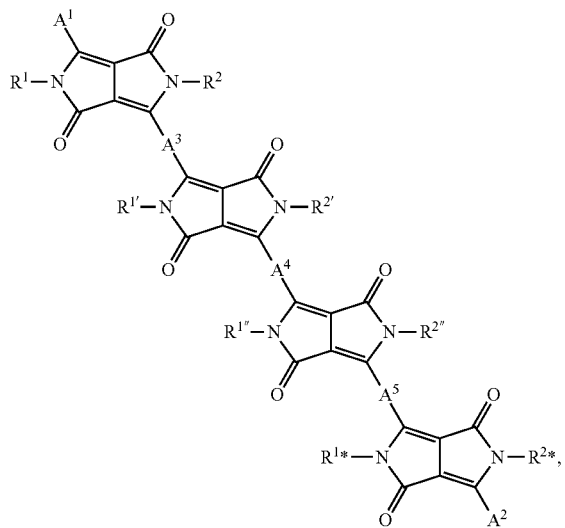

(Ic)

wherein $A^1$, $A^2$, $A^3$, $A^4$, $A^5$, $R^1$, $R^2$, $R^{1'}$, $R^{2'}$, $R^{1''}$, $R^{2''}$, $R^{1*}$ and $R^{2*}$ are as defined above.

At least one $Ar^1$, $Ar^2$, $Ar^3$, $Ar^4$, $Ar^5$, $Ar^6$ and $Ar^7$ is a group

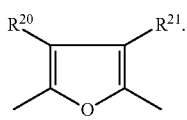

Preferably at least one of $Ar^1$, $Ar^4$ and $Ar^7$ is a group.

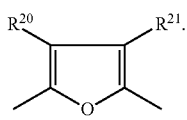

More preferably $Ar^1$ is

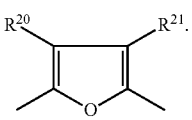

Most preferably $Ar^1$, $Ar^4$ and $Ar^7$ are a group

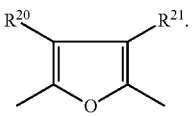

If $Ar^1$, $Ar^4$ or $Ar^7$ is a furan ring, the furan ring is preferably mono-substituted (position away from the DPP)

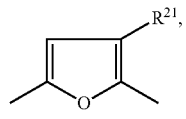

or not substituted, most preferably not substituted

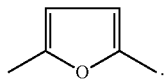

$R^1$, $R^2$, $R^{1'}$, $R^{2'}$, $R^{1''}$, $R^{2''}$, $R^{1*}$ and $R^{2*}$ may be the same or different and are preferably selected from hydrogen, a $C_1$-$C_{100}$alkyl group which can optionally be substituted one or more times with $C_1$-$C_{12}$alkyl, $C_1$-$C_{12}$alkoxy, halogen, $C_5$-$C_{12}$cycloalkyl, cyano, $C_6$-$C_{24}$aryl, $C_2$-$C_{20}$heteroaryl and/or can optionally be interrupted by —O—, —S—, —COO— or —OCO—, a $C_2$-$C_{100}$alkenyl group which can optionally be substituted one or more times with $C_1$-$C_{12}$alkyl, $C_1$-$C_{12}$alkoxy, halogen, $C_5$-$C_{12}$cycloalkyl, cyano, $C_6$-$C_{24}$aryl, $C_2$-$C_{20}$heteroaryl and/or can optionally be interrupted by —O—, —S—, —COO— or —OCO—, a $C_3$-$C_{100}$alkinyl group which can optionally be substituted one or more times with $C_1$-$C_{12}$alkyl, $C_1$-$C_{12}$alkoxy, halogen, $C_5$-$C_{12}$cycloalkyl, cyano, $C_6$-$C_{24}$aryl, $C_2$-$C_{20}$heteroaryl and/or can optionally be interrupted by —O—, —S—, —COO— or —OCO—, a $C_4$-$C_{12}$cycloalkyl group which can optionally be substituted one or more times with $C_1$-$C_{12}$alkyl, $C_1$-$C_{12}$alkoxy, halogen, $C_5$-$C_{12}$cycloalkyl, cyano, $C_6$-$C_{24}$aryl, $C_2$-$C_{20}$heteroaryl and/or can optionally be interrupted by —O—, —S—, —COO— or —OCO—, a $C_6$-$C_{24}$aryl group which can optionally be substituted one or more times with $C_1$-$C_{12}$alkyl, $C_1$-$C_{12}$alkoxy, halogen, $C_5$-$C_{12}$cycloalkyl, cyano, $C_6$-$C_{24}$aryl, $C_2$-$C_{20}$heteroaryl, a $C_2$-$C_{20}$heteroaryl group which can optionally be substituted one or more times with $C_1$-$C_{12}$alkyl, $C_1$-$C_{12}$alkoxy, halogen, $C_5$-$C_{12}$cycloalkyl, cyano, $C_6$-$C_{24}$aryl, $C_2$-$C_{20}$heteroaryl, —CO—$C_1$-$C_{18}$alkyl, —CO—$C_5$-$C_{12}$cycloalkyl, and —COO—$C_1$-$C_{18}$alkyl.

More preferably $R^1$, $R^2$, $R^{1'}$, $R^{2'}$, $R^{1''}$, $R^{2''}$, $R^{1*}$ and $R^{2*}$ are selected from hydrogen, $C_1$-$C_{50}$alkyl, $C_1$-$C_{50}$haloalkyl, $C_7$-$C_{25}$arylalkyl, $C_2$-$C_{50}$alkenyl, $C_2$-$C_{50}$haloalkenyl, allyl, $C_5$-$C_{12}$cycloalkyl, phenyl, or naphthyl which can optionally be substituted one or more times with $C_1$-$C_{12}$alkyl or $C_1$-$C_{12}$alkoxy, —CO—$C_1$-$C_{18}$alkyl, —CO—$C_5$-$C_{12}$cycloalkyl and —COO—$C_1$-$C_{18}$alkyl. Even more preferably $R^1$, $R^2$, $R^{1'}$, $R^{2'}$, $R^{1''}$, $R^{2''}$, $R^{1*}$ and $R^{2*}$ are a $C_1$-$C_{500}$alkyl group. Still more preferably $R^1$, $R^2$, $R^{1'}$, $R^{2'}$, $R^{1''}$, $R^{2''}$, $R^{1*}$ and $R^{2*}$ are a $C_1$-$C_{36}$alkyl group. Most preferably $R^1$, $R^2$, $R^{1'}$, $R^{2'}$, $R^{1''}$, $R^{2''}$, $R^{1*}$ and $R^{2*}$ are a $C_{12}$-$C_{24}$alkyl group, very especially a $C_{16}$-$C_{24}$alkyl group. Preferably $R^1$ is $R^2$, $R^{1'}$ is $R^{2'}$, $R^{1''}$ is $R^{2''}$ and $R^{1*}$ is $R^{2*}$. Most preferably $R^1$, $R^2$, $R^{1'}$, $R^{2'}$, $R^{1''}$, $R^{2''}$, $R^{1*}$ and $R^{2*}$ have the same meaning.

Advantageously, the groups $R^1$, $R^2$, $R^{1'}$, $R^{2'}$, $R^{1''}$, $R^{2''}$, $R^{1*}$ and $R^{2*}$ can be represented by formula

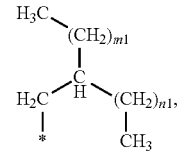

wherein $m1=n1+2$ and $m1+n1 \leq 24$. Chiral side chains, such as $R^1$, $R^2$, $R^{1'}$, $R^{2'}$, $R^{1''}$, $R^{2''}$, $R^{1*}$ and $R^{2*}$, can either be homochiral, or racemic, which can influence the morphology of the compounds.

Preferably a is 1; b is 0, 1, or 2; c is 0, 1, or 2; more preferably a is 1; b is 0, or 1, c is 0, or 1; still more preferably a is 1; b is 0, or 1; c is 0; most preferably a is 1; b is 0; c is 0.

Preferably k+l+r+z is an integer smaller than 5; more preferably k+l+r+z is an integer from 1 to 4; even more preferably k+l+r+z is an integer from 1 to 3; most preferably k+l+r+z is 1 or 3. If q is 0, p is 0, k is 0, r is 0, z is 0 and l is 1, $Ar^5$ is preferably different from a group

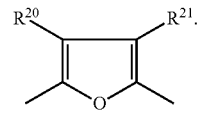

In a preferred embodiment of the present invention two furan groups are not linked directly by a single bond.

Preferably $A^1$ and $A^2$ are the same in the compounds of formulas (Ia), (Ib) and (Ic). Preferably $A^3$ and $A^4$ are the same in the compound of formula (Ib). Preferably $A^3$ and $A^5$ are the same in the compound of formula (Ic). More preferably $A^3$, $A^4$ and $A^5$ are the same in the compound of formula (Ic).

$A^1$ and $A^2$ are independently of each other a group of formula

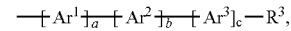

wherein
a is 1, b is 0, or 1, c is 0, or 1,
$Ar^1$, $Ar^2$ and $Ar^3$ are independently of each other a group of formula

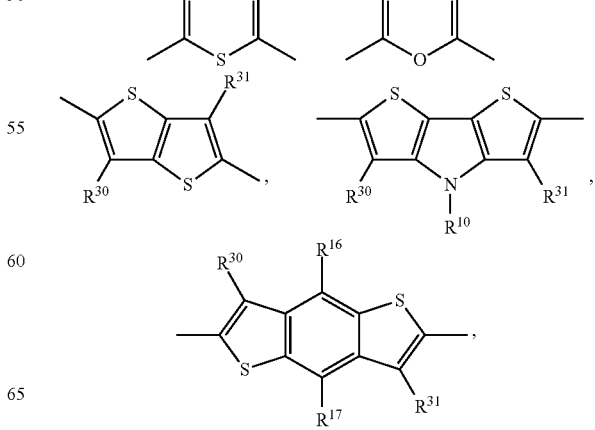

-continued

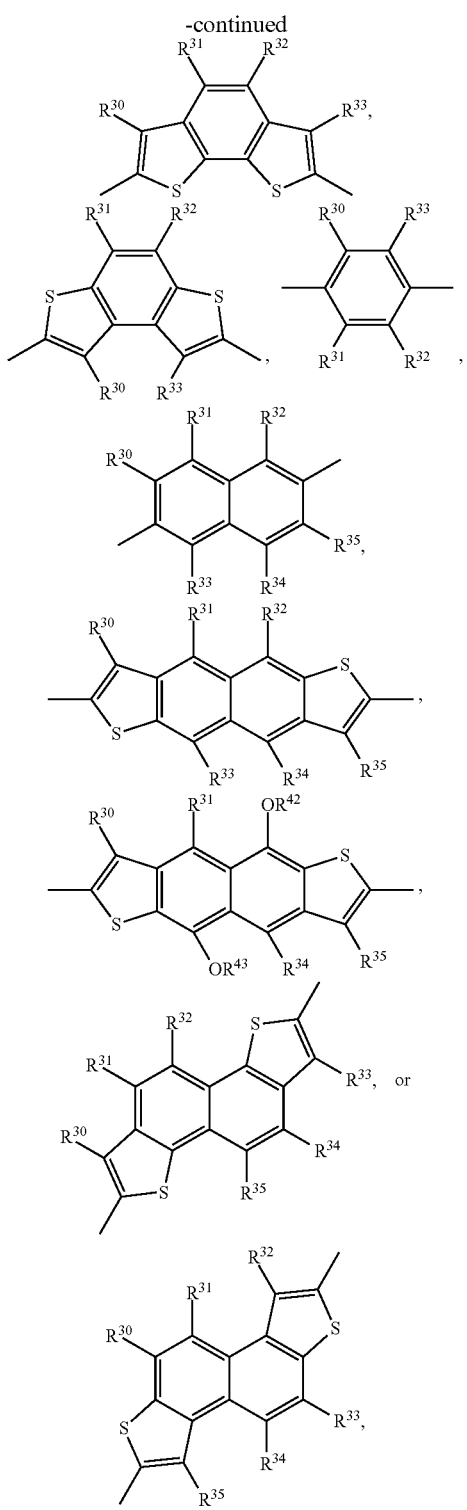

$R^{10}$ is hydrogen, $C_1$-$C_{25}$alkyl or COO—$C_1$-$C_{25}$alkyl,
$R^{16}$ and $R^{17}$ are independently of each other hydrogen, halogen, $C_1$-$C_{25}$alkyl, $C_1$-$C_{25}$alkoxy, $C_7$-$C_{25}$arylalkyl, or

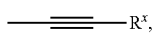

$R^x$ is a $C_1$-$C_{12}$alkyl group, or a tri($C_1$-$C_8$alkyl)silyl group,
$R^{20}$ and $R^{21}$ are independently of each other hydrogen, or $C_1$-$C_{25}$alkyl,
$R^{30}$ to $R^{35}$ are independently of each other hydrogen, or $C_1$-$C_{25}$alkyl,
$R^{42}$ and $R^{43}$ are independently of each other $C_1$-$C_{25}$alkyl;
$R^3$ is hydrogen, halogen, cyano, $C_1$-$C_{25}$ alkyl, or a group of formula

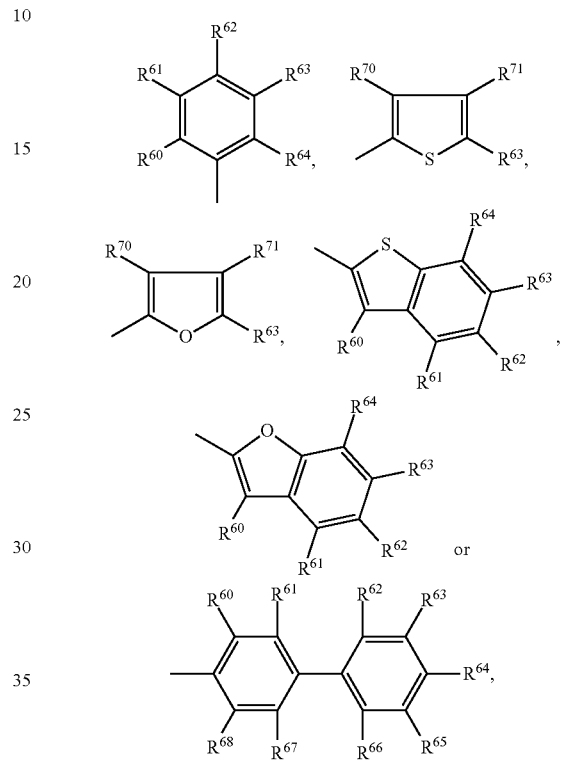

wherein
$R^{60}$ to $R^{68}$ represent independently of each other hydrogen or $C_1$-$C_{25}$alkyl;
$R^{70}$ and $R^{71}$ are independently of each other hydrogen, or $C_1$-$C_{25}$alkyl, or
$R^{70}$ and $R^{71}$ together represent alkylene which may be both bonded via oxygen and/or sulfur to the thienyl residue and which may both have up to 25 carbon atoms.
Preferably, $R^{70}$ and $R^{71}$ are independently of each other hydrogen, or $C_1$-$C_{25}$alkyl.
In a preferred embodiment of the present invention $A^1$ and $A^2$ are independently of each other a group of formula,

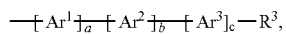

wherein
a is 1, b is 0, or 1, c is 0, or 1,
$Ar^2$ and $Ar^3$ are independently of each other

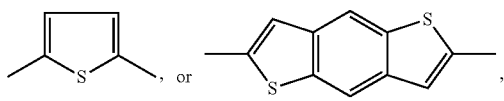

and $R^3$ is H, $C_1$-$C_{25}$alkyl, or phenyl.

In a preferred embodiment of the present invention $A^3$, $A^4$ and $A^5$ are independently of each other a group of formula

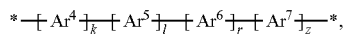

k is 0, 1, or 2; l is 1, 2, or 3; r is 0, or 1; z is 0, 1 or 2;
$Ar^4$, $Ar^5$, $Ar^6$ and $Ar^7$ are independently of each other a group of formula

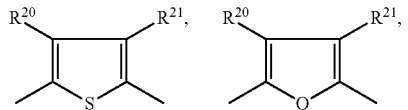

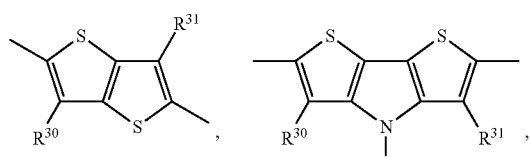

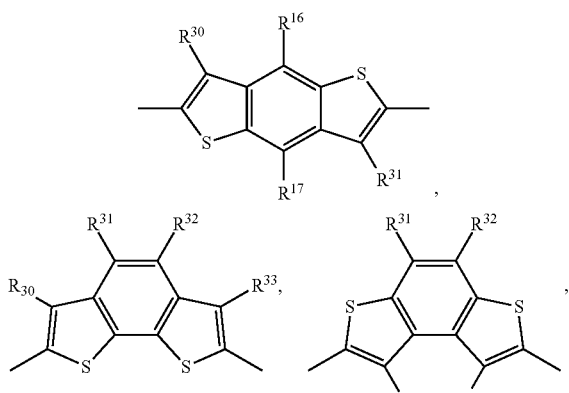

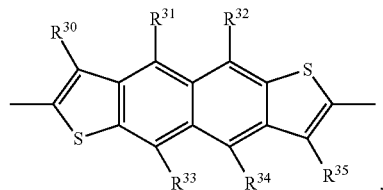

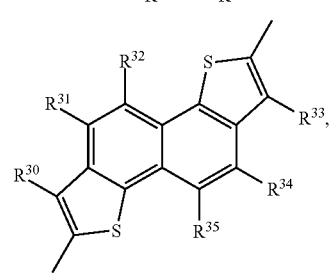

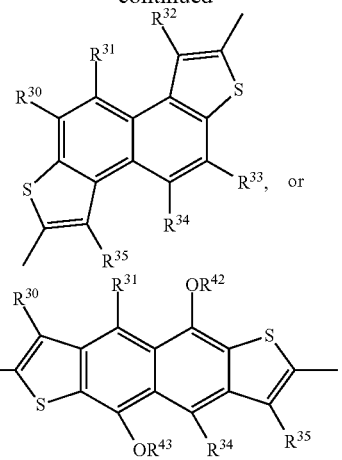

$R^{10}$ is hydrogen, $C_1$-$C_{25}$alkyl or COO—$C_1$-$C_{25}$alkyl,
$R^{16}$ and $R^{17}$ are independently of each other hydrogen, halogen, $C_1$-$C_{25}$alkyl, $C_1$-$C_{25}$alkoxy, $C_7$-$C_{25}$arylalkyl, or

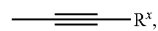

$R^x$ is a $C_1$-$C_{12}$alkyl group, or a tri($C_1$-$C_8$alkyl)silyl group,
$R^{20}$ and $R^{21}$ are independently of each other hydrogen, or $C_1$-$C_{25}$alkyl,
$R^{30}$ to $R^{35}$ are independently of each other hydrogen, or $C_1$-$C_{25}$alkyl, and
$R^{42}$ and $R^{43}$ are independently of each other $C_1$-$C_{25}$alkyl.

More preferably, $A^3$, $A^4$ and $A^5$ are independently of each other a group of formula

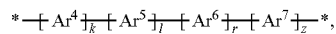

k and z are 0, or 1; l is 1, 2, or 3; r is 0;
$Ar^4$ and $Ar^7$ are a group of formula

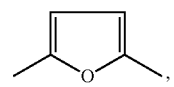

$Ar^5$ is a group of formula

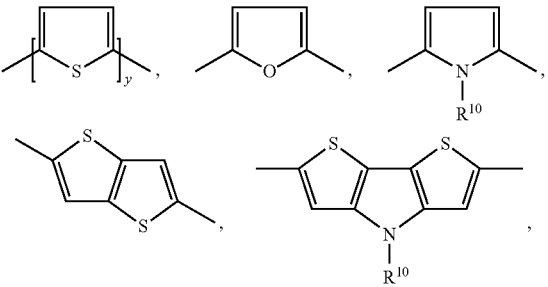

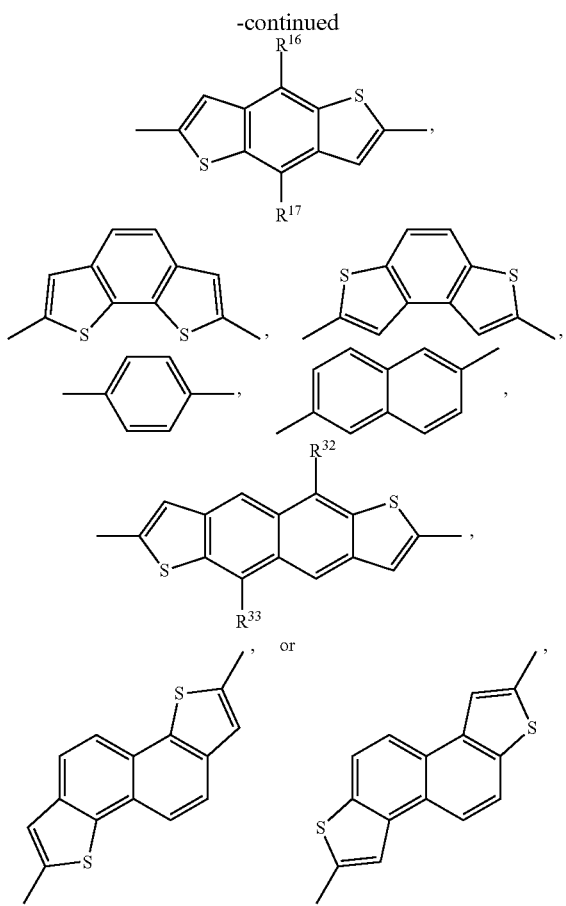

y is 1, 2, or 3,
$R^{10}$ is H, or $C_1$-$C_{25}$alkyl,
$R^{16}$ and $R^{17}$ are H, or $C_1$-$C_{25}$alkyl, and
$R^{32}$ and $R^{33}$ are H, or $C_1$-$C_{25}$alkoxy.

Preferably $R^3$ is hydrogen, halogen, cyano, $C_1$-$C_{25}$ alkyl, or a group of formula

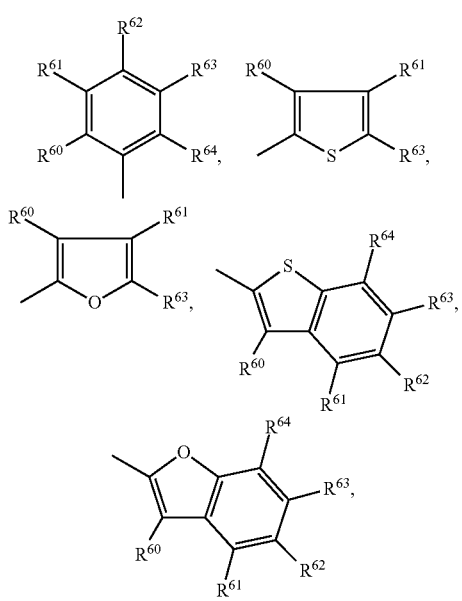

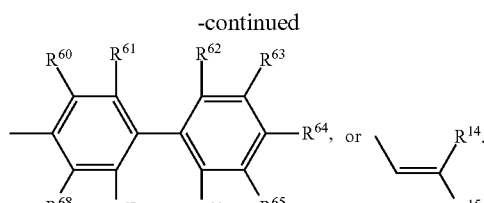

More preferably $R^3$ is hydrogen, halogen, cyano, $C_1$-$C_{25}$ alkyl or

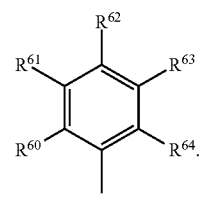

Still more preferably $R^3$ is hydrogen, or $C_1$-$C_{25}$ alkyl. Most preferably $R^3$ is hydrogen.

Preferably $Ar^1$, $Ar^2$, $Ar^3$, $Ar^4$, $Ar^5$, $Ar^6$ and $Ar^7$ are independently of each other a bivalent group of formula

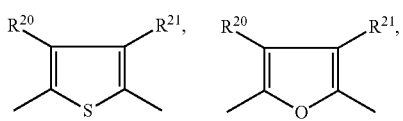

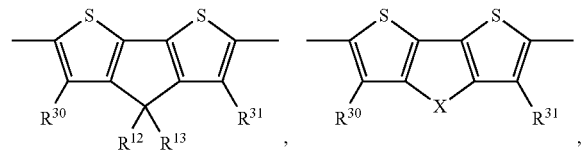

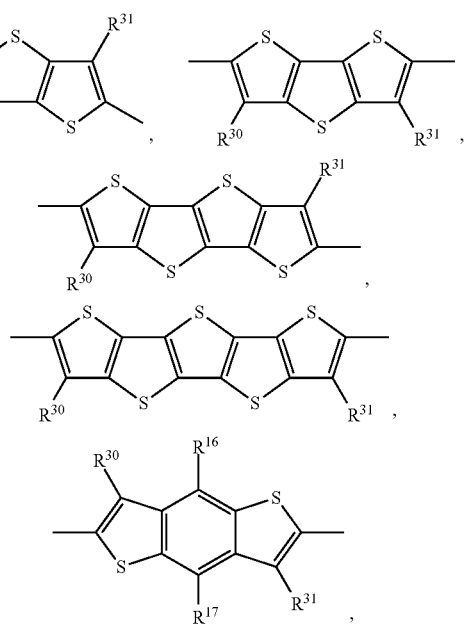

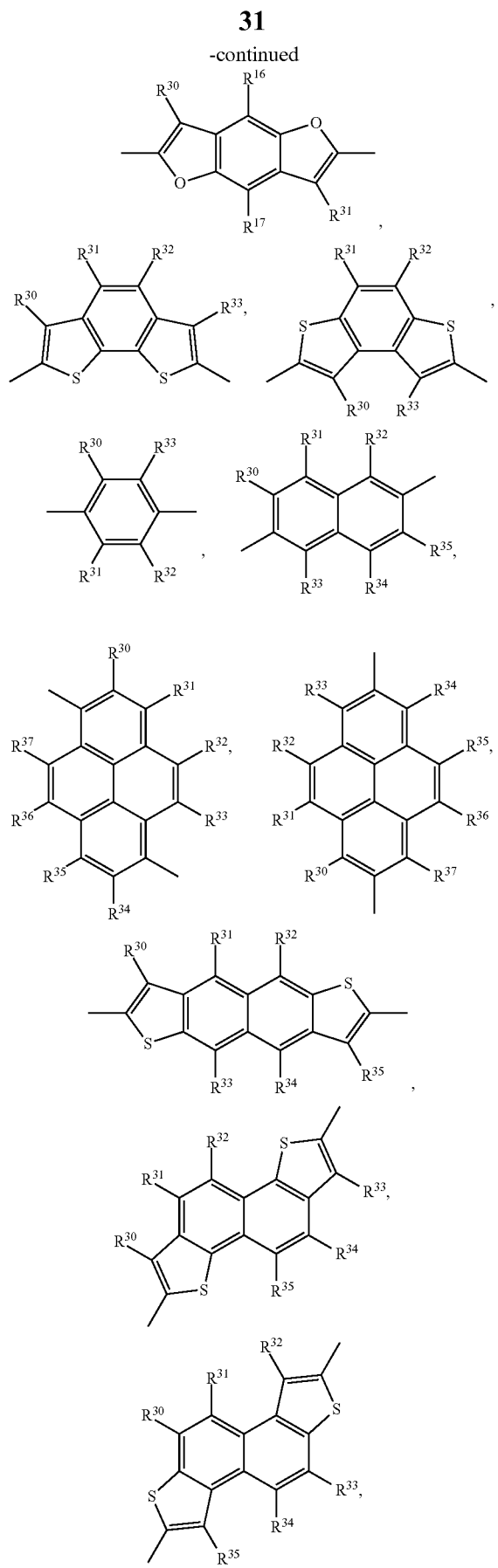
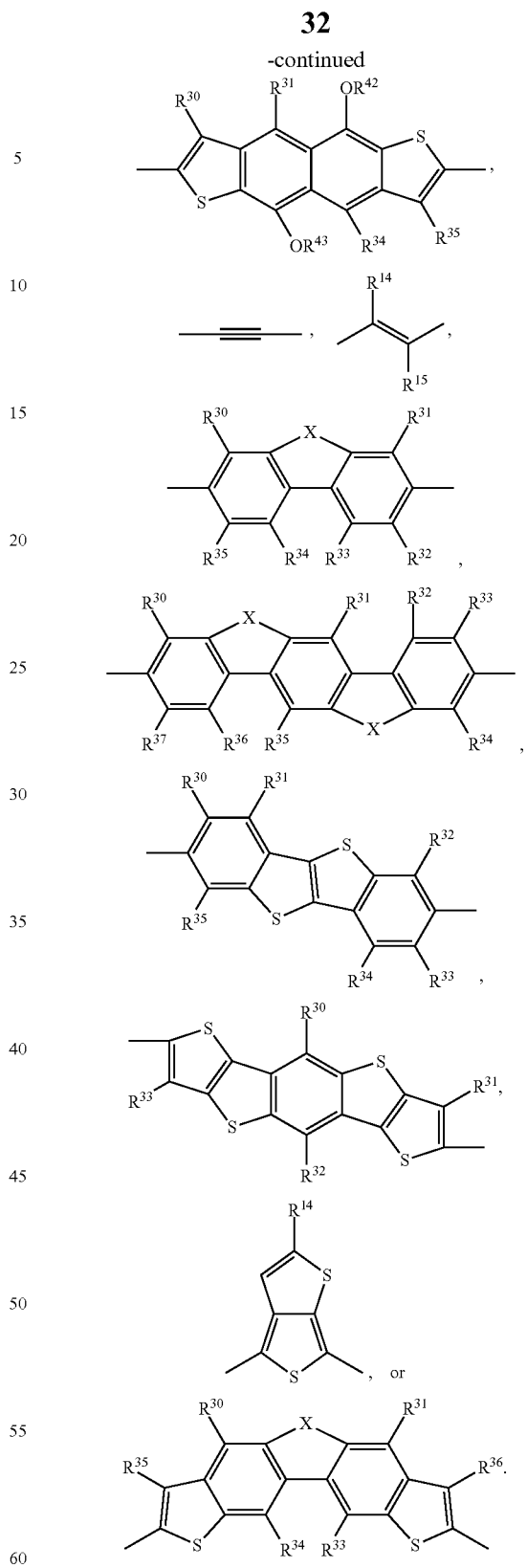
$Ar^1$, $Ar^4$ and $Ar^7$ are preferably selected in such a manner, so that no six-membered ring is directly attached to the diketopyrrolopyrrole basis skeleton.
More preferably $Ar^1$, $Ar^2$, $Ar^3$, $Ar^4$, $Ar^5$, $Ar^6$ and $Ar^7$ are independently of each other a bivalent group of formula

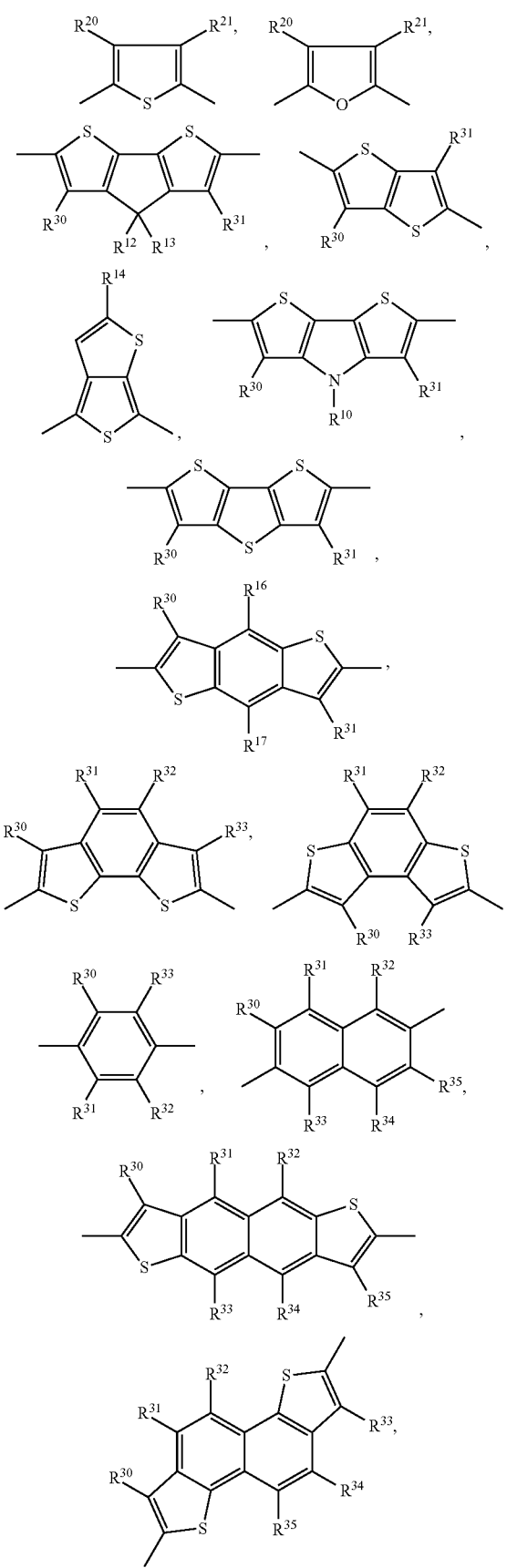
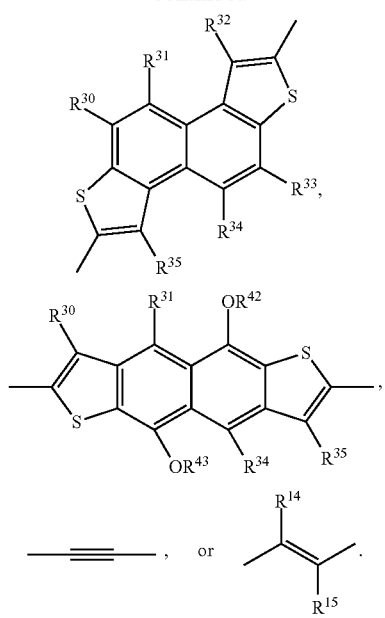
Ar¹, Ar⁴ and Ar⁷ are preferably selected in such a manner, so that no six-membered ring is directly attached to the diketopyrrolopyrrole basis skeleton.
Even more preferably Ar¹, Ar², Ar³, Ar⁴, Ar⁵, Ar⁶ and Ar⁷ are independently of each other a group of formula
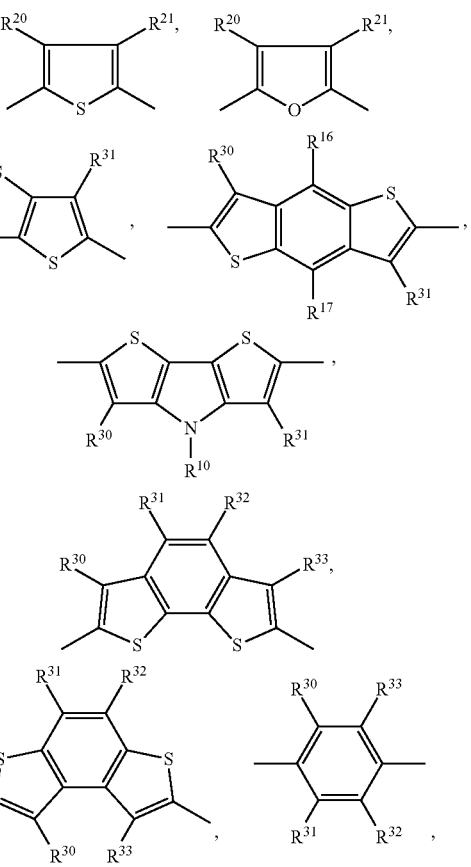

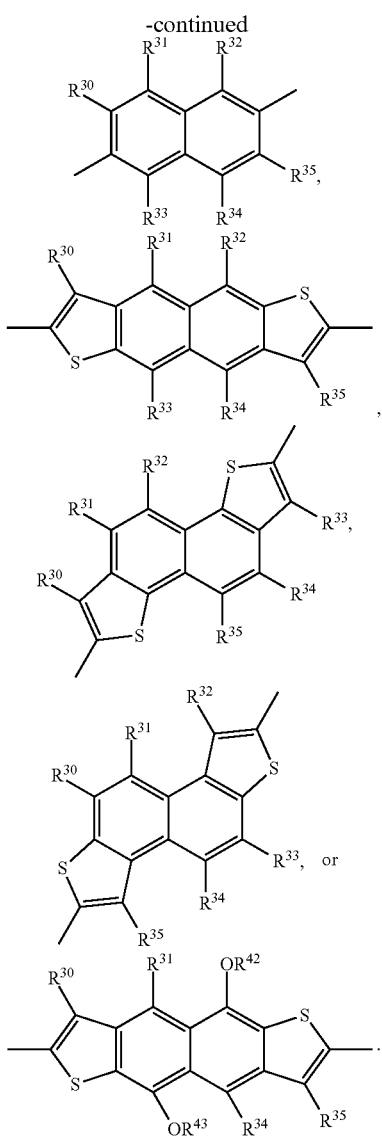

Ar¹, Ar⁴ and Ar⁷ are preferably selected in such a manner, so that no six-membered ring is directly attached to the diketopyrrolopyrrole basis skeleton.

If two moieties selected from Ar¹ to Ar⁷ are linked via a single bond, preferably less than 4 substituents in ortho position to this linking bond selected from $R^{14}$, $R^{15}$, $R^{20}$, $R^{21}$, $R^{30}$, $R^{31}$, $R^{32}$, $R^{33}$, $R^{34}$, $R^{35}$, $R^{36}$, $R^{37}$, $R^{38}$, $R^{40}$, $R^{41}$ are not hydrogen. More preferably less than 3 substituents in ortho position to this linking bond selected from $R^{14}$, $R^{15}$, $R^{20}$, $R^{21}$, $R^{30}$, $R^{31}$, $R^{32}$, $R^{33}$, $R^{34}$, $R^{35}$, $R^{36}$, $R^{37}$, $R^{38}$, $R^{40}$, $R^{41}$ are not hydrogen. Even more preferably only one substituent in ortho position to this linking bond selected from $R^{14}$, $R^{15}$, $R^{20}$, $R^{21}$, $R^{30}$, $R^{31}$, $R^{32}$, $R^{33}$, $R^{34}$, $R^{35}$, $R^{36}$, $R^{37}$, $R^{38}$, $R^{40}$, $R^{41}$ is not hydrogen. Most preferably all substituents in ortho position to this linking bond selected from $R^{14}$, $R^{15}$, $R^{20}$, $R^{21}$, $R^{30}$, $R^{31}$, $R^{32}$, $R^{33}$, $R^{34}$, $R^{35}$, $R^{36}$, $R^{37}$, $R^{38}$, $R^{40}$, $R^{41}$ are hydrogen.

If a moiety selected from Ar¹, Ar⁴ or Ar⁷ is linked via a single bond to the DPP basis skeleton, preferably the substituents in ortho position to this linking bond selected from $R^{14}$, $R^{15}$, $R^{20}$, $R^{21}$, $R^{30}$, $R^{31}$, $R^{32}$, $R^{33}$, $R^{34}$, $R^{35}$, $R^{36}$, $R^{37}$, $R^{38}$, $R^{40}$, $R^{41}$ are hydrogen.

In a preferred embodiment of the present invention A¹ and A² are independently of each other a group of formula

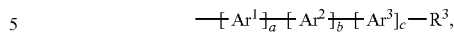

A³, A⁴ and A⁵ are independently of each other a group of formula

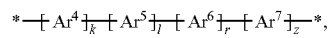

wherein k is 1, l is 1, z is 1, and r is 0,
Ar¹, Ar⁴, and Ar⁷ are

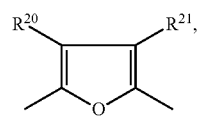

Ar², Ar³, Ar⁵, Ar⁶ are independently of each other a group of formula

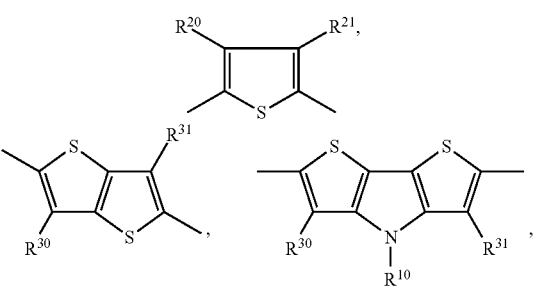

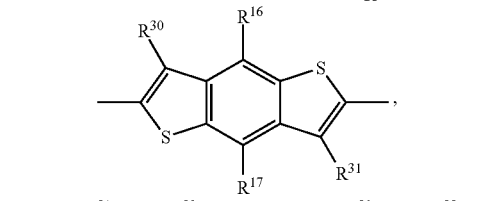

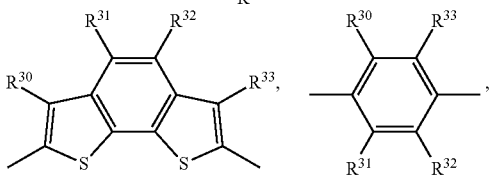

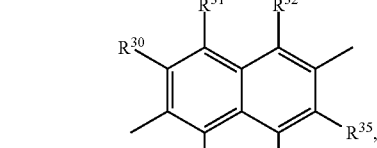

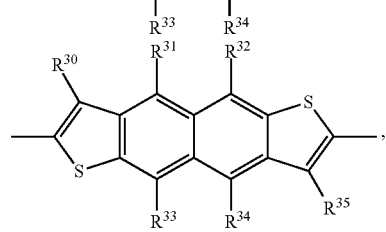

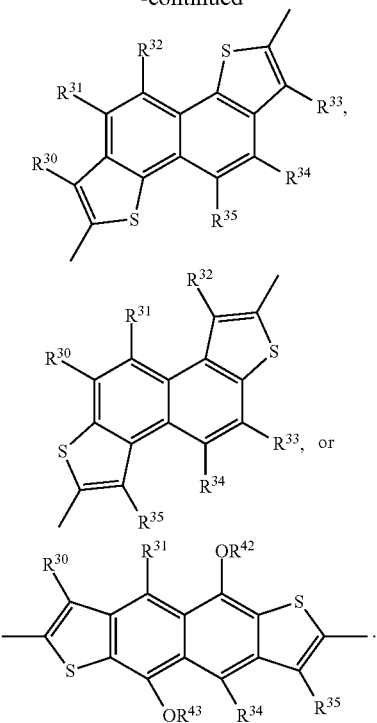

Ar¹, Ar⁴ and Ar⁷ are preferably selected in such a manner, so that no six-membered ring is directly attached to the diketopyrrolopyrrole basis skeleton.

Preferably X is —O—, —S—, —NR$^{10}$—, —Si(R$^{18}$)(R$^{19}$)—, —C(R$^{12}$)(R$^{13}$)—,

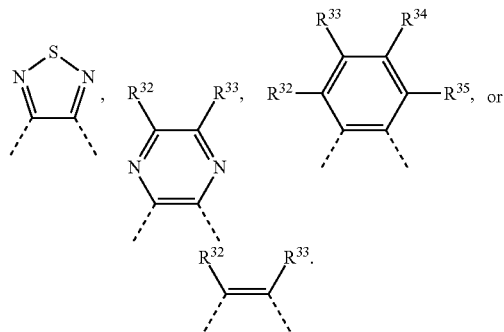

More preferably X is —O—, —S—, —NR$^{10}$—, —C(R$^{12}$)(R$^{13}$)—,

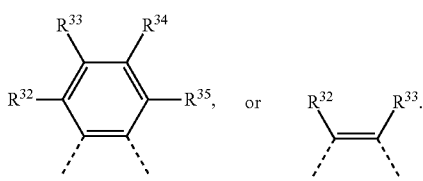

Most preferably X is —S—, —NR$^{10}$—, or

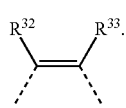

R$^{10}$ and R$^{11}$ are independently of each other hydrogen, $C_1$-$C_{18}$alkyl, $C_1$-$C_{18}$haloalkyl, $C_7$-$C_{25}$arylalkyl, or $C_1$-$C_{18}$alkanoyl, preferably hydrogen, $C_1$-$C_{18}$alkyl, $C_1$-$C_{18}$alkanoyl; most preferably $C_1$-$C_{18}$alkyl.

Preferably R$^{12}$ and R$^{13}$ are independently of each other hydrogen, $C_1$-$C_{18}$alkyl, $C_1$-$C_{18}$haloalkyl, $C_7$-$C_{25}$arylalkyl, or R$^{12}$ and R$^{13}$ together represent oxo, or

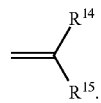

More preferably R$^{12}$ and R$^{13}$ are independently of each other hydrogen, $C_1$-$C_{18}$ alkyl, or R$^{12}$ and R$^{13}$ together represent oxo. Most preferably R$^{12}$ and R$^{13}$ are independently of each other $C_1$-$C_{18}$alkyl.

R$^{14}$ and R$^{15}$ are independently of each other hydrogen, $C_1$-$C_{18}$ alkyl, $C_6$-$C_{24}$aryl, $C_2$-$C_{20}$heteroaryl, —CN or COOR$^{50}$. Preferably R$^{14}$ and R$^{15}$ are independently of each other hydrogen, $C_1$-$C_{18}$ alkyl, —CN, or COOR$^{50}$, where more preferably at least one of R$^{14}$ and R$^{15}$ is —CN, or COOR$^{50}$, and especially R$^{14}$ and R$^{15}$ are both —CN.

R$^{16}$ and R$^{17}$ are independently of each other hydrogen, halogen, $C_1$-$C_{25}$alkyl, $C_1$-$C_{25}$alkoxy, $C_7$-$C_{25}$arylalkyl, or

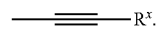

R$^x$ is a $C_1$-$C_{10}$alkyl group, or a tri($C_1$-$C_8$alkyl)silyl group.

Preferably R$^{18}$ and R$^{19}$ are $C_1$-$C_{18}$ alkyl.

Preferably R$^{20}$ and R$^{21}$, are independently of each other hydrogen, $C_1$-$C_{25}$alkyl, COOR$^{50}$, cyano, $C_1$-$C_{18}$alkoxy, or halogen. More preferably R$^{20}$ and R$^{21}$, are independently of each other hydrogen, $C_1$-$C_{25}$alkyl, $C_1$-$C_{18}$ alkoxy, or halogen. Even more preferably R$^{20}$ and R$^{21}$ are independently of each other hydrogen, or $C_1$-$C_{25}$alkyl. Most preferably R$^{20}$ and R$^{21}$ are hydrogen;

Preferably R$^{30}$ to R$^{37}$ are independently of each other hydrogen, $C_1$-$C_{25}$alkyl, COOR$^{50}$, cyano, $C_1$-$C_{18}$alkoxy, or halogen. More preferably R$^{30}$ to R$^{38}$ are independently of each other hydrogen, $C_1$-$C_{25}$alkyl, $C_1$-$C_{18}$ alkoxy, or halogen. Even more preferably R$^{30}$ to R$^{38}$ are independently of each other hydrogen or $C_1$-$C_{25}$alkyl. Most preferably R$^{30}$ to R$^{38}$ are hydrogen.

Preferably R$^{40}$ and R$^{41}$ are independently of each other hydrogen, $C_1$-$C_{25}$alkyl, COOR$^{50}$, or cyano. More preferably R$^{40}$ and R$^{41}$, are independently of each other hydrogen, $C_1$-$C_{25}$alkyl, or cyano. Even more preferably R$^{40}$ and R$^{41}$ are independently of each other hydrogen, or $C_1$-$C_{25}$alkyl. Most preferably R$^{40}$ and R$^{41}$ are independently of each other $C_1$-$C_{25}$alkyl.

Preferably R$^{42}$ and R$^{43}$ are independently of each other $C_1$-$C_{18}$ alkyl.

R$^{50}$ is $C_1$-$C_{25}$alkyl, $C_1$-$C_{25}$haloalkyl, $C_7$-$C_{25}$arylalkyl, $C_6$-$C_{24}$aryl, or $C_2$-$C_{20}$heteroaryl. R$^{50}$ is preferably $C_1$-$C_{25}$alkyl, $C_1$-$C_{25}$haloalkyl, $C_7$-$C_{25}$arylalkyl, most preferably $C_1$-$C_{25}$alkyl.

Preferably R$^{60}$ to R$^{68}$ represent independently of each other hydrogen, $C_1$-$C_{25}$alkyl, $C_1$-$C_{18}$ alkoxy, or halogen. More preferably R$^{60}$ to R$^{68}$ represent independently of each other hydrogen, or $C_1$-$C_{25}$alkyl. Most preferably R$^{60}$ to R$^{68}$ represent hydrogen.

In a particularly preferred embodiment the present invention is directed to compounds of formula

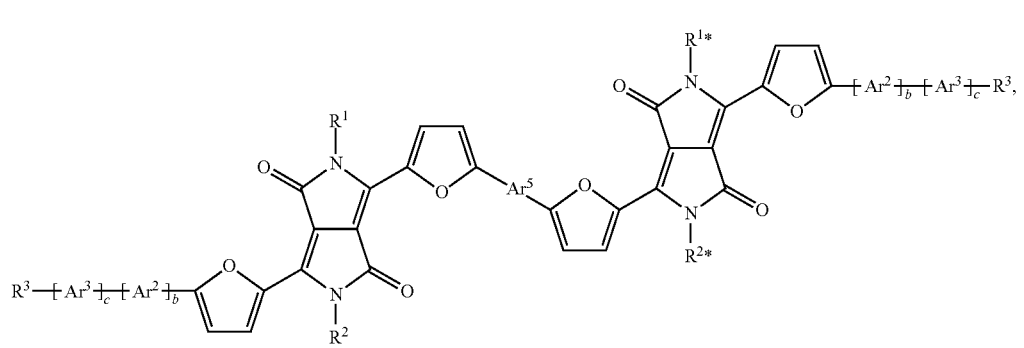
(IIa)
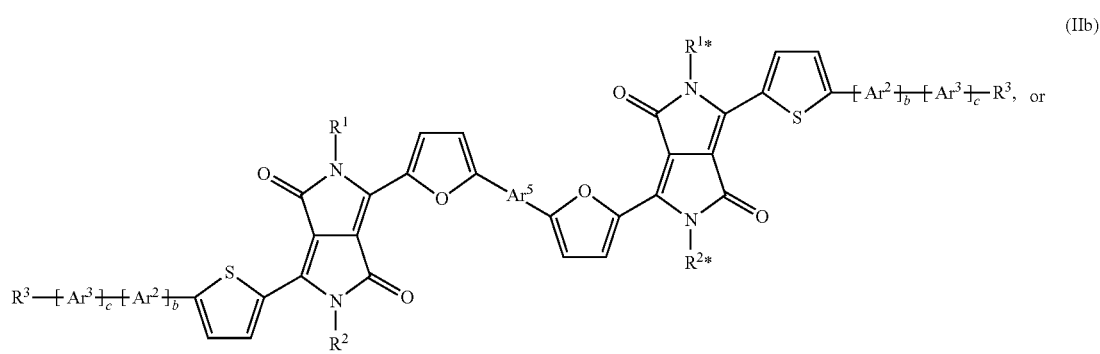
(IIb)
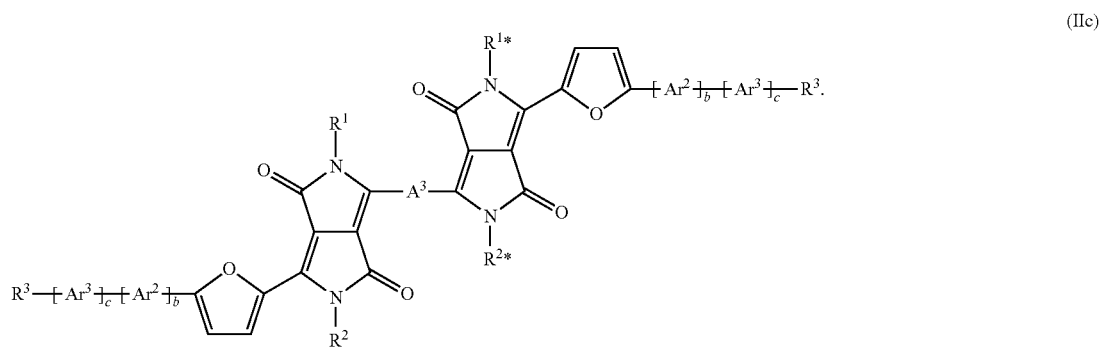
(IIc)
Even more preferred are compounds of formula
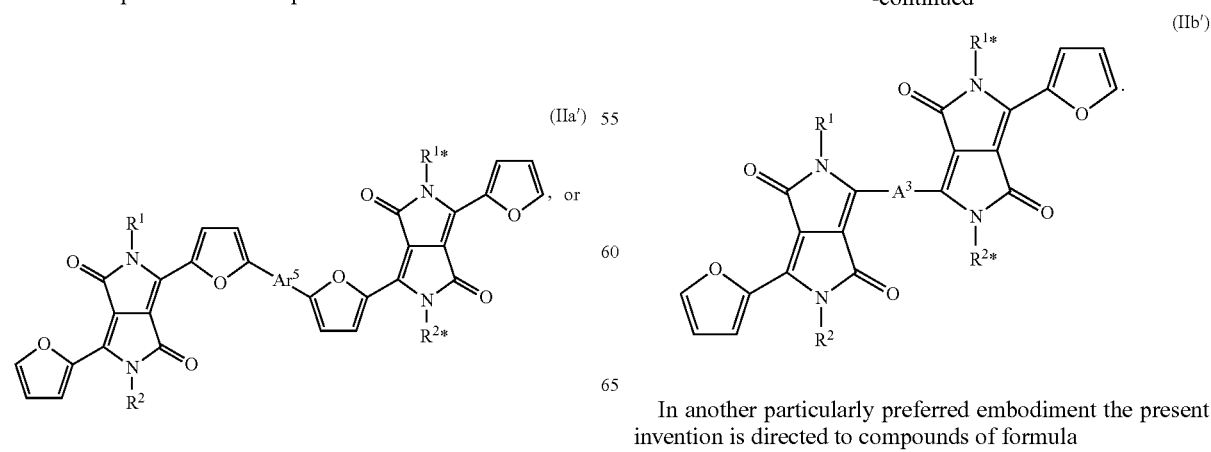
(IIa′)
(IIb′)
In another particularly preferred embodiment the present invention is directed to compounds of formula

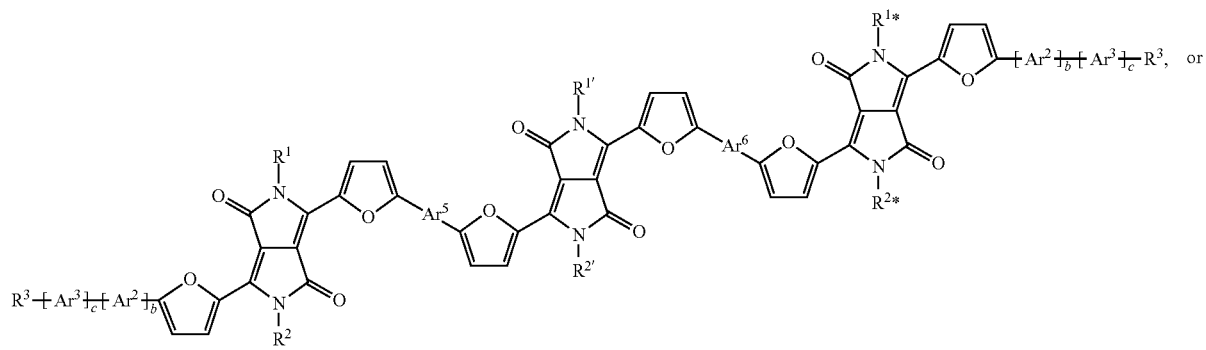
(IIIa)
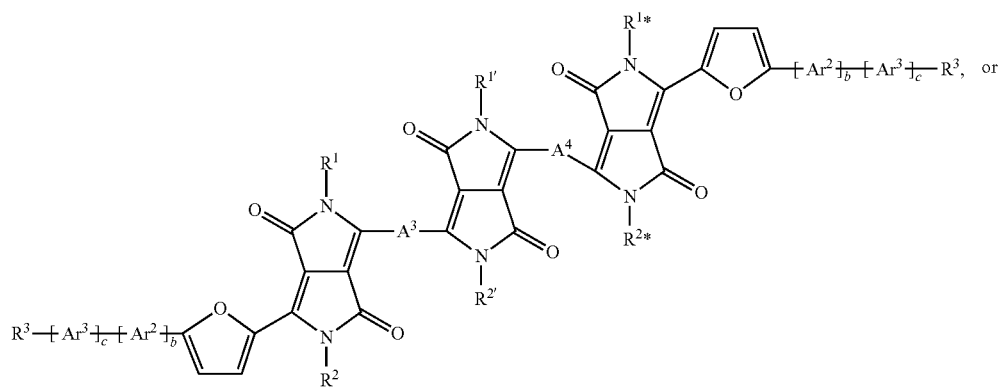
(IIIb)
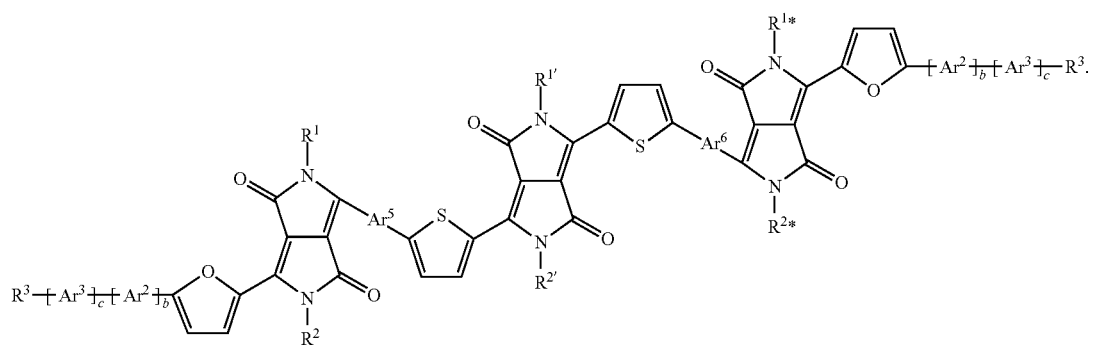
(IIIc)
Even more preferred are compounds of formula
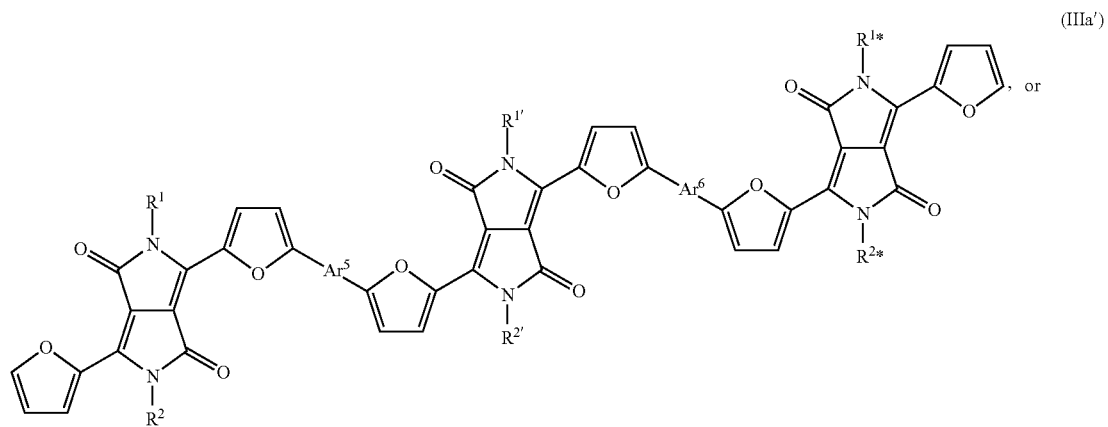
(IIIa′)

-continued

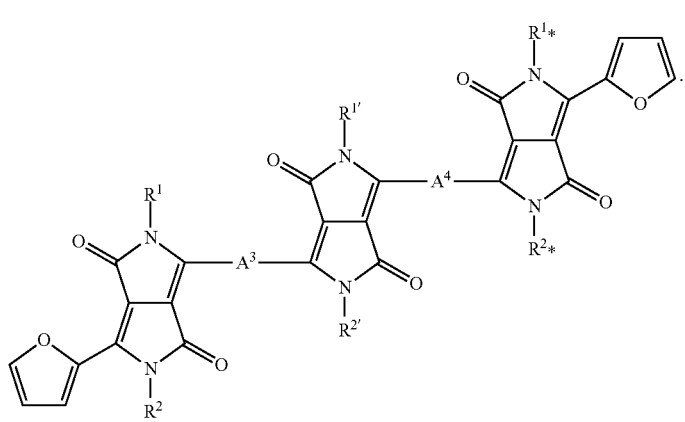
(IIIb')

b is 0, or 1, c is 0, or 1.

$A^3$, $A^4$, $Ar^5$ and $Ar^6$ are independently of each other a group of formula

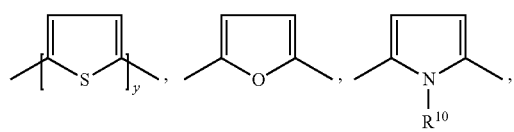

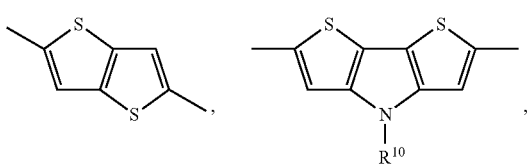

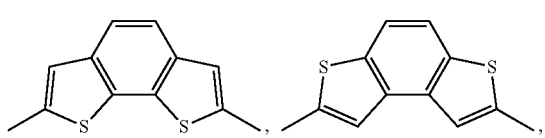

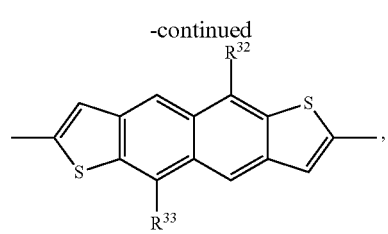

, or y is 1, 2, or 3.

$Ar^2$ and $Ar^3$ are independently of each other

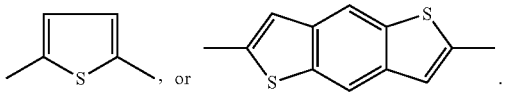

$R^3$ is H, $C_1$-$C_{25}$alkyl, or phenyl. $R^{10}$ is H, or $C_1$-$C_{25}$alkyl. $R^{16}$ and $R^{17}$ are H, or $C_1$-$C_{25}$alkyl. $R^{32}$ and $R^{33}$ are H, or $C_1$-$C_{25}$alkoxy.

$R^1$, $R^2$, $R^{1'}$, $R^{2'}$, $R^{1*}$ and $R^{2*}$ are selected from hydrogen, $C_1$-$C_{50}$alkyl, $C_1$-$C_{50}$haloalkyl, $C_7$-$C_{25}$arylalkyl, $C_2$-$C_{50}$alkenyl, $C_2$-$C_{50}$haloalkenyl, allyl, $C_5$-$C_{12}$cycloalkyl, phenyl, or naphthyl which can optionally be substituted one or more times with $C_1$-$C_{12}$alkyl or $C_1$-$C_{12}$alkoxy, —CO—$C_1$-$C_{18}$alkyl, —CO—$C_5$-$C_{12}$cycloalkyl and —COO—$C_1$-$C_{18}$alkyl.

At present most preferred are compounds A-1 to A-22, B-1 and B-2. Reference is made to claim 9.

In an additional embodiment the present invention is directed to compounds of formula

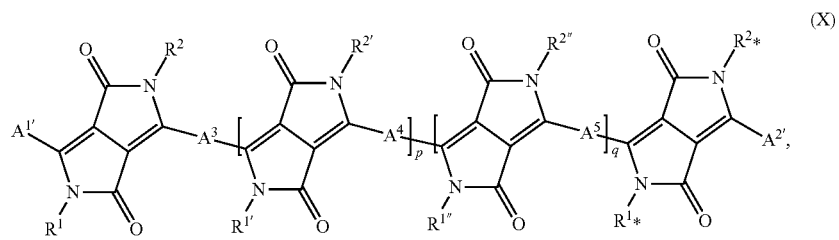
(X)

wherein
$A^{1'}$ and $A^{2'}$ are independently of each other a group of formula

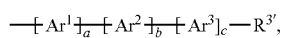

$R^{3'}$ is independently in each occurrence $ZnX^{12}$, $-SnR^{207}R^{208}R^{209}$, wherein $R^{207}$, $R^{208}$ and $R^{209}$ are identical or different and are H or $C_1$-$C_6$alkyl, wherein two radicals optionally form a common ring and these radicals are optionally branched or unbranched and $X^{12}$ is a halogen atom, very especially I, or Br; $-OS(O)_2CF_3$, $-OS(O)_2$-aryl, especially

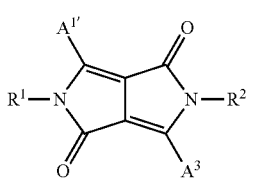

$-OS(O)_2CH_3$, $-B(OH)_2$, $-B(OH)_3-$, $-BF_3$, $-B(OY^1)_2$,

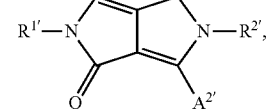

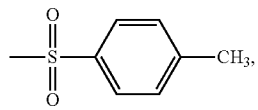, or 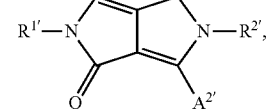

wherein $Y^1$ is independently in each occurrence a $C_1$-$C_{12}$alkyl group and $Y^2$ is independently in each occurrence a $C_2$-$C_{10}$alkylene group, such as $-CY^3Y^4-CY^5Y^6-$, or $-CY^7Y^8-CY^9Y^{10}-CY^{11}Y^{12}-$, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{12}$alkyl group, especially $-C(CH_3)_2C(CH_3)_2-$, $-C(CH_3)_2CH_2C(CH_3)_2-$, or $-CH_2C(CH_3)_2CH_2-$, and $Y^{13}$ and $Y^{14}$ are independently of each other hydrogen, or a $C_1$-$C_{12}$alkyl group; a, b, c, q, p, $R^1$, $R^2$, $R^{1'}$, $R^{2'}$, $R^{1''}$, $R^{2''}$, $R^{1*}$, $R^{2*}$, $Ar^1$, $Ar^2$, $Ar^3$, $A^3$, $A^4$ and $A^5$ are as defined above.

The compound of formula X is preferably a compound of formula

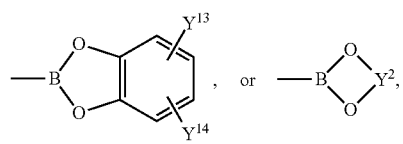 (Xa)

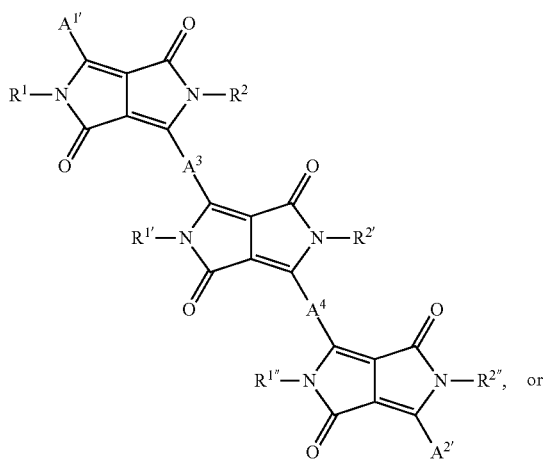 (Xb)

, or

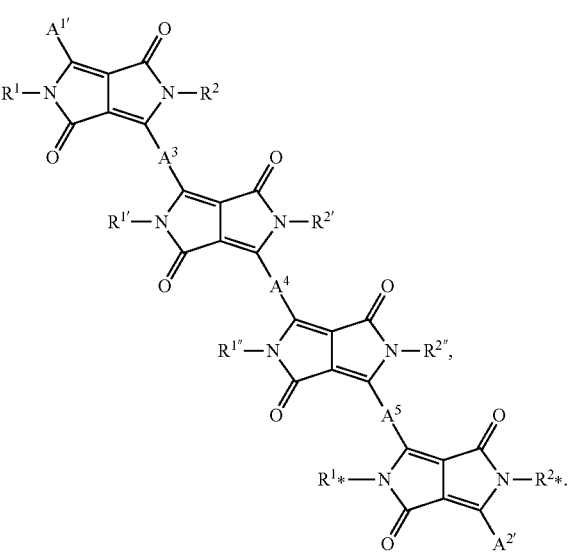 (Xc)

The compounds of the formula X, especially Xa, Xb and Xc are intermediates in the production of polymers and can be used in the production of polymers.

Accordingly, the present invention is also directed to polymers comprising repeating units of formula

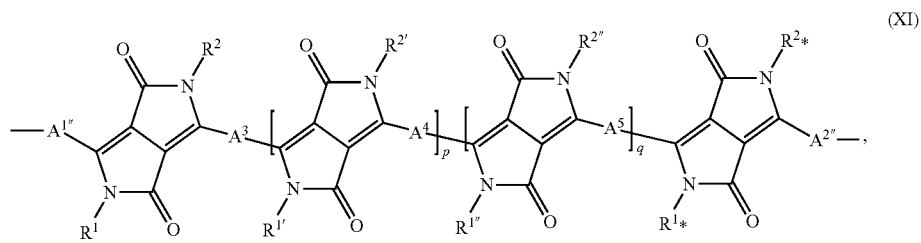

(XI)

wherein $A^{1''}$ and $A^{2''}$ are independently of each other a group of formula

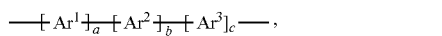

wherein a, b, c, p, q, $R^1$, $R^2$, $R^{1'}$, $R^{2'}$, $R^{1''}$, $R^{2''}$, $R^{1*}$, $R^{2*}$, $Ar^1$, $Ar^2$, $Ar^3$, $A^3$, $A^4$ and $A^5$ are as defined above. The polymers of the present invention may be used in the production of semiconductor devices. Accordingly, the present invention is also directed to semiconductor devices comprising a polymer of the present invention.

A process for the preparation of a compound of the formula

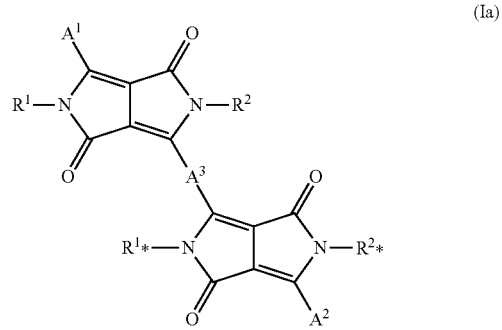

(Ia)

($R^1=R^2=R^{1*}=R^{2*}$; $A^1=A^2$) comprises (a) reacting (in the presence of a strong base) 2 mole of a disuccinate with 1 mole of a nitrile of the formula

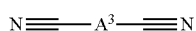

and 2 mole of a nitrile of the formula $A^1\mathrm{-\!\!\!=\!\!\!=\!\!\!N}$, (b) reacting the compound of formula

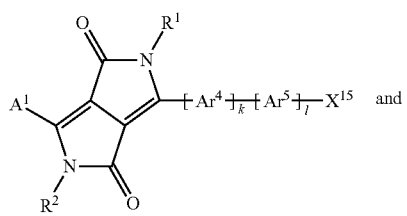

(IX')

obtained in step a) with a halogenide of the formula $R^1\mathrm{-X^{16}}$ ($X^{16}$ is halogen, especially iodide or bromide) in the presence of a suitable base, like potassium carbonate, in a suitable solvent, like N-methylpyrrolidone.

A further synthesis route is, for example, the reaction of mono-halogenated compounds

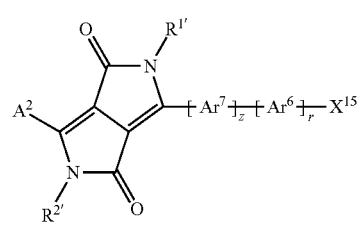

under Yamamoto reaction conditions with the aid of a Nickel complex, wherein compounds of formula

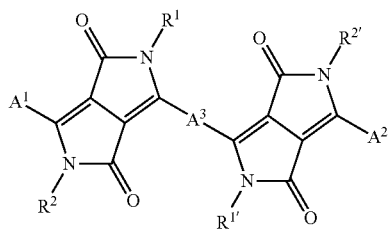

are obtained. $X^{15}$ is a halogen atom, especially Br, or I. l and z are independently of each other 1, or 2. k is 0, 1 or 2. r is 0, or 1. $R^1$, $R^2$, $R^{1'}$, $R^{2'}$, $A^1$ and $A^2$ are as defined above. $Ar^4$, $Ar^5$, $Ar^6$, $Ar^7$ and $A^3$, respectively are as defined above.

Another process for the preparation of compounds of formula

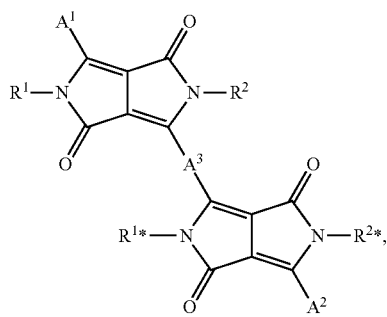

wherein $R^2$ is $R^{1*}$, comprises (a) reacting (in the presence of a strong base) 2 moles of a compound of formula

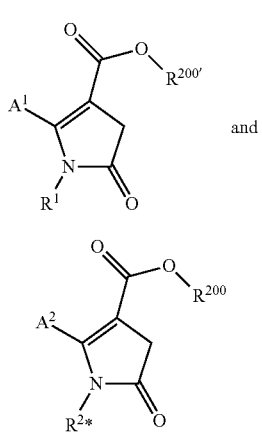

($R^{200}$ and $R^{200'}$ are independently of each other a $C_1$-$C_8$alkyl group, or a benzyl group) with 1 mole of a di-nitrile compound of the formula

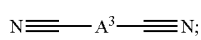

(b) and then alkylation of the compound of formula

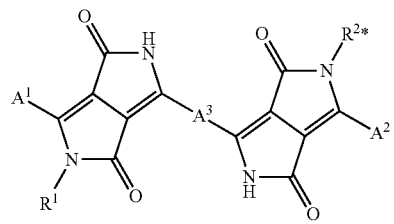

obtained in step (a) with a compound $R^2$—$X^{16}$ ($X^{16}$ is halogen, especially iodide or bromide) under basic conditions (preferably $K_2CO_3$) in a dry solvent such as e.g. dimethylformamide.

The compounds of formula XV and XV' can be synthesized, for example, in analogy to the methods described in C. Morton et al., Tetrahedron 58 (2002) 5547-5565.

Another process for the preparation of a compound of the formula

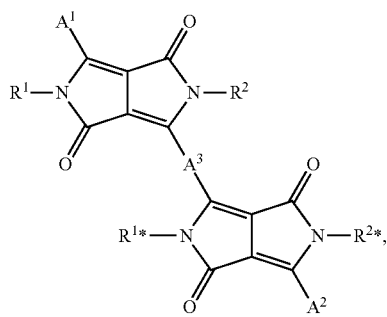

($R^1$=$R^2$=$R^{1*}$=$R^{2*}$) comprises (a) reacting (in the presence of a strong base) 2 mole of a disuccinate with 1 mole of a nitrile of the formula

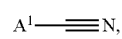

and 2 mole of a nitrile of the formula $A^1$≡N, (b) reacting the compound of formula

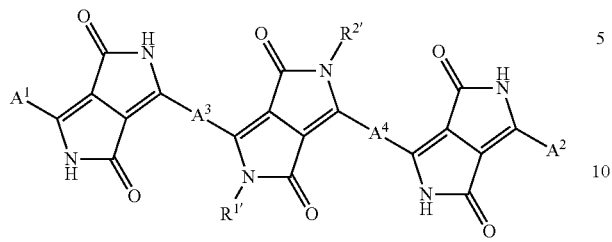
(IX")

obtained in step a) with a halogenide of the formula $R^1$—$X^{16}$ ($X^{16}$ is halogen, especially Br, or I) in the presence of a suitable base, like potassium carbonate, in a suitable solvent, like N-methyl-pyrrolidone, $R^1$, $R^{1'}$, $R^{2'}$, $A^1$, $A^2$, $A^3$ and $A^4$ are as defined above. Compounds of formula

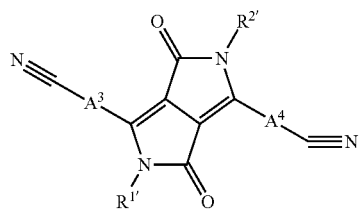

can be prepared by reacting

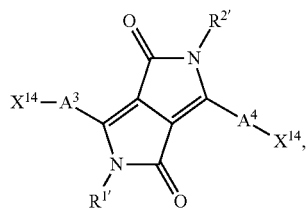

wherein $X^{14}$ is halogen, such as, for example, Br, or I, with copper(I)cyanide. The reaction with copper(I)cyanide is carried out in a suitable solvent, like dimethylforamide (DMF) and is carried out at a temperature from about room temperature to about 180° C., preferably from about 100° C. to about 170° C., e.g. at 130° C. Reference is made to WO2012/041849 and Frank Würthner et al., Chem. Commun., 2011, 47, 1767-1769.

Another process for the preparation of compounds of formula

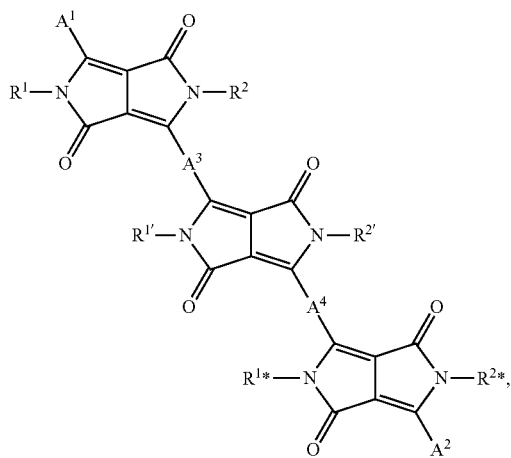
(Ib)

wherein $R^2$ is $R^{1*}$, comprises
(a) reacting (in the presence of a strong base) 2 moles of a compound of formula

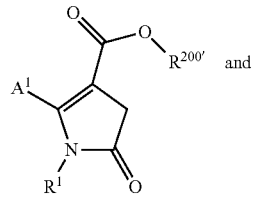
(XV)

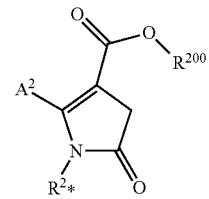
(XV')

($R^{200}$ and $R^{200'}$ are independently of each other a $C_1$-$C_8$alkyl group, or a benzyl group) with 1 mole of a di-nitrile compound of the formula

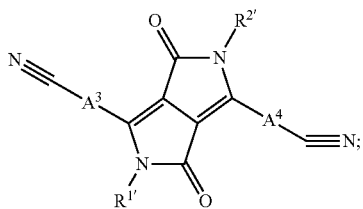

(b) and then alkylation of the compound of formula

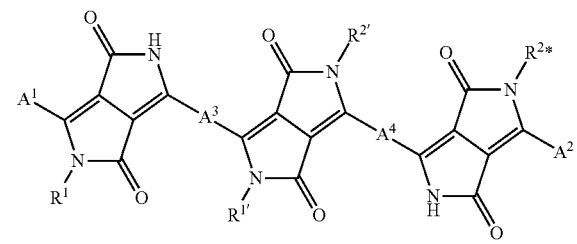

obtained in step (a) with a compound $R^2$—$X^{16}$ ($X^{16}$ is halogen, especially iodide or bromide) under basic conditions (preferably $K_2CO_3$) in a dry solvent such as e.g. dimethylformamide.

Alternatively, compounds of the formula

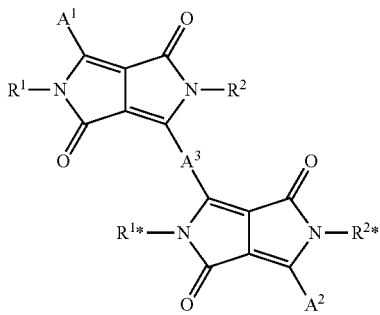
(Ia)

($R^1$=$R^{1*}$; $R^2$=$R^{2*}$, $A^3$ is a group of formula

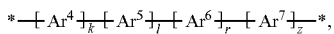

$Ar^4$ is $Ar^7$, k is 1, or 2, z is 1,
or 2) may be prepared by reacting a compound of formula

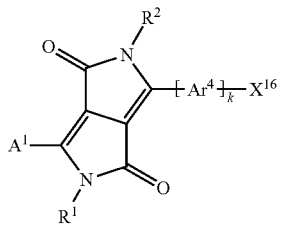

with a compound of formula

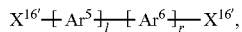

wherein $X^{16'}$ is —B(OH)$_2$, —B(OH)$_3$—, —BF$_3$, —B(OY$^1$)$_2$,

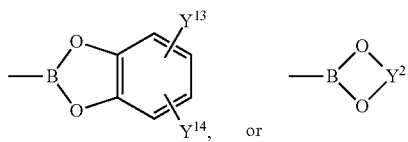

and $X^{16}$ is halogen, such as, for example, Br, or I.

The Suzuki reaction is typically conducted at about 0° C. to 180° C. in an aromatic hydrocarbon solvent such as toluene, xylene. Other solvents such as dimethylformamide, dioxane, dimethoxyethan and tetrahydrofuran can also be used alone, or in mixtures with an aromatic hydrocarbon. An aqueous base, preferably sodium carbonate or bicarbonate, potassium phosphate, potassium carbonate or bicarbonate is used as activation agent for the boronic acid, boronate and as the HBr scavenger. A condensation reaction may take 0.2 to 100 hours. Organic bases, such as, for example, tetraalkylammonium hydroxide, and phase transfer catalysts, such as, for example TBAB, can promote the activity of the boron (see, for example, Leadbeater & Marco; Angew. Chem. Int. Ed. Eng. 42 (2003) 1407 and references cited therein). Other variations of reaction conditions are given by T. I. Wallow and B. M. Novak in J. Org. Chem. 59 (1994) 5034-5037; and M. Remmers, M. Schulze, and G. Wegner in Macromol. Rapid Commun. 17 (1996) 239-252.

The compounds of the present invention can also be sythesized by the Stille coupling (see, for example, Babudri et al, J. Mater. Chem., 2004, 14, 11-34; J. K. Stille, Angew. Chemie Int. Ed. Engl. 1986, 25, 508). In order to carry out the process, tin compounds

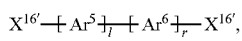

wherein $X^{16'}$ is —SnR$^{207}$R$^{208}$R$^{209}$, and the halogen compound

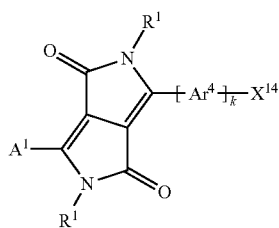

are preferably introduced into one or more inert organic solvents and stirred at a temperature of from 0 to 200° C., preferably from 30 to 170° C. for a period of from 1 hour to 200 hours, preferably from 5 hours to 150 hours.

Reference is made to WO2009/047104 and WO2012/041849 with respect to the preparation of the strating materials and the compounds of formula I.

In the above Stille and Suzuki coupling reactions the halogen $X^{16}$ on the halogenated reaction partner can be replaced with the $X^{16'}$ moiety and at the same time the $X^{16'}$ moiety of the other reaction partner is replaced by $X^{16}$.

Compounds of formula Ib can be prepared in analogy to the synthesis of compounds of formula Ia via Suzuki, or Stille reaction starting from the corresponding building blocks, e.g.: Two equivalents of a compound of formula

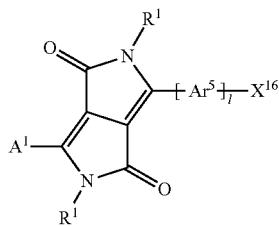

are reacted with one equivalent of a compound of formula

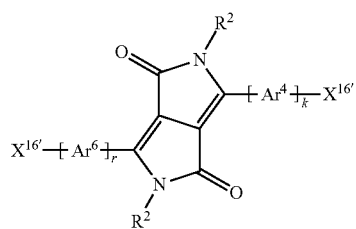

to give a compound of formula

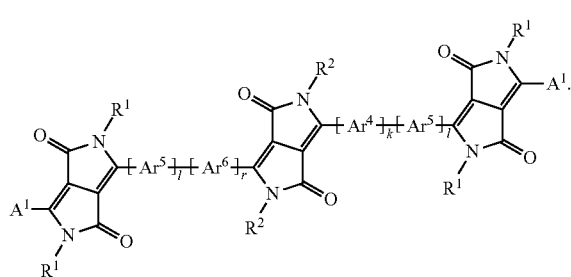

The compounds, wherein $R^1$, $R^2$, $R^{1'}$, $R^{2'}$, $R^{1''}$, $R^{2''}$, $R^{1*}$ and/or $R^{2*}$ are hydrogen can be obtained by using a protecting group which can be removed after synthesis of the precursor compound (see, for example, EP-A-0648770, EP-A-0648817, EP-A-0742255, EP-A-0761772, WO98/32802, WO98/45757, WO98/58027, WO99/01511, WO00/17275, WO00/39221, WO00/63297 and EP-A-1086984). Conversion of the precursor compound into the desired final compound is carried out by means of fragmentation under known conditions, for example thermally, optionally in the presence of an additional catalyst, for example the catalysts described in WO00/36210.

An example of such a protecting group is group of formula

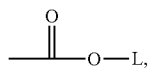

wherein L is any desired group suitable for imparting solubility.

L is preferably a group of formula

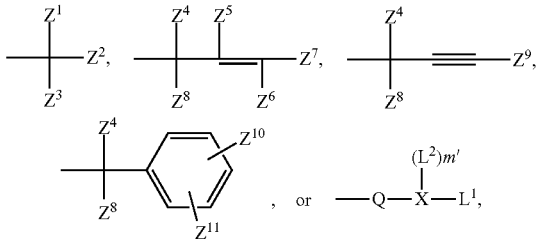

wherein $Z^1$, $Z^2$ and $Z^3$ are independently of each other $C_1$-$C_6$alkyl,
$Z^4$ and $Z^8$ are independently of each other $C_1$-$C_6$alkyl, $C_1$-$C_6$alkyl interrupted by oxygen, sulfur or $N(Z^{12})_2$, or unsubstituted or $C_1$-$C_6$alkyl-, $C_1$-$C_6$alkoxy-, halo-, cyano- or nitro-substituted phenyl or biphenyl,
$Z^5$, $Z^6$ and $Z^7$ are independently of each other hydrogen or $C_1$-$C_6$alkyl,
$Z^9$ is hydrogen, $C_1$-$C_6$alkyl or a group of formula

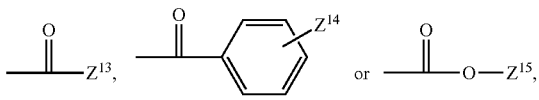

$Z^{10}$ and $Z^{11}$ are each independently of the other hydrogen, $C_1$-$C_6$alkyl, $C_1$-$C_6$alkoxy, halogen, cyano, nitro, $N(Z^{12})_2$, or unsubstituted or halo-, cyano-, nitro-, $C_1$-$C_6$alkyl- or $C_1$-$C_6$alkoxy-substituted phenyl,
$Z^{12}$ and $Z^{13}$ are $C_1$-$C_6$alkyl, $Z^{14}$ is hydrogen or $C_1$-$C_6$alkyl, and $Z^{15}$ is hydrogen, $C_1$-$C_6$alkyl, or unsubstituted or $C_1$-$C_6$alkyl-substituted phenyl,
Q is p,q-$C_2$-$C_6$alkylene unsubstituted or mono- or poly-substituted by $C_1$-$C_6$alkoxy, $C_1$-$C_6$alkylthio or $C_2$-$C_{12}$dialkylamino, wherein p and q are different position numbers,
X is a hetero atom selected from the group consisting of nitrogen, oxygen and sulfur, m' being the number 0 when X is oxygen or sulfur and m being the number 1 when X is nitrogen, and
$L^1$ and $L^2$ are independently of each other unsubstituted or mono- or poly-$C_1$-$C_{12}$ alkoxy-, —$C_1$-$C_{12}$alkylthio-, —$C_2$-$C_{24}$dialkylamino-, —$C_6$-$C_{12}$aryloxy-, —$C_6$-$C_{12}$arylthio-, —$C_7$-$C_{24}$alkylarylamino- or —$C_{12}$-$C_{24}$diarylamino-substituted $C_1$-$C_6$alkyl or [-(p',q'—$C_2$-$C_6$alkylene)-Z-]$_{n'}$-$C_1$-$C_6$alkyl, n' being a number from 1 to 1000, p' and q' being different position numbers, each Z independently of any others being a hetero atom oxygen, sulfur or $C_1$-$C_{12}$alkyl-substituted nitrogen, and it being possible for $C_2$-$C_6$alkylene in the repeating [—$C_2$-$C_6$alkylene-Z—] units to be the same or different,
and $L_1$ and $L_2$ may be saturated or unsaturated from one to ten times, may be uninterrupted or interrupted at any location by from 1 to 10 groups selected from the group consisting of —(C═O)— and —$C_6H_4$—, and may carry no further substituents or from 1 to 10 further substituents selected from the group consisting of halogen, cyano and nitro. Most preferred L is a group of formula

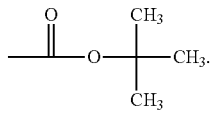

The disuccinates to be used in the process according to the invention include dialkyl, diaryl or monoalkyl-monoaryl succinates. The dialkyl and diaryl succinates may also be asymmetrical. However, it is preferred to use symmetrical disuccinates, most preferably symmetrical dialkyl succinates, most preferably symmetrical dialkyl succinates. If a diaryl or monoaryl-monoalkyl succinate is employed, aryl denotes preferably phenyl which is unsubstituted or substituted by halogen such as chlorine, $C_{1-6}$-alkyl such as ethyl, methyl, isopropyl or tert-butyl, or $C_{1-6}$-alkoxy such as methoxy or ethoxy. The preferred meaning of aryl is unsubstituted phenyl. If a dialkyl or monoalkyl-monoaryl succinate is employed, then alkyl may be unbranched or branched, preferably branched, and may contain preferably 1 to 18, in particular 1 to 12, more particularly 1 to 8 and more preferably 1 to 5, carbon atoms. Branched alkyl is preferably sec- or tert-alkyl, for example, isopropyl, sec-butyl, tert-butyl, tert-amyl and cyclohexyl.

Examples of disuccinates are dimethyl succinate, diethyl succinate, dipropyl succinate, dibutyl succinate, dipentyl succinate, dihexyl succinate, diheptyl succinate, dioctyl succinate, diisopropyl succinate, di-sec-butyl succinate, di-tert-butyl succinate, di-tert-amyl succinate, di-[1,1-dimethylbutyl]succinate, di-[1,1,3,3-tetramethylbutyl]succinate, di-[1,1dimethylpentyl]succinate, di-[1-methylethylbutyl]succinate, di-[1,1-diethylpropyl]succinate, diphenyl succinate, di-[4-methylphenyl]succinate, di-[4-chlorophenyl]succinate, monoethyl-monophenyl succinate, and dicyclohexyl succinate. Most preferably, the starting disuccinate is diisopropyl succinate.

The disuccinates are known compounds and may be prepared by known methods.

Typically, the nitriles and the disuccinate are used in stoichiometric proportions. It can be advantageous to use the nitriles to be reacted with the disuccinate in more than only stoichiometric proportions. An excess of disuccinate over the nitrile can often have a positive influence on the yield, in which case the excess may be up to twice the stoichiometrically required amount of disuccinate.

The reaction of the disuccinate with the nitriles is carried out in an organic solvent. Examples of suitable solvents are primary, secondary or tertiary alcohols containing 1 to 10 carbon atoms, for example, methanol, ethanol, n-propanol, isopropanol, n-butanol, sec-butanol, tert-butanol, n-pentanol, 2-methyl-2-butanol, 2-methyl-2-pentanol, 3-methyl-3-pentanol, 2-methyl-2-hexanol, 3-ethyl-3-pentanol, 2,4,4-trimethyl-2-pentanol, or glycols such as ethylene glycol or diethylene glycol; and also ethers such as tetrahydrofuran or dioxan, or glycol ethers such as ethylene glycol methyl ether, ethylene glycol ethyl ether, diethylene glycol monomethyl ether or diethylene glycol monoethyl ether; as well as dipolar aprotic solvents such as acetonitrile, benzonitrile, dimethylformamide, N,N-dimethylacetamide, nitrobenzene, N-methylpyrrolidone; aliphatic or aromatic hydrocarbons such as benzene or benzene substituted by alkyl, alkoxy or halogen, for example, toluene, xylene, anisole or chlorobenzene; or aromatic heterocyclic compounds such as pyridine, picoline or quinoline. Mixtures of the above solvents may also be used. It is convenient to use 5 to 20 parts be weight of solvent per 1 part by weight of reactants.

In the process according to the invention, it is preferred to use an alcohol as solvent, in particular a secondary or tertiary alcohol. Preferred tertiary alcohols are tert-butanol and tert-amyl alcohol. Mixtures of these preferred solvents with aromatic hydrocarbons such as toluene or xylene, or halogen-substituted benzene such as chlorobenzene, are also useful.

The process according to the invention is carried out in the presence of a strong base. Suitable strong bases are in particular the alkali metals themselves such as lithium, sodium or potassium, or alkali metal amides such as lithium amide, sodium amide or potassium amide, or alkali metal hydrides such as lithium, sodium or potassium hydride, or alkaline earth metal alcoholates or alkali metal alcoholates which are derived preferably from primary, secondary or tertiary aliphatic alcohols containing from 1 to 10 carbon atoms, for example, lithium methylate, sodium methylate or potassium methylate, or lithium, sodium or potassium ethylate, lithium, sodium or potassium n-propylate, lithium, sodium or potassium iso-propylate, lithium, sodium or potassium n-butylate, lithium, sodium or potassium sec-butylate, lithium, sodium or potassium tert-butylate, lithium, sodium or potassium 2-methyl-2-butylate, lithium, sodium or potassium 2-methyl-2-pentylate, lithium, sodium or potassium 3-methyl-3-pentylate, lithium, sodium or potassium 3-ethyl-3-pentylate or lithium, sodium or potassium 3-ethyl-3-pentylate. Additionally, a mixture of these bases may also be employed.

The preferred strong base is an alkali metal alcoholate, the alkali metals being preferably sodium or potassium and the alcoholate being preferably derived from a secondary or tertiary alcohol. Particularly preferred strong bases are therefore, for example, sodium or potassium isopropylate, sodium or potassium sec-butylate, sodium or potassium tert-butylate and sodium or potassium tert-amylate. Moreover, the alkali metal alcoholates may be prepared in situ by reacting the appropriate alcohol with the alkali metal, alkali metal hydride or alkali metal amide.

The strong base is employed in an amount of preferably from about 0.1 to about 10 moles, most preferably from about 1.9 to about 4.0 moles, based on one mole of the disuccinate. Although a stoichiometric amount of base may suffice, an excess of base has been found to have an advantageous effect on the yield.

Halogen is fluorine, chlorine, bromine and iodine.

$C_1$-$C_{25}$alkyl ($C_1$-$C_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3pentyl, 2,2-dimethylpropyl, 1,1,3,3-tetramethylpentyl, n-hexyl, 1-methylhexyl, 1,1,3,3,5,5hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl or pentacosyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl. A haloalkyl group is an alkyl group, wherein one, or more than one hydrogen atoms are repled by halogen atoms.

$C_2$-$C_{25}$alkenyl ($C_2$-$C_{18}$alkenyl) groups are straight-chain or branched alkenyl groups, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_{2-25}$alkynyl ($C_{2-18}$alkynyl) is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

Aliphatic groups can, in contrast to aliphatic hydrocarbon groups, be substituted by any acyclic substituents, but are preferably unsubstituted. Preferred substituents are $C_1$-$C_8$alkoxy or $C_1$-$C_8$alkylthio groups as exemplified further below. The term "aliphatic group" comprises also alkyl groups wherein certain non-adjacent carbon atoms are replaced by oxygen, like —$CH_2$—O—$CH_2$—$CH_2$—O—$CH_3$. The latter group can be regarded as methyl substituted by —O—$CH_2$—$CH_2$—O—$CH_3$.

An aliphatic hydrocarbon group having up to 25 carbon atoms is a linear or branched alkyl, alkenyl or alkynyl (also spelled alkinyl) group having up to 25 carbon atoms as exemplified above.

Alkylene is bivalent alkyl, i.e. alkyl having two (instead of one) free valencies, e.g. trimethylene or tetramethylene.

Alkenylene is bivalent alkenyl, i.e. alkenyl having two (instead of one) free valencies, e.g. —$CH_2$—CH=CH—$CH_2$—.

Aliphatic groups can, in contrast to aliphatic hydrocarbon groups, be substituted by any acyclic substituents, but are preferably unsubstituted. Preferred substituents are $C_1$-$C_8$alkoxy or $C_1$-$C_8$alkylthio groups as exemplified further below. The term "aliphatic group" comprises also alkyl groups wherein certain non-adjacent carbon atoms are replaced by oxygen, like —$CH_2$—O—$CH_2$—$CH_2$—O—$CH_3$. The latter group can be regarded as methyl substituted by —O—$CH_2$—$CH_2$—O—$CH_3$.

A cycloaliphatic hydrocarbon group is a cycloalkyl or cycloalkenyl group which may be substituted by one or more aliphatic and/or cycloaliphatic hydrocarbon groups.

A cycloaliphatic-aliphatic group is an aliphatic group substituted by a cycloaliphatic group, wherein the terms "cycloaliphatic" and "aliphatic" have the meanings given herein and wherein the free valency extends from the aliphatic moiety. Hence, a cycloaliphatic-aliphatic group is for example a cycloalkyl-alkyl group.

A cycloalkyl-alkyl group is an alkyl group substituted by a cycloalkyl group, e.g. cyclohexyl-methyl.

A "cycloalkenyl group" means an unsaturated alicyclic hydrocarbon group containing one or more double bonds, such as cyclopentenyl, cyclopentadienyl, cyclohexenyl and the like, which may be unsubstituted or substituted by one or more aliphatic and/or cycloaliphatic hydrocarbon groups and/or condensed with phenyl groups.

A bivalent group of the formula

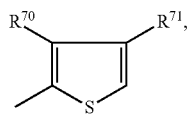

wherein $R^{70}$ and $R^{71}$ together represent alkylene or alkenylene which may be both bonded via oxygen and/or sulfur to the thienyl residue and which may both have up to 25 carbon atoms, is e.g. a group of the formula

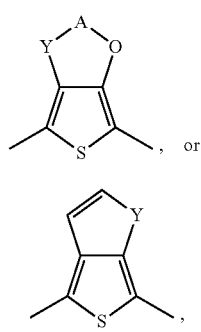

wherein A represents linear or branched alkylene having up to 25 carbon atoms, preferably ethylene or propylene which may be substituted by one or more alkyl groups, and Y represents oxygen or sulphur. For example, the bivalent group of the formula —Y-A-O— represents —O—$CH_2$—$CH_2$—O— or —O—$CH_2$—$CH_2$—$CH_2$—O—.

$C_1$-$C_{25}$alkoxy groups ($C_1$-$C_{18}$alkoxy groups) are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, preferably $C_1$-$C_4$alkoxy such as typically methoxy, ethoxy, n-propoxy, isopropoxy, n-butoxy, sec.-butoxy, isobutoxy, tert.-butoxy. The term "alkylthio group" means the same groups as the alkoxy groups, except that the oxygen atom of the ether linkage is replaced by a sulfur atom.

$C_1$-$C_{18}$perfluoroalkyl, especially $C_1$-$C_4$perfluoroalkyl, is a branched or unbranched radical such as for example —$CF_3$, —$CF_2CF_3$, —$CF_2CF_2CF_3$, —$CF(CF_3)_2$, —$(CF_2)_3CF_3$, and —$C(CF_3)_3$.

The term "carbamoyl group" is typically a $C_{1-18}$carbamoyl radical, preferably $C_{18}$ carbamoyl radical, which may be unsubstituted or substituted, such as, for example, carbamoyl, methylcarbamoyl, ethylcarbamoyl, n-butylcarbamoyl, tert-butylcarbamoyl, dimethylcarbamoyloxy, morpholinocarbamoyl or pyrrolidinocarbamoyl.

The term "alkanoyl" represents an alkyl group attached to the parent molecular group through a carbonyl group and is exemplified by formyl, acetyl, propionyl, and butanoyl.

The term "silyl group" means a group of formula —$SiR^{62}R^{63}R^{64}$, wherein $R^{62}$, $R^{63}$ and $R^{64}$ are independently of each other a $C_1$-$C_8$alkyl group, in particular a $C_1$-$C_4$ alkyl group, a $C_6$-$C_{24}$aryl group, or a $C_7$-$C_{12}$aralkylgroup, such as a trimethylsilyl group. The term "siloxanyl group" means a group of formula —O—$SiR^{62}R^{63}R^{64}$, wherein $R^{62}$, $R^{63}$ and $R^{64}$ are as defined above, such as a trimethylsiloxanyl group.

A cycloalkyl group is typically $C_3$-$C_{12}$cycloalkyl, such as, for example, cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted. The cycloalkyl group, or cycloalkenyl group, in particular a cyclohexyl group, can be condensed one or two times by phenyl which can be substituted one to three times with $C_1$-$C_4$-alkyl, halogen and cyano. Examples of such condensed cyclohexyl groups are:

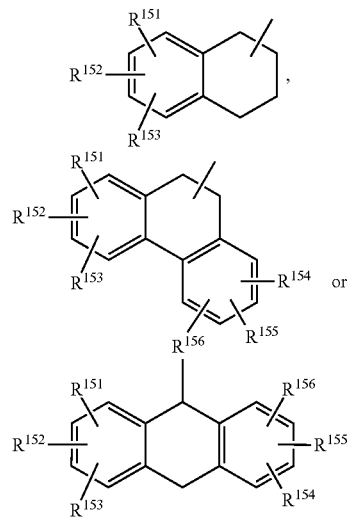

in particular

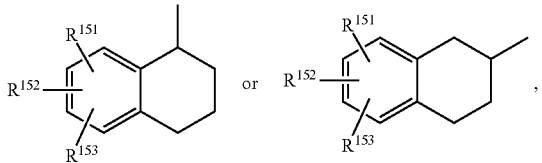

wherein $R^{151}$, $R^{152}$, $R^{153}$, $R^{154}$, $R^{155}$ and $R^{156}$ are independently of each other $C_1$-$C_8$-alkyl, $C_1$-$C_8$-alkoxy, halogen and cyano, in particular hydrogen.

$C_6$-$C_{24}$aryl ($C_6$-$C_{18}$aryl) is typically phenyl, indenyl, azulenyl, naphthyl, biphenyl, as-indacenyl, s-indacenyl, acenaphthylenyl, fluorenyl, phenanthryl, fluoranthenyl, triphenlenyl, chrysenyl, naphthacen, picenyl, perylenyl, pentaphenyl, hexacenyl, pyrenyl, or anthracenyl, preferably phenyl, 1-naphthyl, 2-naphthyl, 4-biphenyl, 9-phenanthryl, 2- or 9-fluorenyl, 3- or 4-biphenyl, which may be unsubstituted or substituted. Examples of $C_6$-$C_{12}$aryl are phenyl, 1-naphthyl, 2-naphthyl, 3- or 4-biphenyl, 2- or 9-fluorenyl or 9-phenanthryl, which may be unsubstituted or substituted.

$C_7$-$C_{25}$aralkyl is typically benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$-$C_{18}$aralkyl such as benzyl, 2-benzyl-2-propyl, β-phenyl-ethyl, α,α-dimethylbenzyl, ω-phenyl-butyl, ω,ω-dimethyl- ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted. Preferred examples are benzyl, 2-phenylethyl, β-phenylpropyl, naphthylethyl, naphthylmethyl, and cumyl.

Heteroaryl is typically $C_2$-$C_{20}$heteroaryl, i.e. a ring with five to seven ring atoms or a condensed ring system, wherein nitrogen, oxygen or sulfur are the possible hetero atoms, and is typically an unsaturated heterocyclic group with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl or phenoxazinyl, which can be unsubstituted or substituted.

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, a carbamoyl group, a nitro group or a silyl group, especially $C_1$-$C_8$alkyl, $C_1$-$C_8$alkoxy, $C_1$-$C_8$alkylthio, halogen, halo-$C_1$-$C_8$alkyl, or a cyano group.

$C_1$-$C_{25}$alkyl ($C_1$-$C_{18}$alkyl) interrupted by one or more O is, for example, $(CH_2CH_2O)_{1-9}R^{44}$, where $R^{44}$ is H or $C_1$-$C_{10}$alkyl, $CH_2$—$CH(OR^{y'})$—$CH_2$—O—$R^y$, where $R^y$ is $C_1$-$C_{25}$alkyl ($C_1$-$C_{18}$alkyl), and $R^{y'}$ embraces the same definitions as $R^y$ or is H.

If a substituent, such as, for example $R^3$, occurs more than one time in a group, it can be different in each occurrence.

Advantageously, the compounds of the present invention, or an organic semiconductor material, layer or component, comprising the compounds of the present invention can be used in organic photovoltaics (solar cells) and photodiodes, or in an organic field effect transistor (OFET).

The compounds of the formula I can show p-type transistor behavior and can be used as the semiconductor layer in semiconductor devices. Accordingly, the present invention also relates to a semiconductor device comprising as a semiconducting effective means a compound of the formula I.

The invention relates especially to a semiconductor device comprising as a semiconducting effective means a compound of the formula I described in the Examples selected from the compounds having the formulae A-1 to A-22, B-1 and B-2, respectively, which are depicted in claim 10.

Preferably said semiconductor device is a diode, a photodiode, a sensor, an organic field effect transistor (OFET), a transistor for flexible displays, or a solar cell, or a device containing a diode and/or an organic field effect transistor, and/or a solar cell. There are numerous types of semiconductor devices. Common to all is the presence of one or more semiconductor materials. Semiconductor devices have been described, for example, by S. M. Sze in Physics of Semiconductor Devices, $2^{nd}$ edition, John Wiley and Sons, New York (1981). Such devices include rectifiers, transistors (of which there are many types, including p-n-p, n-p-n, and thin-film transistors), light emitting semiconductor devices (for example, organic light emitting diodes in display applications or backlight in e.g. liquid crystal displays), photoconductors, current limiters, solar cells, thermistors, p-n junctions, field-effect diodes, Schottky diodes, and so forth. In each semiconductor device, the semiconductor material is combined with one or more metals and/or insulators to form the device. Semiconductor devices can be prepared or manufactured by known methods such as, for example, those described by Peter Van Zant in Microchip Fabrication, Fourth Edition, McGraw-Hill, New York (2000). In particular, organic electronic components can be manufactured as described by D. R. Gamota et al. in Printed Organic and Molecular Electronics, Kluver Academic Publ., Boston, 2004.

A particularly useful type of transistor device, the thin-film transistor (TFT), generally includes a gate electrode, a gate dielectric on the gate electrode, a source electrode and a drain electrode adjacent to the gate dielectric, and a semiconductor layer adjacent to the gate dielectric and adjacent to the source and drain electrodes (see, for example, S. M. Sze, Physics of Semiconductor Devices, $2^{nd}$ edition, John Wiley and Sons, page 492, New York (1981)). These components can be assembled in a variety of configurations. More specifically, an organic thin-film transistor (OTFT) has an organic semiconductor layer.

Typically, a substrate supports the OTFT during manufacturing, testing, and/or use. Optionally, the substrate can provide an electrical function for the OTFT. Useful substrate materials include organic and inorganic materials. For example, the substrate can comprise silicon materials inclusive of various appropriate forms of silicon, inorganic glasses, ceramic foils, polymeric materials (for example, acrylics, polyester, epoxies, polyamides, polycarbonates, polyimides, polyketones, poly(oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly (ethylene terephthalate) (PET), poly(phenylene sulfide) (PPS)), filled polymeric materials (for example, fiber-reinforced plastics (FRP)), and coated metallic foils. The substrate can have any suitable thickness, preferably in the range of 100 m to 10 mm, even more preferably from 10 □m to 1 mm.

The gate electrode can be any useful conductive material. For example, the gate electrode can comprise doped silicon, or a metal, such as aluminum, chromium, gold, silver, nickel, palladium, platinum, tantalum, and titanium. Conductive oxides, such as indium tin oxide (ITO), or conducting inks/pastes comprised of carbon black/graphite or colloidal silver dispersions, optionally containing polymer binders can also be used. Conductive polymers also can be used, for example polyaniline or poly(3,4-ethylenedioxythiophene)/poly(styrene sulfonate) (PEDOT:PSS). In addition, alloys, combinations, and multilayers of these materials can be useful. In some OTFTs, the same material can provide the gate electrode function and also provide the support function of the substrate. For example, doped silicon can function as the gate electrode and support the OTFT.

The gate dielectric is generally provided on the gate electrode. This gate dielectric electrically insulates the gate electrode from the balance of the OTFT device. Useful materials for the gate dielectric can comprise, for example, an inorganic electrically insulating material.

The gate dielectric (insulator) can be a material, such as, an oxide, nitride, or it can be a material selected from the family of ferroelectric insulators (e.g. organic materials such as poly (vinylidene fluoride/trifluoroethylene or poly(m-xylylene adipamide)), or it can be an organic polymeric insulator (e.g. poly(methacrylate)s, poly(acrylate)s, polyimides, benzocyclobutenes (BCBs), parylenes, polyvinylalcohol, polyvinylphenol (PVP), polystyrenes, polyester, polycarbonates) as for example described in J. Veres et al. Chem. Mat. 2004, 16, 4543 or A. Facchetti et al. Adv. Mat. 2005, 17, 1705. Specific examples of materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulphide, including but not limited to $PbZr_xTi_{1-x}O_3$ (PZT), $Bi_4Ti_3O_{12}$, $BaMgF_4$, $Ba(Zr_{1-x}Ti_x)O_3$ (BZT). In addition, alloys, hybride materials (e.g. polysiloxanes or nanoparticle-filled polymers) combinations, and multilayers of these materials can be used for the gate dielectric. The thickness of the dielectric layer is, for example, from about 10 to 1000 nm, with a more specific thickness being about 100 to 500 nm, providing a capacitance in the range of 0.1-100 nanofarads (nF).

The source electrode and drain electrode are separated from the gate electrode by the gate dielectric, while the organic semiconductor layer can be over or under the source electrode and drain electrode. The source and drain electrodes can be any useful conductive material favourably providing a low resistance ohmic contact to the semiconductor layer. Useful materials include most of those materials described above for the gate electrode, for example, aluminum, barium, calcium, chromium, gold, silver, nickel, palladium, platinum, titanium, polyaniline, PEDOT:PSS, other conducting polymers, alloys thereof, combinations thereof, and multilayers thereof. Some of these materials are appropriate for use with n-type semiconductor materials and others are appropriate for use with p-type semiconductor materials, as is known in the art.

The thin film electrodes (that is, the gate electrode, the source electrode, and the drain electrode) can be provided by any useful means such as physical vapor deposition (for example, thermal evaporation or sputtering) or (ink jet) printing methods. The patterning of these electrodes can be accomplished by known methods such as shadow masking, additive photolithography, subtractive photolithography, printing, microcontact printing, and pattern coating.

The present invention further provides a thin film transistor device comprising a plurality of electrically conducting gate electrodes disposed on a substrate; a gate insulator layer disposed on said electrically conducting gate electrodes; a plurality of sets of electrically conductive source and drain electrodes disposed on said insulator layer such that each of said sets is in alignment with each of said gate electrodes; an organic semiconductor layer disposed in the channel between source and drain electrodes on said insulator layer substantially overlapping said gate electrodes; wherein said organic semiconductor layer comprise a compound of the formula I.

The present invention further provides a process for preparing a thin film transistor device comprising the steps of:
depositing a plurality of electrically conducting gate electrodes on a substrate;
depositing a gate insulator layer on said electrically conducting gate electrodes;
depositing a plurality of sets of electrically conductive source and drain electrodes on said layer such that each of said sets is in alignment with each of said gate electrodes;
depositing a layer comprising a compound of the formula I on said insulator layer such that said layer comprising the compound of formula I substantially overlaps said gate electrodes, thereby producing the thin film transistor device.

The above-mentioned layer comprising a compound of formula I may additionally comprise at least another material. The other material can be, but is not restricted to another compound of the formula I, a semi-conducting polymer, a polymeric binder, organic small molecules different from a compound of the formula I, carbon nanotubes, a fullerene derivative, inorganic particles (quantum dots, quantum rods, quantum tripods, $TiO_2$, ZnO etc.), conductive particles (Au, Ag etc.), and insulator materials like the ones described for the gate dielectric (PET, PS etc.). As stated above, the semiconductive layer can also be composed of a mixture of one or more small molecules of the formula I and a polymeric binder. The ratio of the small molecules of formula I to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA). With this technique, a degradation of the electrical performance can be avoided (cf. WO 2008/001123 A1).

Any suitable substrate can be used to prepare the thin films of the compounds of the formula I. Preferably, the substrate used to prepare the above thin films is a metal, silicon, plastic, paper, coated paper, fabric, glass or coated glass.

Alternatively, a TFT is fabricated, for example, by solution deposition, or vacuum deposition of a compound of the formula I on a highly doped silicon substrate covered with a thermally grown oxide layer followed by vacuum deposition and patterning of source and drain electrodes.

In yet another approach, a TFT is fabricated by deposition of source and drain electrodes on a highly doped silicon substrate covered with a thermally grown oxide and then solution deposition of the compound of the formula I to form a thin film.

The gate electrode could also be a patterned metal gate electrode on a substrate or a conducting material such as a conducting polymer, which is then coated with an insulator applied either by solution coating or by vacuum deposition on the patterned gate electrodes.

Any suitable solvent can be used to dissolve, and/or disperse a compound of the formula I, provided it is inert and can be removed partly, or completely from the substrate by conventional drying means (e.g. application of heat, reduced pressure, airflow etc.). Suitable organic solvents for processing the semiconductors of the invention include, but are not limited to, aromatic or aliphatic hydrocarbons, halogenated such as chlorinated or fluorinated hydrocarbons, esters, ethers amides, such as chloroform, tetrachloroethane, tetrahydrofuran, toluene, tetraline, anisole, xylene, ethyl acetate, methyl ethyl ketone, dimethyl formamide, dichlorobenzene, trichlorobenzene, propylene glycol monomethyl ether acetate (PGMEA) and mixtures thereof. The solution, and/or dispersion is then applied by a method, such as, spin-coating, dip-coating, screen printing, microcontact printing, doctor blading or other solution application techniques known in the art on the substrate to obtain thin films of the semiconducting material.

The term "dispersion" covers any composition comprising a compound of the formula I, which is not fully dissolved in a solvent. The dispersion can be done selecting a composition including at least a compound of formula I, or a mixture containing a compound of formula I, and a solvent, wherein the polymer exhibits lower solubility in the solvent at room temperature but exhibits greater solubility in the solvent at an elevated temperature, wherein the composition gels when the elevated temperature is lowered to a first lower temperature without agitation;
dissolving at the elevated temperature at least a portion of the compound of the formula I in the solvent; lowering the temperature of the composition from the elevated temperature to the first lower temperature; agitating the composition to disrupt any gelling, wherein the agitating commences at any time prior to, simultaneous with, or subsequent to the lowering the elevated temperature of the composition to the first lower temperature; depositing a layer of the composition wherein the composition is at a second lower temperature lower than the elevated temperature; and drying at least partially the layer.

The dispersion can also be constituted of (a) a continuous phase comprising a solvent, a binder resin, and optionally a dispersing agent, and (b) a disperse phase comprising a compound of formula I, or a mixture containing a compound of formula I of the present invention. The degree of solubility of the compound of formula I in the solvent may vary for example from 0.5% to about 20% solubility, particularly from 1% to about 5% solubility.

Preferably, the thickness of the organic semiconductor layer is in the range of from about 5 to about 1000 nm, especially the thickness is in the range of from about 10 to about 100 nm.

The compounds of the formula I can be used alone or in combination as the organic semiconductor layer of the semiconductor device. The layer can be provided by any useful means, such as, for example, vapor deposition and printing techniques. The compounds of the formula I which are sufficiently soluble in organic solvents can be solution deposited and patterned (for example, by spin coating, dip coating, ink jet printing, gravure printing, flexo printing, offset printing, screen printing, microcontact (wave)-printing, drop or zone casting, or other known techniques).

The compounds of the formula I can be used in integrated circuits comprising a plurality of OTFTs, as well as in various electronic articles. Such articles include, for example, radiofrequency identification (RFID) tags, backplanes for flexible displays (for use in, for example, personal computers, cell phones, or handheld devices), smart cards, memory devices, sensors (e.g. light-, image-, bio-, chemo-, mechanical- or temperature sensors), especially photodiodes, or security devices and the like. Due to its ambi-polarity the material can also be used in Organic Light Emitting Transistors (OLET).

In addition, the invention provides organic photovoltaic (PV) devices (solar cells) comprising a compound of the formula I. The structure of organic photovoltaic devices (solar cells) is, for example, described in C. Deibel et al. Rep. Prog. Phys. 73 (2010) 096401 and Christoph Brabec, Energy Environ. Sci 2. (2009) 347-303.

The PV device comprise in this order:
(a) a cathode (electrode),
(b) optionally a transition layer, such as an alkali halogenide, especially lithium fluoride,
(c) a photoactive layer,
(d) optionally a smoothing layer,
(e) an anode (electrode),
(f) a substrate.

The photoactive layer comprises the compounds of the formula I. Preferably, the photoactive layer is made of a compound of the formula I, as an electron donor and an acceptor material, like a fullerene, particularly a functionalized fullerene PCBM, as an electron acceptor. As stated above, the photoactive layer may also contain a polymeric binder. The ratio of the small molecules of formula I to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA).

The fullerenes useful in this invention may have a broad range of sizes (number of carbon atoms per molecule). The term fullerene as used herein includes various cage-like molecules of pure carbon, including Buckminsterfullerene ($C_{60}$) and the related "spherical" fullerenes as well as carbon nanotubes. Fullerenes may be selected from those known in the art ranging from, for example, $C_{20}$-$C_{1000}$. Preferably, the fullerene is selected from the range of $C_{60}$ to $C_{96}$. Most preferably the fullerene is $C_{60}$ or $C_{70}$, such as [60]PCBM, or [70]PCBM. It is also permissible to utilize chemically modified fullerenes, provided that the modified fullerene retains acceptor-type and electron mobility characteristics. The acceptor material can also be a material selected from the group consisting of another compound of formula I or any semi-conducting polymer provided that the polymers retain acceptor-type and electron mobility characteristics, organic small molecules, carbon nanotubes, inorganic particles (quantum dots, quantum rods, quantum tripods, $TiO_2$, ZnO etc.).

For heterojunction solar cells (bulk heterojunction solar cells) the active layer comprises preferably a mixture of a compound of the formula I and a fullerene, such as [60] PCBM (=6,6-phenyl-$C_{61}$-butyric acid methyl ester), or [70] PCBM, in a weight ratio of 1:1 to 1:3. Methanofullerene Phenyl-$C_{61}$-Butyric-Acid-Methyl-Ester ([60]PCBM), i.e. 1-[3-(methoxycarbonyl)propyl]-1-phenyl-[6.6]$C_{61}$-3'H-cyclopropa[1,9][5,6]fullerene-$C_{60}$-lh-3'-butanoic acid 3'-phenyl methyl ester, is an effective solution processable n-type organic semiconductor. It is blended with conjugated polymers with nano-particles such as $C_{60}$.

The electrodes are preferably composed of metals or "metal substitutes". Herein the term "metal" is used to embrace both materials composed of an elementally pure metal, e.g., Mg, and also metal alloys which are materials composed of two or more elementally pure metals, e.g., Mg and Ag together, denoted Mg:Ag. Here, the term "metal substitute" refers to a material that is not a metal within the normal definition, but which has the metal-like properties that are desired in certain appropriate applications. Commonly used metal substitutes for electrodes and charge transfer layers would include doped wide-bandgap semiconductors, for example, transparent conducting oxides such as indium tin oxide (ITO), gallium indium tin oxide (GITO), and zinc indium tin oxide (ZITO). Another suitable metal substitute is the transparent conductive polymer polyanaline (PANI) and its chemical relatives, or PEDOT:PSS. Metal substitutes may be further selected from a wide range of non-metallic materials, wherein the term "non-metallic" is meant to embrace a wide range of materials provided that the material is free of metal in its chemically uncombined form.

Highly transparent, non-metallic, low resistance cathodes or highly efficient, low resistance metallic/non-metallic compound cathodes are, for example, disclosed in U.S. Pat. No. 6,420,031 and U.S. Pat. No. 5,703,436.

The substrate can be, for example, a plastic (flexible substrate), or glass substrate.

In another preferred embodiment of the invention, a smoothing layer is situated between the anode and the photoactive layer. A preferred material for this smoothing layer comprises a film of 3,4-polyethylenedioxythiophene (PEDOT), or 3,4-polyethylenedioxy-thiophene:polystyrene-sulfonate (PEDOT:PSS).

In a preferred embodiment of the present invention, the photovoltaic cell comprises, as described for example, in U.S. Pat. No. 6,933,436 a transparent glass carrier, onto which an electrode layer made of indium/tin oxide (ITO) is applied. This electrode layer generally has a comparatively rough surface structure, so that it is covered with a smoothing layer made of a polymer, typically PEDOT, which is made electrically conductive through doping. The photoactive layer is made of two components, has a layer thickness of, for example, 100 nm to a few μm depending on the application method, and is applied onto this smoothing layer. The photoactive layer is made of a compound of the formula I, as an electron donor and a fullerene, particularly functionalized fullerene PCBM, as an electron acceptor. These two components are mixed with a solvent and applied as a solution onto the smoothing layer by, for example, the spin-coating method, the drop casting method, the Langmuir-Blodgett ("LB") method, the ink jet printing method and the dripping method. A squeegee or printing method could also be used to coat larger surfaces with such a photoactive layer. Instead of toluene, which is typical, a dispersion agent such as chlorobenzene is preferably used as a solvent. Among these methods, the vacuum deposition method, the spin-coating method, the ink jet printing method and the casting method are particularly preferred in view of ease of operation and cost.

In the case of forming the layer by using the spin-coating method, the casting method and ink jet printing method, the coating can be carried out using a solution and/or dispersion prepared by dissolving, or dispersing the composition in a concentration of from 0.01 to 90% by weight in an appropriate organic solvent such as benzene, toluene, xylene, tetrahydrofurane, methyltetrahydrofurane, N,N-dimethylformamide, acetone, acetonitrile, anisole, dichloromethane, dimethylsulfoxide, chlorobenzene, 1,2-dichlorobenzene and mixtures thereof.

Before a counter electrode is applied, a thin transition layer, which must be electrically insulating, having a layer thickness of, for example, 0.6 nm, is applied to the photoactive layer. In this exemplary embodiment, this transition layer is made of an alkali halogenide, namely a lithium fluoride, which is vapor deposited in a vacuum of $2 \cdot 10^{-6}$ torr at a rate of 0.2 nm/minute.

If ITO is used as a hole-collecting electrode, aluminum, which is vapor deposited onto the electrically insulating transition layer, is used as an electron-collecting electrode. The electric insulation properties of the transition layer obviously prevent influences which hinder the crossing of the charge carrier from being effective, particularly in the transition region from the photoactive layer to the transition layer.

In a further embodiment of the invention, one or more of the layers may be treated with plasma prior to depositing the next layer. It is particularly advantageous that prior to the deposition of the PEDOT:PSS layer the anode material is subjected to a mild plasma treatment.

As an alternative to PEDOT:PSS a crosslinkable hole-transport material based on triarylamines as referenced in Macromol. Rapid Commun. 20, 224-228 (1999) can be used. In addition to the triarylamine material the layer can also include an electron acceptor to improve electron transport. Such compounds are disclosed in US 2004/0004433. Preferably, the electron acceptor material is soluble in one or more organic solvents. Typically, the electron acceptor material is present in the range of 0.5 to 20% by weight of the triarylamine material.

The photovoltaic (PV) device can also consist of multiple junction solar cells that are processed on top of each other in order to absorb more of the solar spectrum. Such structures are, for example, described in App. Phys. Let. 90, 143512 (2007), Adv. Funct. Mater. 16, 1897-1903 (2006) and WO2004/112161 and Christoph Brabec, Energy Environ. Sci 2. (2009) 347-303.

A so called 'tandem solar cell' comprise in this order:
(a) a cathode (electrode),
(b) optionally a transition layer, such as an alkali halogenide, especially lithium fluoride,
(c) a photoactive layer,
(d) optionally a smoothing layer,
(e) a middle electrode (such as Au, Al, ZnO, TiO$_2$ etc.)
(f) optionally an extra electrode to match the energy level,
(g) optionally a transition layer, such as an alkali halogenide, especially lithium fluoride,
(h) a photoactive layer,
(i) optionally a smoothing layer,
(j) an anode (electrode),
(k) a substrate.

The PV device can also be processed on a fiber as described, for example, in US20070079867 and US 20060013549.

Due to their excellent self-organising properties the materials or films comprising the compounds of the formula I can also be used alone or together with other materials in or as alignment layers in LCD or OLED devices, as described for example in US2003/0021913.

Various features and aspects of the present invention are illustrated further in the examples that follow. While these examples are presented to show one skilled in the art how to operate within the scope of this invention, they are not to serve as a limitation on the scope of the invention where such scope is only defined in the claims. Unless otherwise indicated in the following examples and elsewhere in the specification and claims, all parts and percentages are by weight, temperatures are in degrees centigrade and pressures are at or near atmospheric.

EXAMPLES

Example 1

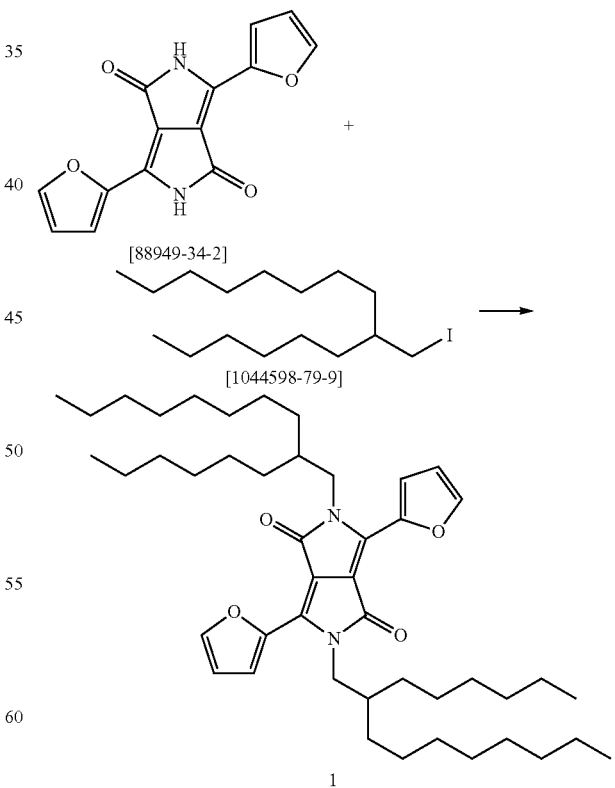

a) 20 g of [88949-34-2] and 25.76 g of potassium carbonate are suspended in 300 ml of dry dimethylformamide and the mixture is heated to 90° C. under nitrogen. Then 79 g of

[1044598-79-9] are added drop wise. The reaction mixture is then stirred for 6 h at 90° C. After cooling to room temperature ethylacetate is added and the mixture is washed with water. The organic phase is dried over magnesium sulfate and the solvent is evaporated. The product is purified by column chromatography over silica to obtain compound 1. $^1$H-NMR data (ppm, CDCl$_3$): 8.33 2H d, 7.60 2H d, 6.68 2H d×d, 4.03 4H d, 1.85-1.75 2H m, 1.45-1.15 48H m, 0.88 6H t, 0.86 6H t.

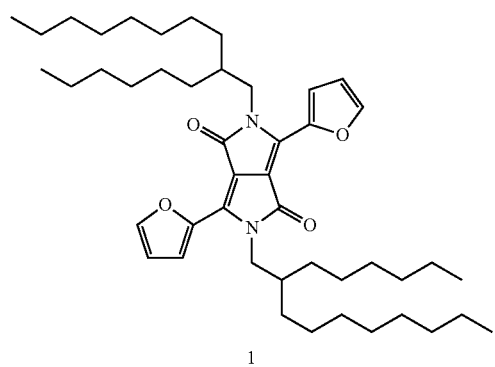

1

NBS →

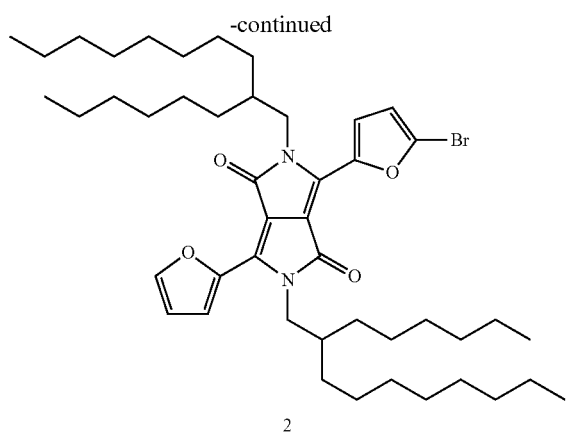

2 b) 26.30 g of compound 1 are dissolved in 300 ml of chloroform. The mixture is cooled to −10° C. and then 11.42 g of N-bromo-succinimid (NBS) are added and the mixture is stirred for 2 hours at −10° C. The reaction mixture is washed with water, dried with magnesium sulfate and the solvent is evaporated. The crude product is purified by column chromatography over silica to obtain compound 2. $^1$H-NMR data (ppm, CDCl$_3$): 8.35 1H d, 8.30 1H d, 7.62 1H d, 6.71 1H d×d, 6.62 1H d, 4.03 2H d, 4.00 2H d, 1.87-1.75 2H m, 1.45-1.20 48H m, 0.88 6H t, 0.86 6H t.

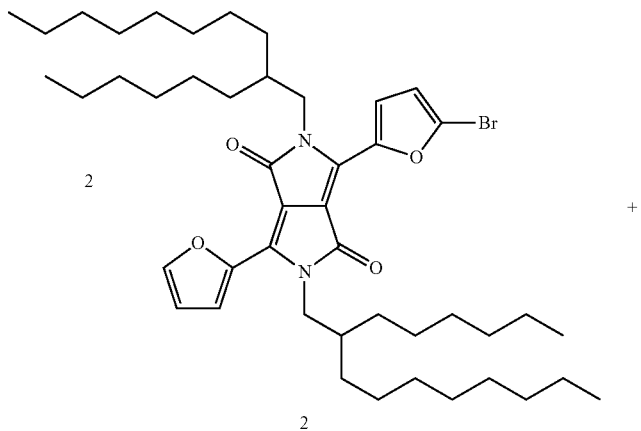

2

+

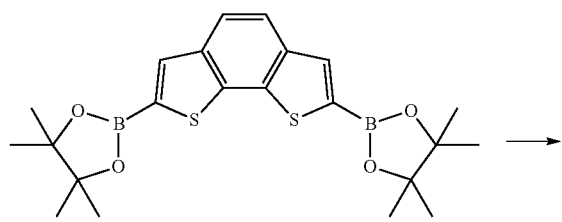

[1256165-36-2]

-continued

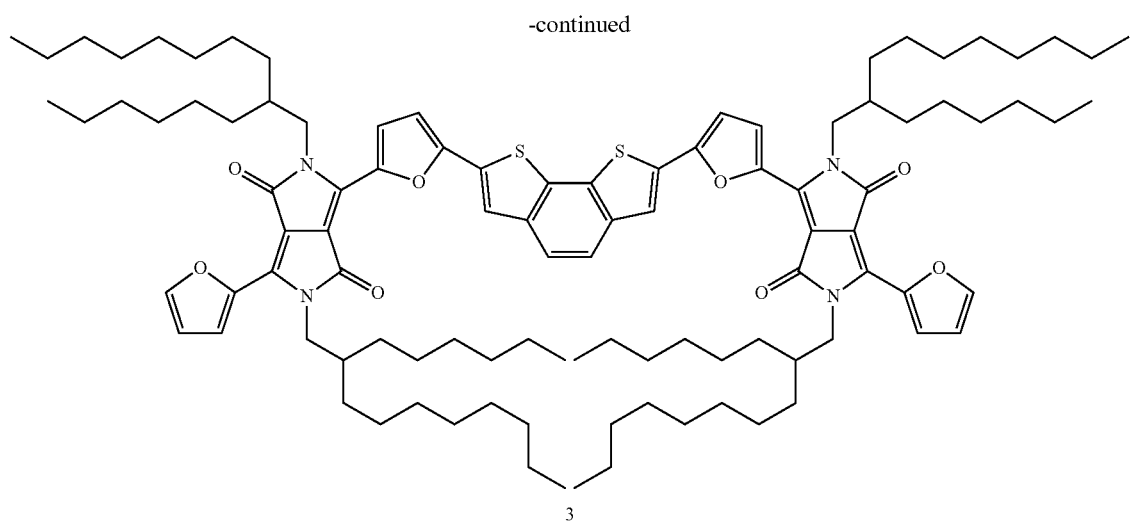

3 c) 232 mg of compound 2, 58 mg of compound [1256165-36-2], 2 mg of Pd(OAc)$_2$ and 25 mg of 2-(di-tert-butylphosphino)-1-phenylindole are placed into a reactor under Argon. Then 20 ml oxygen free THF are added and the reaction mixture is heated to 50° C. Then 37 mg of lithium hydroxide monohydrate are added and the reaction mixture is then heated for 2 hours at reflux temperature. The reaction mixture is poured on ice/water and then extracted with chloroform. The organic solution is dried over MgSO$_4$ and evaporated. Compound 3 is then obtained after column chromatography of the crude product. $^1$H-NMR data (ppm, CDCl$_3$): 8.46 2H d, 8.36 2H d, 7.71 2H s, 7.62 2H s, 7.59 2H d, 6.89 2H d, 6.70 2H d, 4.13 4H d, 4.03 4H d, 1.96 2H broad s, 1.83 2H broad s, 1.45-1.15 96H m, 0.89 12H t, 0.82 12H t.

Example 2

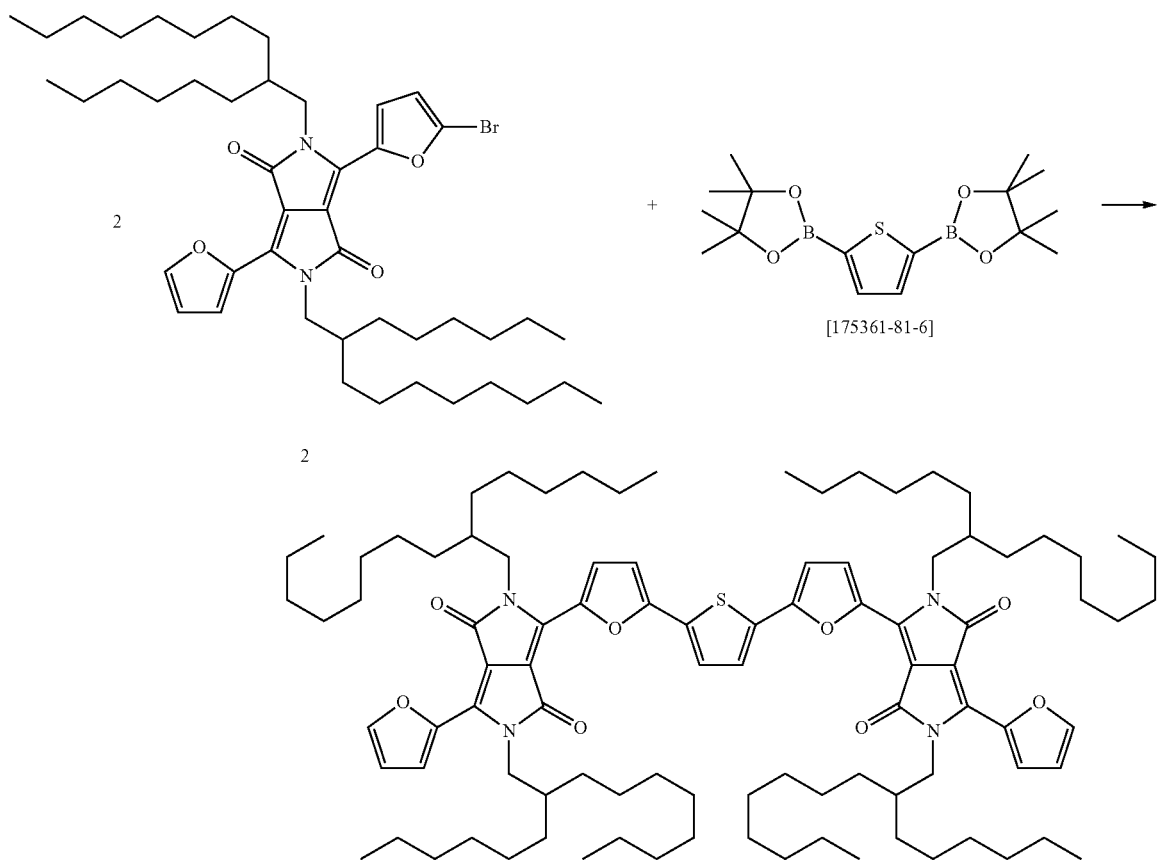

4

Two equivalents of compound 2 and 1 equivalent of compound [175361-81-6] are reacted according to the example 1 to obtain compound 4.
Example 3
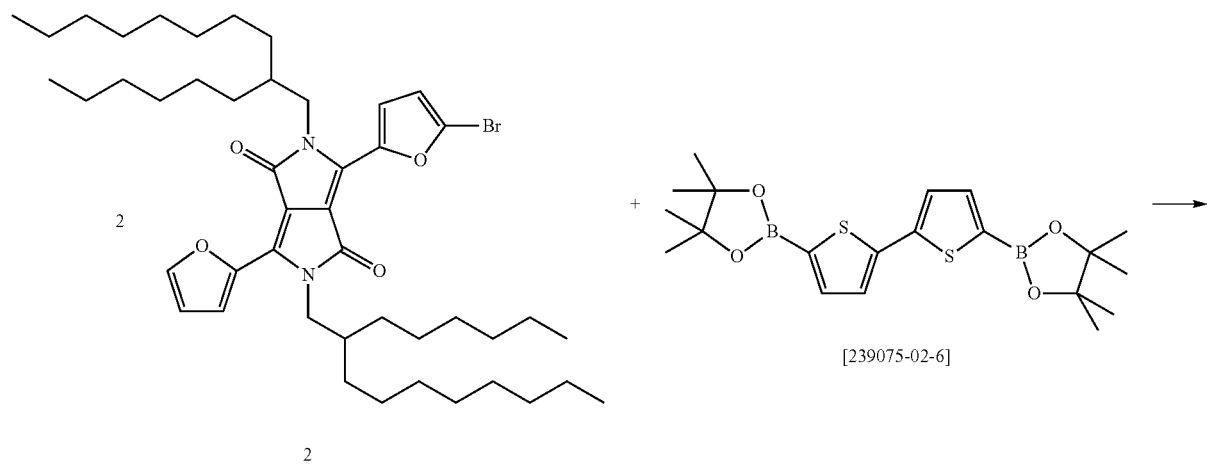
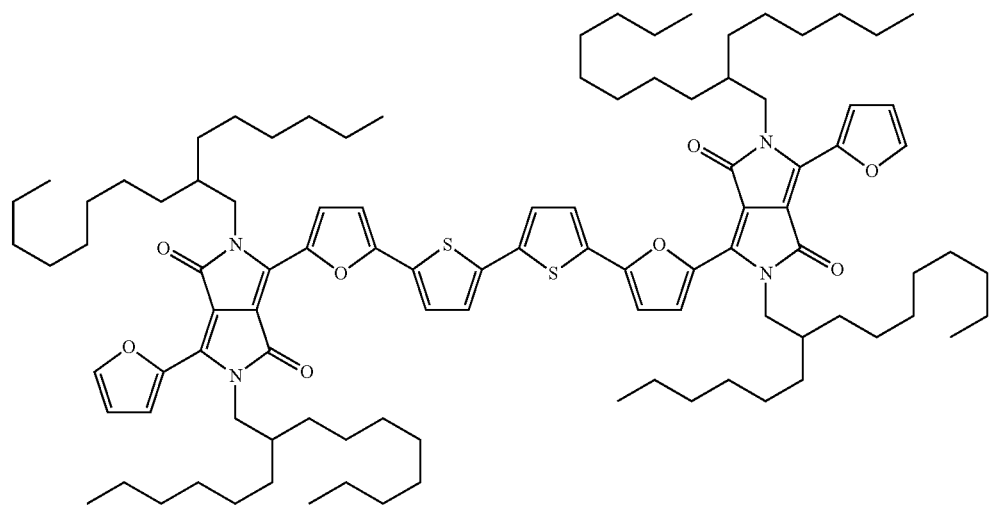

Two equivalents of compound 2 and 1 equivalent of compound [239075-02-6] are reacted according to the example 1 to obtain compound 5.
Example 4
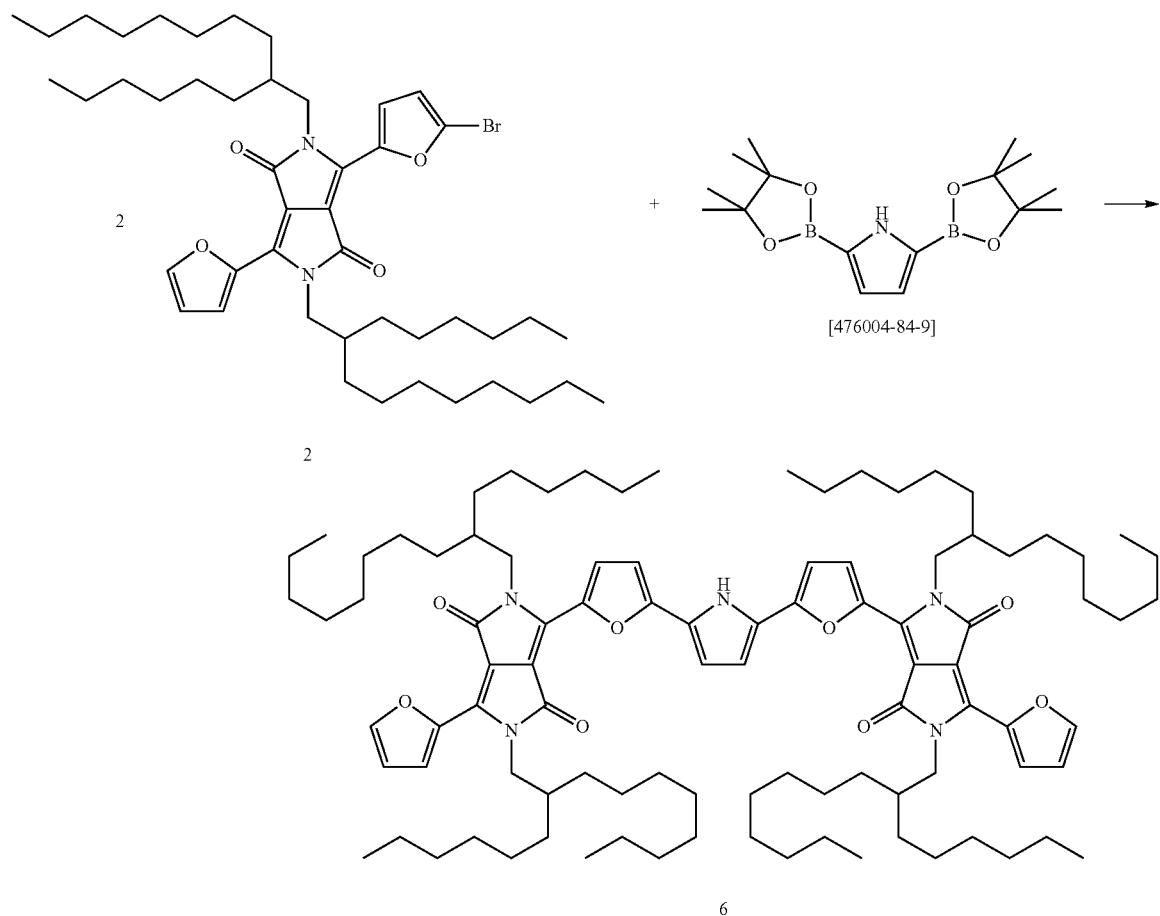
Two equivalents of compound 2 and 1 equivalent of compound [476004-84-9] are reacted according to the example 1 to obtain compound 6.
Example 5
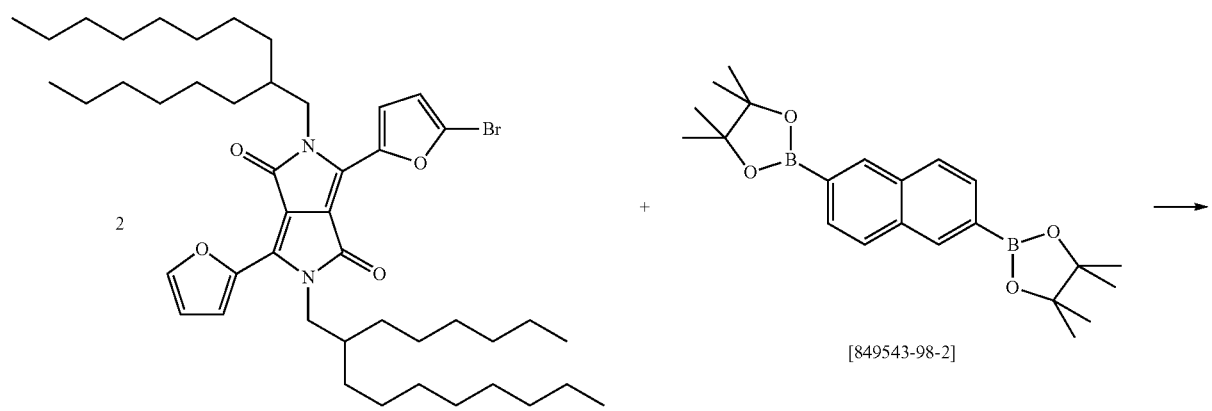

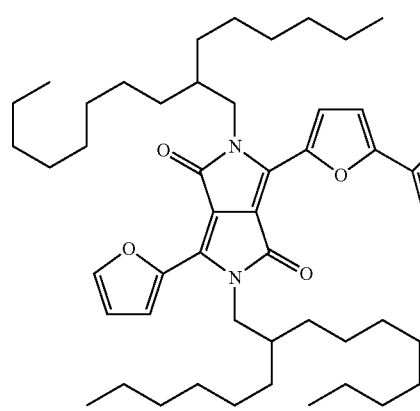
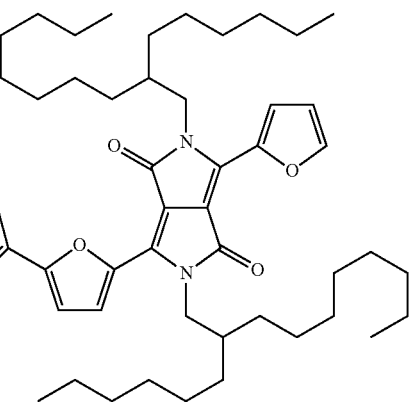

7

Two equivalents of compound 2 and 1 equivalent of compound [849543-98-2] are reacted according to the example 1 to obtain compound 7.

Application Example 1

Bottom Gate Bottom Contact (BGBC) Field-Effect Transistor (FET)

Standard procedure for transistors on silicon substrates: Heavily doped silicon wafers (Si n–(425±40 μm) with a 230 nm thick thermally grown silicon dioxide layer having on top of the silicon dioxide layer indium tin oxide (15 nm)/gold (30 nm) contacts are used as substrates. The substrates are prepared by standard cleaning in acetone and i-propanol followed by oxygen plasma treatment for 30 minutes and are then transferred in a glove box and treated with octyltrichlorosilane (OTS) to achieve a hydrophobic monolayer.

Deposition of Semiconductor Film:

The semiconductor, compound 3, is dissolved in toluene in a concentration of 0.75% by weight at elevated temperature and is spin-coated at 1500 rounds per minute (rpm) for 60 seconds onto the silicon dioxide/silicon substrate. All electrical measurements are performed under a nitrogen atmosphere in a glove box with a gate voltage (Vg) varying from 10 to –30 V and at a drain voltage (Vd) equal to 3 and 30V for the transfer characterisation. For the output characterization Vd is varied from 0 to –30V at Vg=0, 10, 20, 30 V. The measured mobilities represent the saturation mobilities at Vd=–30V.

The compound 3 has excellent solubility in organic solvents and excellent film-forming properties. The FET of Application Example 1, where the semiconductor layer consists of compound 3, shows p-type characteristics with excellent processability and reproducibility.

Application Example 2

Organic Bulk Heterojunction Solar Cell

The solar cell has the following structure: Al electrode/LiF layer/organic layer, comprising compound 3 and 1-[3-(methoxycarbonyl)propyl]-1-phenyl-[6.6]$C_{61}$ 3'H-cyclopropa[1,9][5,6]fullerene-$C_{60}$-lh-3'-butanoic acid 3'-phenyl methyl ester ([60]PCBM)/[poly(3,4-ethylenedioxy-thiophene) (PE-DOT) in admixture with poly(styrenesulfonic acid) (PSS)]/ITO electrode/glass substrate. The solar cells are made by spin coating a layer of the PEDOT-PSS on a pre-patterned ITO on glass substrate. Then a 1:2 mixture of the compound of the present invention (1% by weight):[60]PCBM (a substituted $C_{60}$ fullerene) is spin coated from chloroform. (organic layer). LiF and Al are sublimed under high vacuum through a shadow-mask.

Solar Cell Performance:

The solar cell is measured under Aescusoft solar light simulator with halogen light source. The current is estimated under AM1.5 conditions using the External Quantum Efficiency (EQE) graph.

The solar cell of Application Example 1, where the semiconductor layer consists of compound 3 and [60]PCBM, shows OPV characteristics with excellent processability and reproducibility.

The invention claimed is:

1. A compound of formula (I)

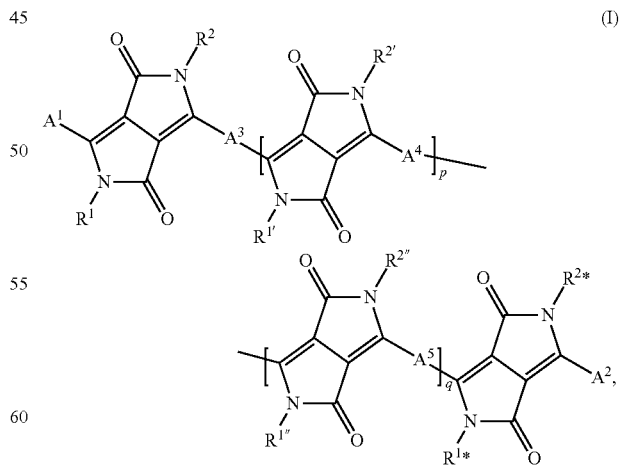

wherein p is 0, or 1, q is 0, or 1, $A^1$ and $A^2$ are independently of each other a group of formula

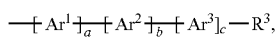

A³, A⁴ and A⁵ are independently of each other a group of formula

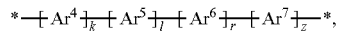

a is 1 or 2; b is 0, 1 or 2; c is 0, 1 or 2;
k is 0, 1, or 2; l is 1, 2, or 3; r is 0, or 1; z is 0, 1 or 2;
$R^1, R^2, R^{1'}, R^{2'}, R^{1''}, R^{2''}, R^{1*}$ and $R^{2*}$ may be the same or different and are a $C_1$-$C_{100}$ alkyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group or a siloxanyl group and/or can optionally be interrupted by —O—, —S—, —NR³⁹—, —COO—, —CO— or —OCO;
R³ is hydrogen,
Ar¹ is

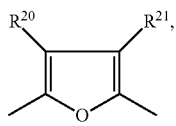

and Ar², Ar³, Ar⁴, Ar⁵, Ar⁶ and Ar⁷ are independently of each other a bivalent group of formula

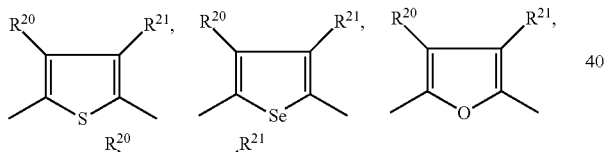

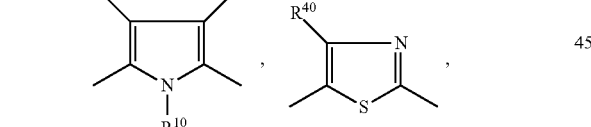

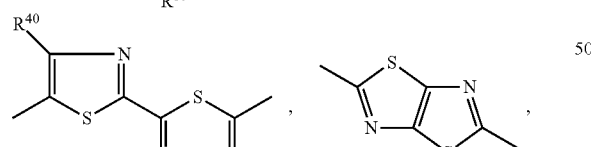

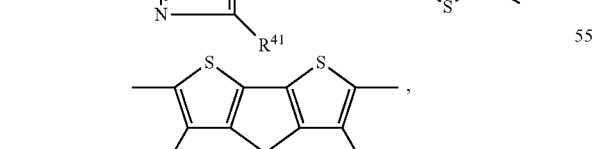

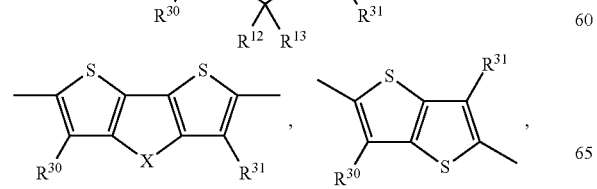

-continued

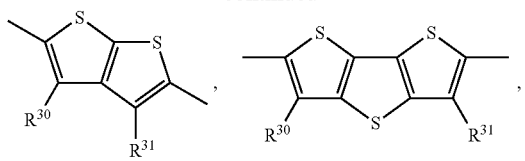

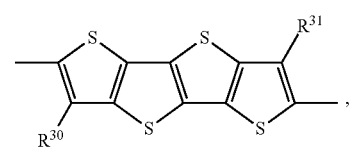

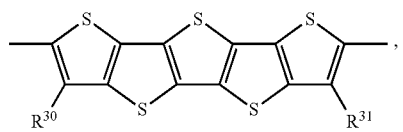

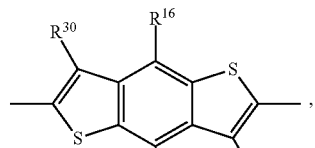

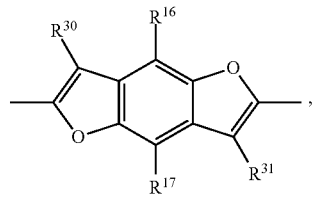

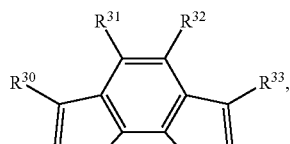

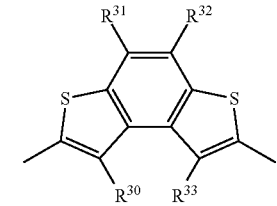

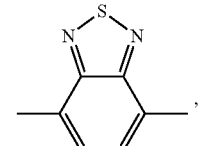

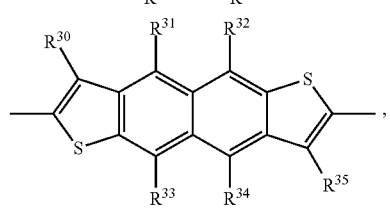

-continued

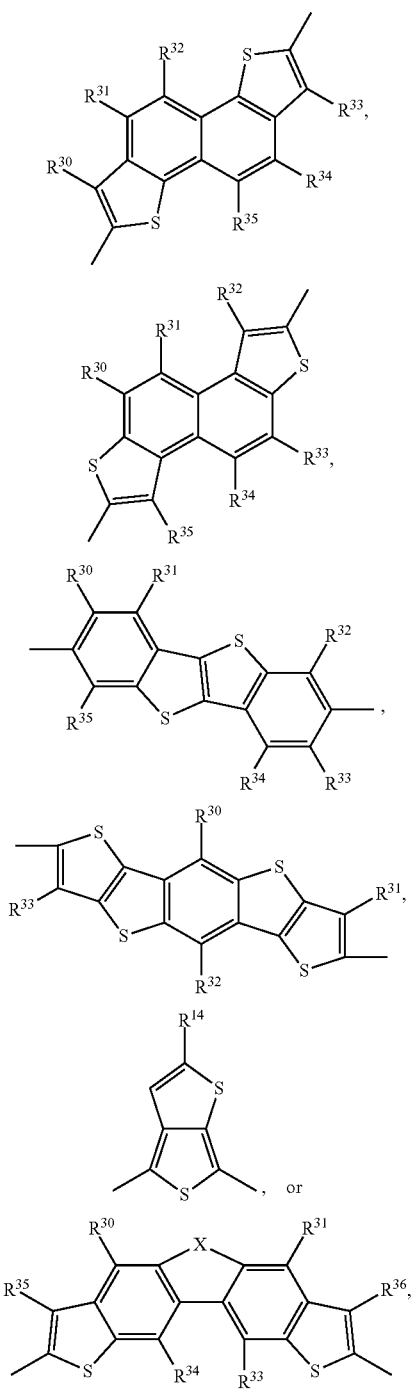

X is —O—, —S—, —NR$^{10}$—, —Si(R$^{18}$)(R$^{19}$)—, —Ge(R$^{18}$)(R$^{19}$)—, —C(R$^{12}$)(R$^{13}$)—, —C(=CR$^{14}$R$^{15}$),

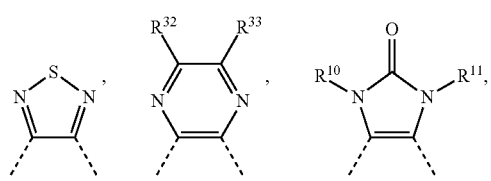

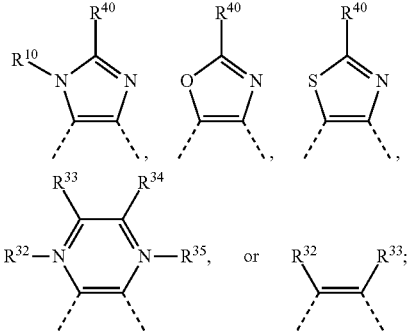

R$^{10}$ and R$^{11}$ are independently of each other hydrogen, C$_1$-C$_{18}$alkyl, C$_1$-C$_{18}$haloalkyl, C$_7$-C$_{25}$arylalkyl, or C$_1$-C$_{18}$alkanoyl, R$^{12}$ and R$^{13}$ are independently of each other hydrogen, C$_1$-C$_{18}$alkyl, C$_1$-C$_{18}$haloalkyl, C$_7$-C$_{25}$arylalkyl, C$_6$-C$_{24}$aryl, or C$_2$-C$_{20}$heteroaryl, or R$^{12}$ and R$^{13}$ together represent oxo,

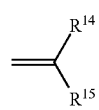

or form a five or six membered ring, which is unsubstituted or substituted by C$_1$-C$_{18}$alkyl and/or C$_1$-C$_{18}$alkoxy;

R$^{14}$ and R$^{15}$ are independently of each other hydrogen, C$_1$-C$_{18}$alkyl, C$_6$-C$_{24}$aryl, C$_2$-C$_{20}$heteroaryl, —CN or COOR$^{50}$;

R$^{16}$ and R$^{17}$ are independently of each other hydrogen, halogen, C$_1$-C$_{25}$alkyl, C$_1$-C$_{25}$alkoxy, C$_7$-C$_{25}$arylalkyl, or

R$^x$ is a C$_1$-C$_{12}$alkyl group, or a tri(C$_1$-C$_8$alkyl)silyl group,

R$^{18}$ and R$^{19}$ are independently of each other hydrogen, C$_1$-C$_{18}$alkyl, C$_7$-C$_{25}$arylalkyl, or a phenyl group, which optionally can be substituted one to three times with C$_1$-C$_8$alkyl and/or C$_1$-C$_8$alkoxy, R$^{20}$ and R$^{21}$ are independently of each other hydrogen, C$_1$-C$_{25}$alkyl, C$_2$-C$_{25}$alkenyl, C$_2$-C$_{25}$alkyl which is interrupted by one or more —O— or —S—, COOR$^{50}$, cyano, C$_1$-C$_{18}$alkoxy, C$_6$-C$_{24}$aryl, C$_7$-C$_{25}$arylalkyl, halogen or C$_2$-C$_{20}$heteroaryl, or R$^{20}$ and R$^{21}$ together represent alkylene or alkenylene which may be both bonded via oxygen and/or sulfur to the (hetero)aromatic residue and which may both have up to 4 carbon atoms, R$^{30}$ to R$^{37}$ are independently of each other hydrogen, C$_1$-C$_{25}$alkyl, C$_2$-C$_{25}$alkenyl, C$_2$-C$_{25}$alkyl which is interrupted by one or more —O— or —S—, COOR$^{50}$, cyano, C$_1$-C$_{25}$alkoxy, C$_6$-C$_{24}$aryl, C$_7$-C$_{25}$arylalkyl, halogen or C$_2$-C$_{20}$heteroaryl, R$^{40}$ and R$^{41}$ are independently of each other hydrogen, C$_1$-C$_{25}$alkyl, C$_2$-C$_{25}$alkenyl, C$_2$-C$_{25}$alkyl which is interrupted by one or more —O— or —S—, COOR$^{50}$, cyano, C$_1$-C$_{18}$alkoxy, C$_6$-C$_{24}$aryl, C$_7$-C$_{25}$arylalkyl, halogen or C$_2$-C$_{20}$heteroaryl, $R^{50}$ is $C_1$-$C_{25}$alkyl, $C_1$-$C_{25}$haloalkyl, $C_7$-$C_{25}$arylalkyl, $C_6$-$C_{24}$aryl or $C_2$-$C_{20}$heteroaryl;

$R^{60}$ to $R^{68}$ represent independently of each other H, halogen, cyano, $C_1$-$C_{25}$alkyl, $C_1$-$C_{25}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, a $C_4$-$C_{18}$cycloalkyl group, a $C_4$-$C_{18}$cycloalkyl group, which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or $C_7$-$C_{25}$aralkyl, which is substituted by G, $R^{70}$ and $R^{71}$ are independently of each other hydrogen, $C_1$-$C_{25}$alkyl, or $C_7$-$C_{25}$aralkyl, or $R^{70}$ and $R^{71}$ together represent alkylene or alkenylene which may be both bonded via oxygen and/or sulfur to the thienyl residue and which may both have up to 25 carbon atoms, D is —CO—, —COO—, —S—, —O—, —$NR^{39}$—, or —C(=O)$NR^{39}$—, E is $C_1$-$C_8$thioalkoxy, COO—$C_1$-$C_{18}$alkyl, $C_1$-$C_8$alkoxy, CN, —$NR^{39}R^{39'}$, —$CONR^{39}R^{39''}$, or halogen, G is E, or $C_1$-$C_{18}$alkyl, $R^{39}$ and $R^{39'}$ are independently of each other hydrogen, $C_1$-$C_{18}$alkyl, $C_1$-$C_{18}$haloalkyl, $C_7$-$C_{25}$arylalkyl, or $C_1$-$C_{18}$alkanoyl, with the proviso that $Ar^5$ is different from a group

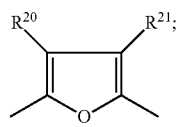

if q is 0, p is 0, k is 0, r is 0, z is 0 and l is 1.

2. The compound according to claim 1 of formula (Ia), (Ib) or (Ic)

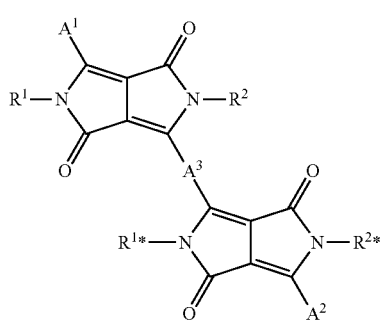

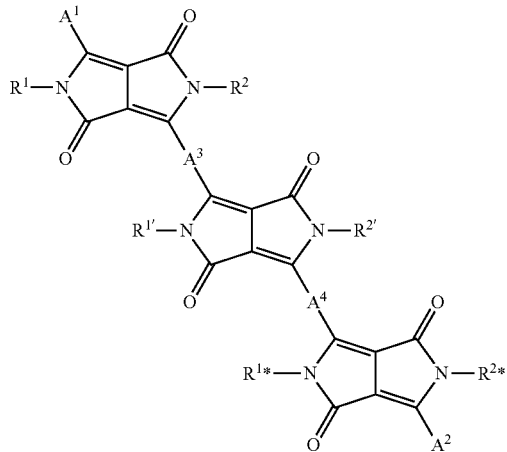

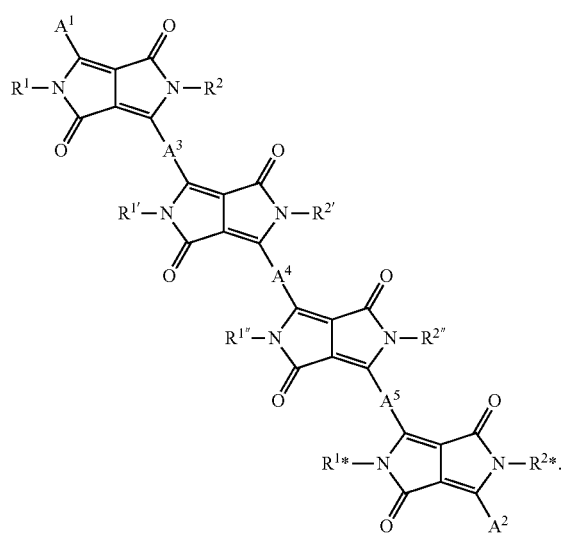

3. The compound according to claim 1, wherein $R^1$, $R^2$, $R^{1'}$, $R^{2'}$, $R^{1''}$, $R^{2''}$, $R^{1*}$ and $R^{2*}$ may be the same or different and are $C_1$-$C_{50}$alkyl, $C_1$-$C_{50}$haloalkyl, $C_7$-$C_{25}$arylalkyl.

4. The compound according to claim 1, wherein
$A^1$ and $A^2$ are independently of each other a group of Formula

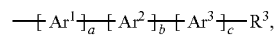

wherein
a is 1, b is 0, or 1, c is 0, or 1,
$Ar^2$ and $Ar^3$ are independently of each other a group of formula

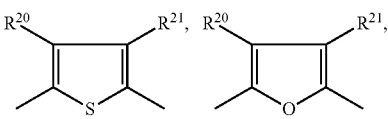

-continued

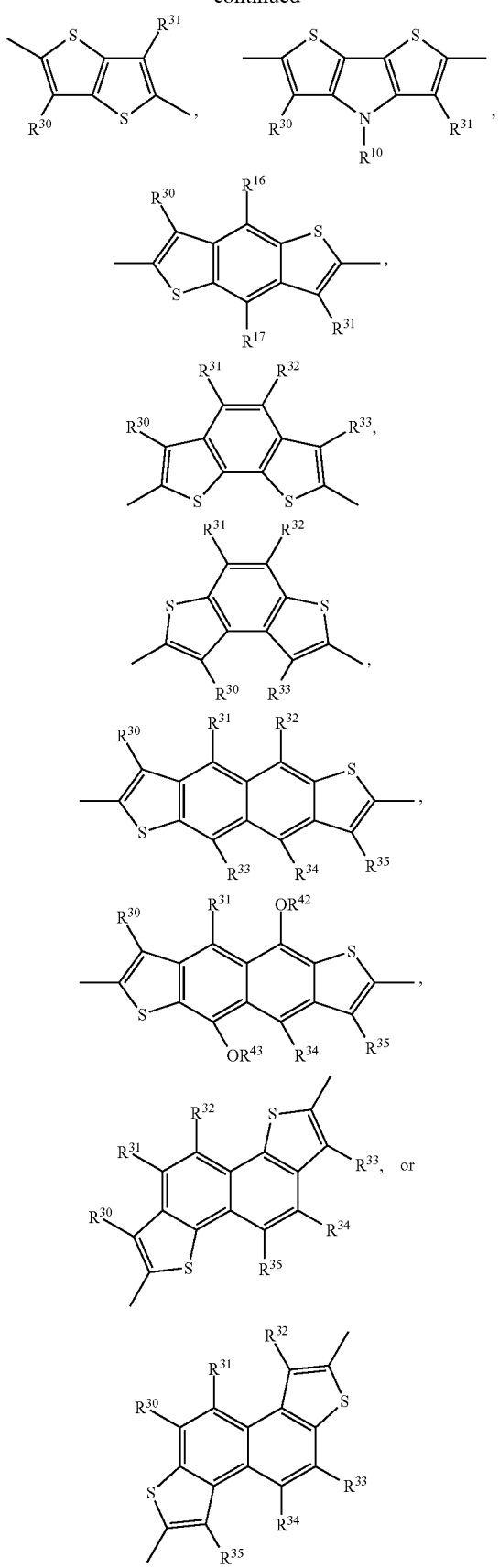

$R^{10}$ is a hydrogen, $C_1$-$C_{25}$alkyl or COO—$C_1$-$C_{25}$alkyl,
$R^{16}$ and $R^{17}$ are independently of each other hydrogen, halogen, $C_1$-$C_{25}$alkyl, $C_1$-$C_{25}$alkoxy, $C_7$-$C_{25}$arylalkyl, or

$R^x$ is a $C_1$-$C_{12}$alkyl group, or a tri ($C_1$-$C_8$alkyl)silyl group,
$R^{20}$ and $R^{21}$ are independently of each other hydrogen, or $C_1$-$C_{25}$alkyl,
$R^{30}$ to $R^{35}$ are independently of each other hydrogen, or $C_1$-$C_{25}$alkyl,
$R^{42}$ and $R^{43}$ are independently of each other $C_1$-$C_{25}$alkyl; and
$R^3$ is hydrogen.

5. The compound according to claim 4, wherein
$A^1$ and $A^2$ are independently of each other a group of formula

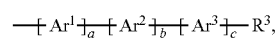

wherein
a is 1, b is 0, or 1, c is 0, or 1,
$Ar^2$ and $A^3$ are independently of each other

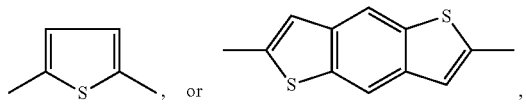

and $R^3$ is H.

6. The compound according to claim 1, wherein
$A^3$, $A^4$ and $A^5$ are independently of each other a group of formula

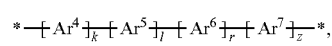

k is 0, 1, or 2; l is 1, 2, or 3; r is 0, or 1; z is 0, 1 or 2;
$Ar^4$, $Ar^5$, $Ar^6$ and $Ar^7$ are independently of each other a group of formula

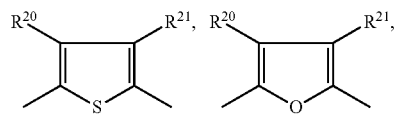

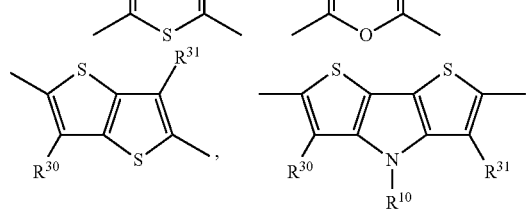

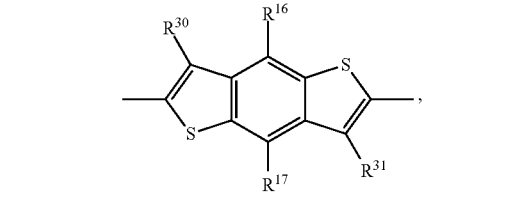

-continued

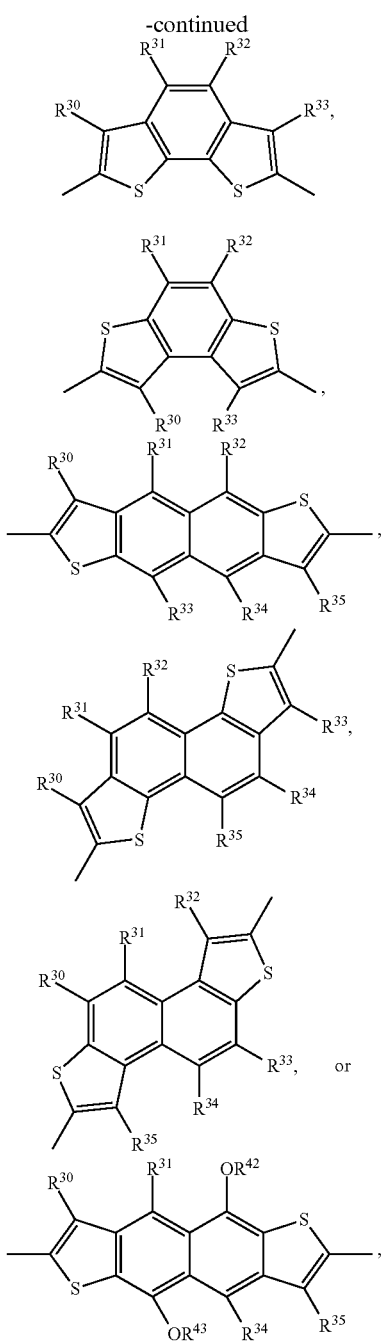

R¹⁰ is hydrogen, $C_1$-$C_{25}$alkyl or COO—$C_1$-$C_{25}$alkyl,
R¹⁶ and R¹⁷ are independently of each other hydrogen, halogen, $C_1$-$C_{25}$alkyl, $C_1$-$C_{25}$alkoxy, $C_7$-$C_{25}$arylalkyl, or ———≡—R^x, R^x is a $C_1$-$C_{25}$alkyl group, or a tri($C_1$-$C_8$alkyl)silyl group,
R²⁰ and R²¹ are independently of each other hydrogen, or $C_1$-$C_{25}$alkyl,
R³⁰ to R³⁵ are independently of each other hydrogen, or $C_1$-$C_{25}$alkyl, and
R⁴² and R⁴³ are independently of each other $C_1$-$C_{25}$alkyl.

7. The compound according to claim 5, wherein A³, A⁴ and A⁵ are independently of each other a group of formula

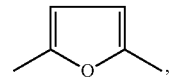

k and z are 0, or 1; l is 1, 2, or 3; r is 0;
Ar⁴ and Ar⁷ are a group of formula

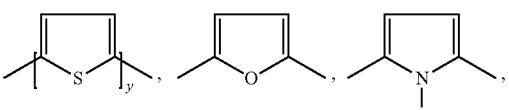

Ar⁵ is a group of formula

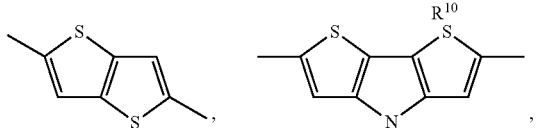

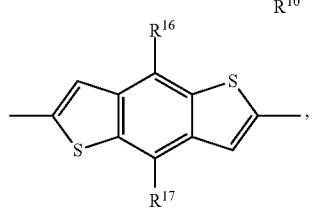

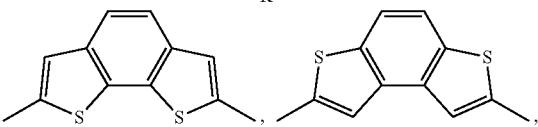

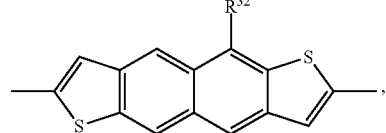

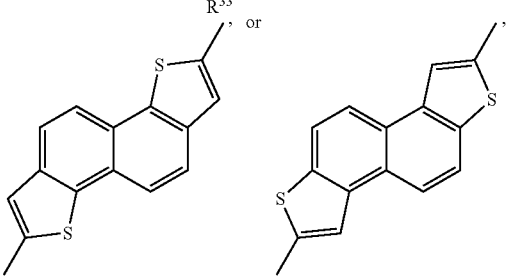

y is 1, 2 or 3,
R¹⁰ is H, or $C_1$-$C_{25}$ alkyl,
R¹⁶ and R¹⁷ are H, or $C_1$-$C_{25}$alkyl, and
R³² and R³³ are H, or $C_1$-$C_{25}$alkoxy.

8. The compound according to claim 1 of formula (IIa), (IIb), (IIc), (IIIa), (IIIb) or (IIIc),

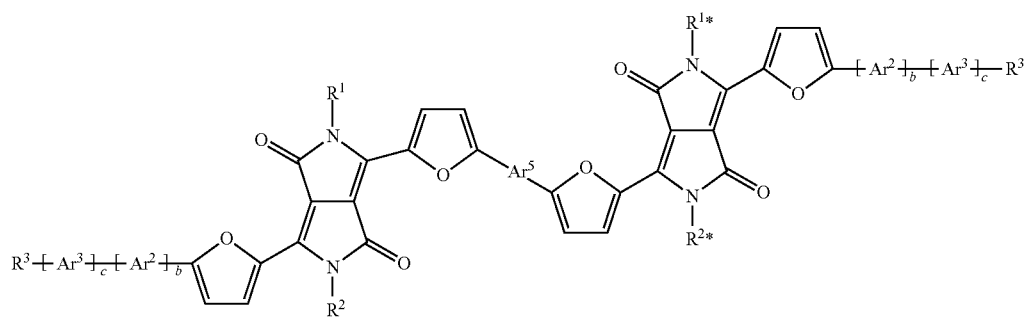
(IIa)
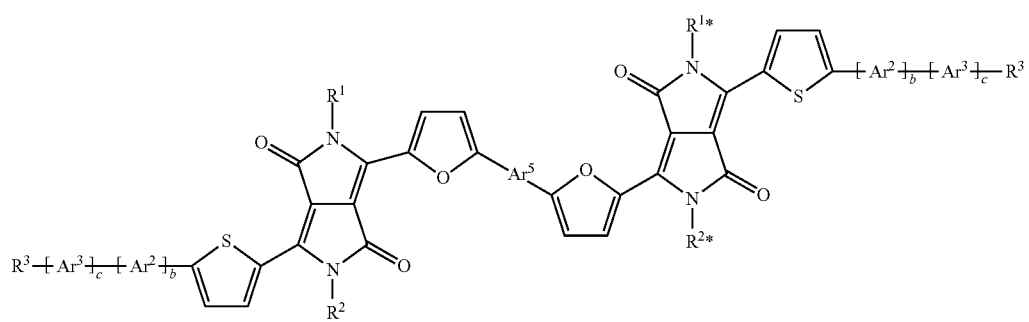
(IIb)
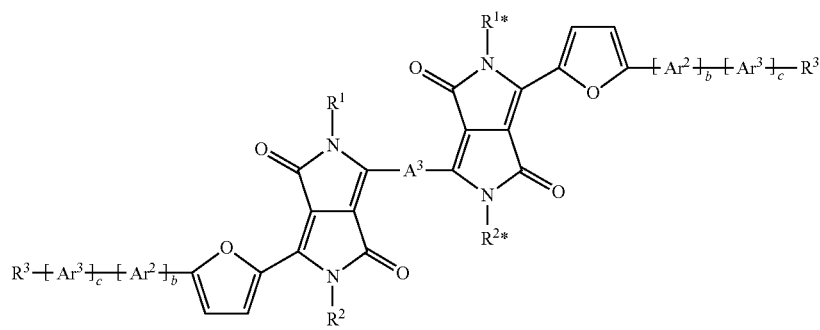
(IIc)
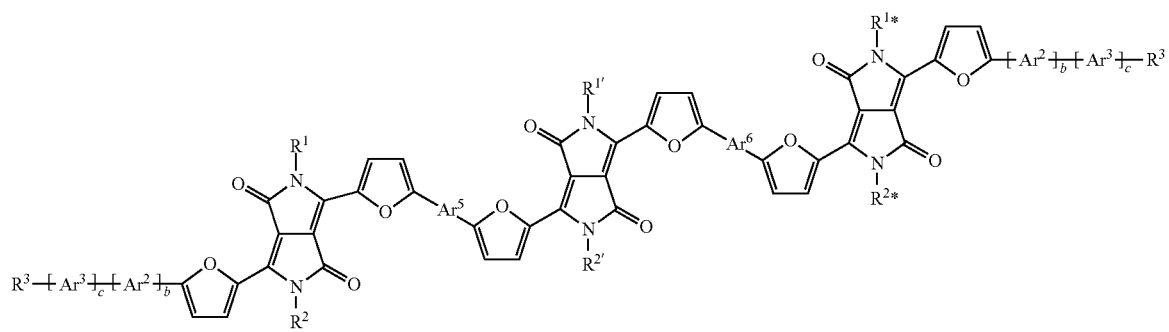
(IIIa)

-continued (IIIb)
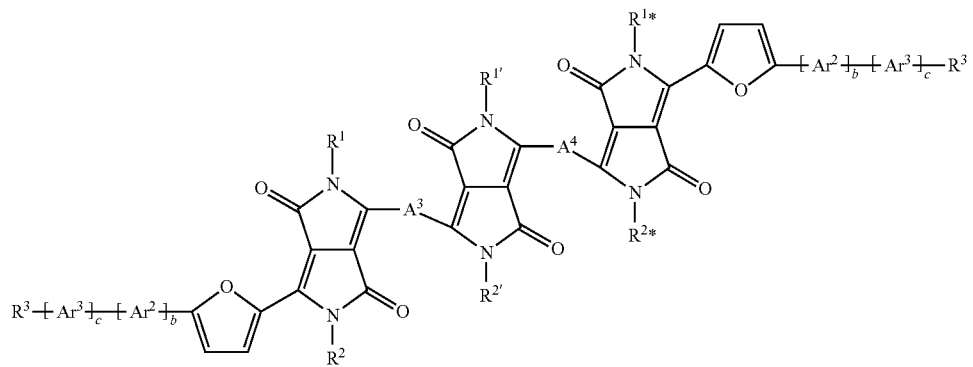

(IIIc)
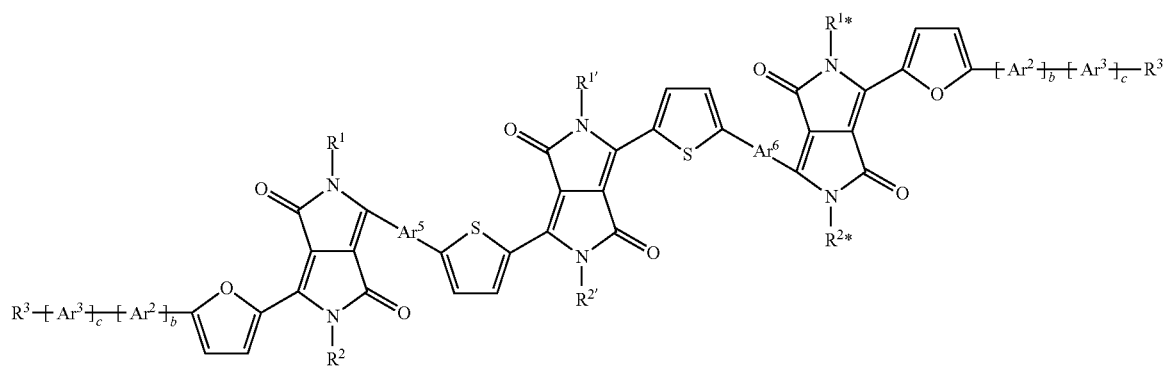

wherein
b is 0, or 1, c is 0, or 1,
$A^3$, $A^4$, $Ar^5$ and $Ar^6$ are independently of each other a group of formula

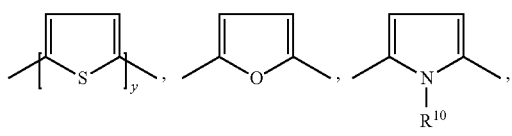

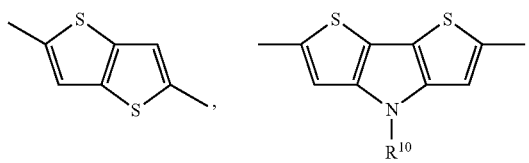

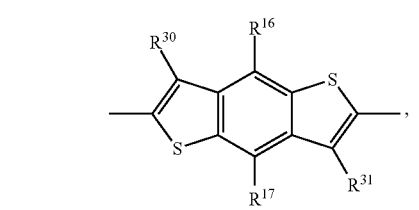

-continued
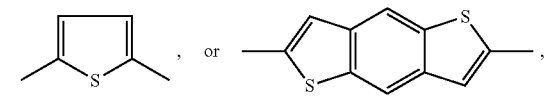

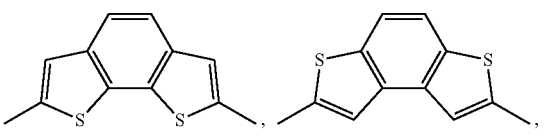

y is 1, 2, or 3,
$Ar^2$ and $Ar^3$ are independently of each other $R^1$, $R^2$, $R^{1'}$, $R^{2'}$, $R^{1*}$ and $R^{2*}$ are $C_1$-$C_{50}$alkyl, $C_1$-$C_{50}$haloalkyl, $C_7$-$C_{25}$arylalkyl
$R^3$ is H,
$R^{10}$ is H, or $C_1$-$C_{25}$alkyl,
$R^{16}$ and $R^{17}$ are H, or $C_1$-$C_{25}$alkyl, and
$R^{32}$ and $R^{33}$ are H, or $C_1$-$C_{25}$alkoxy.

9. A compound of formula (A-1)-(A22), (B-1) or (B-2)
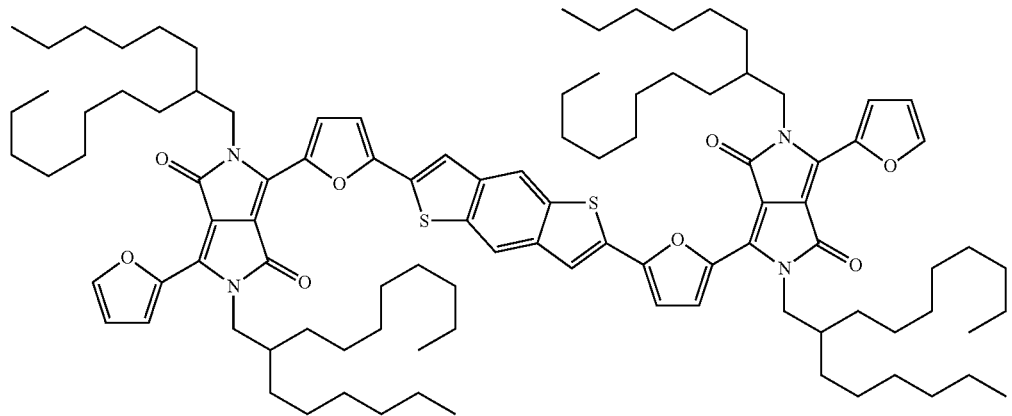
(A-1)
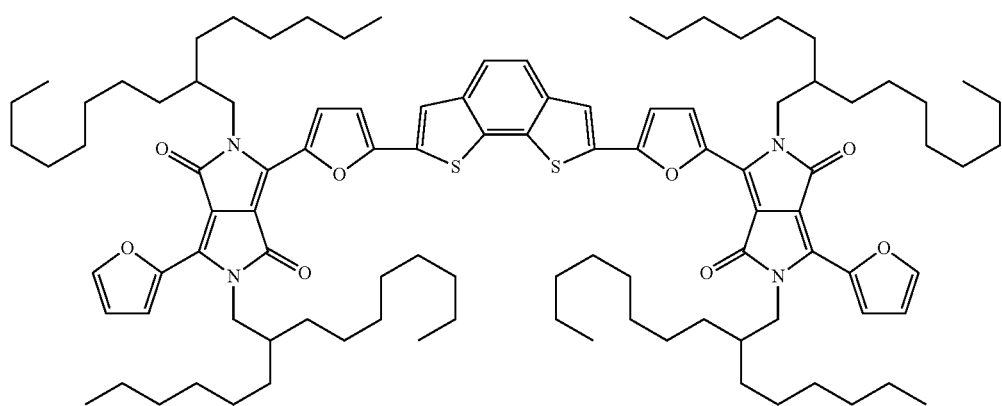
(A-2)
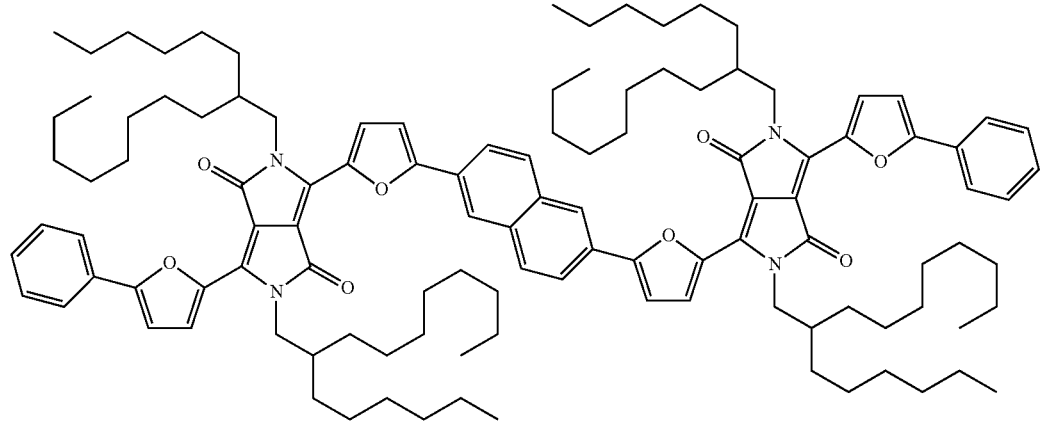
(A-3)

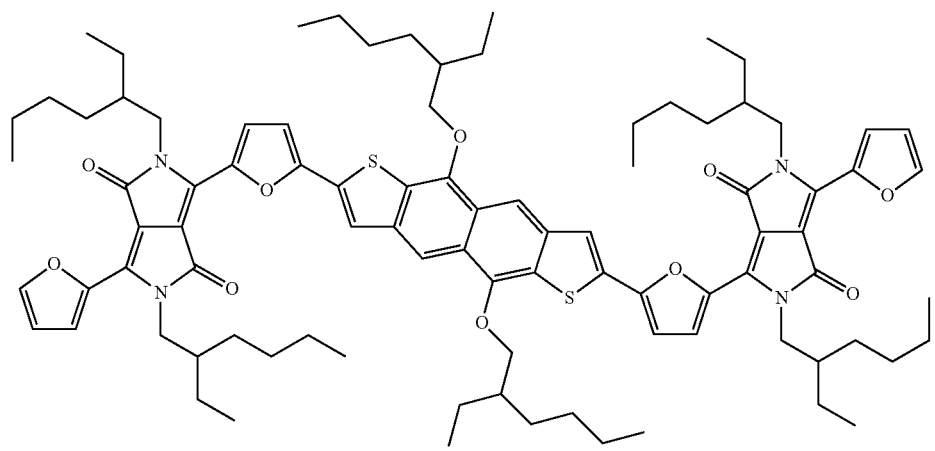
(A-4)
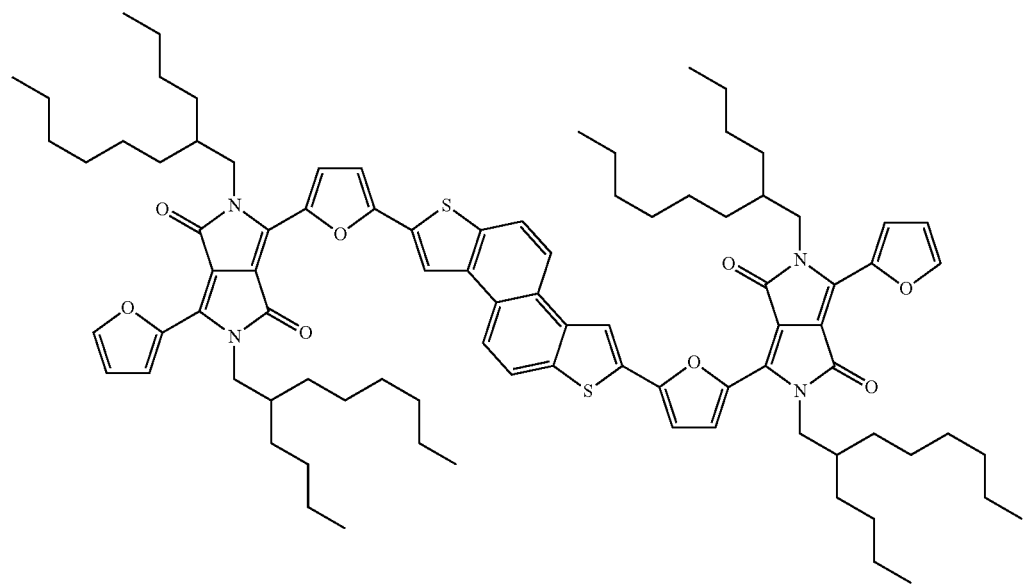
(A-5)
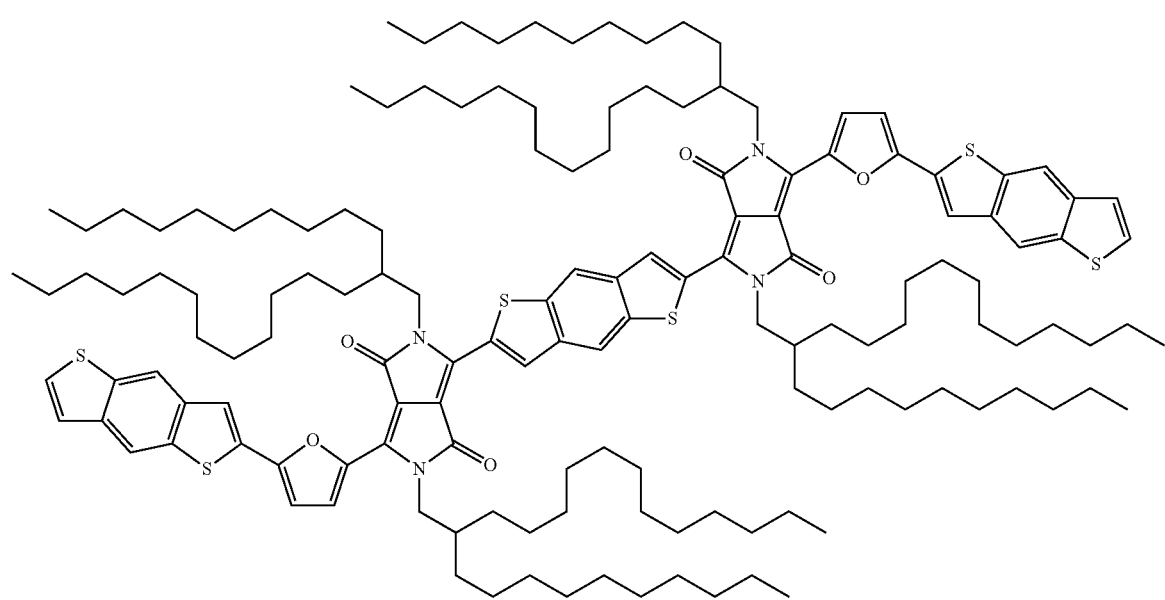
(A-6)

(A-7)
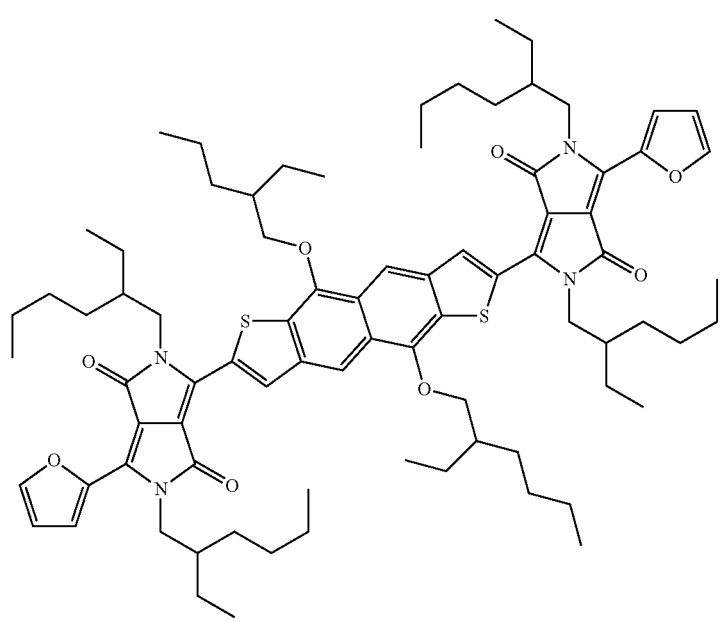
(A-8)
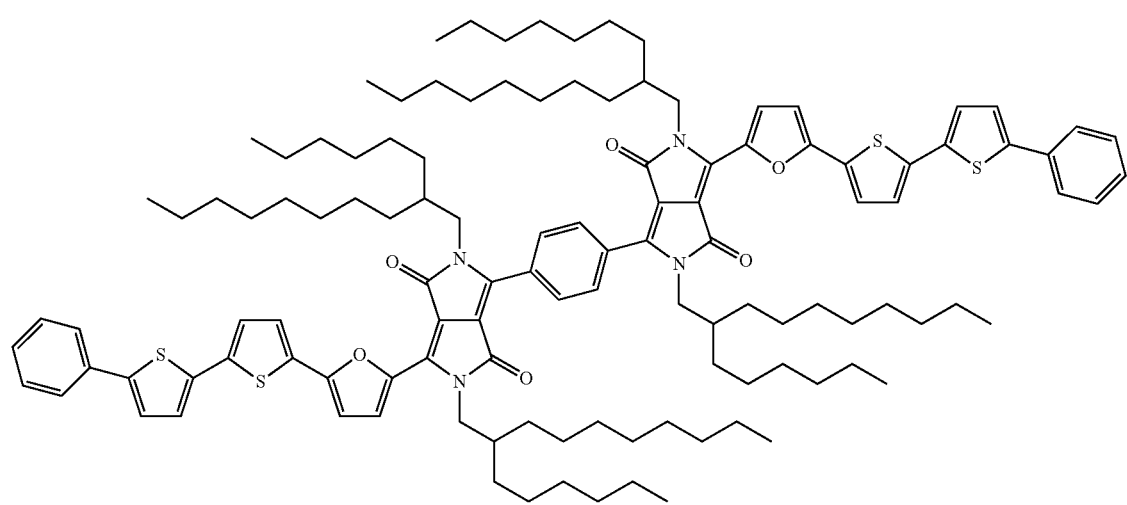

(A-9)
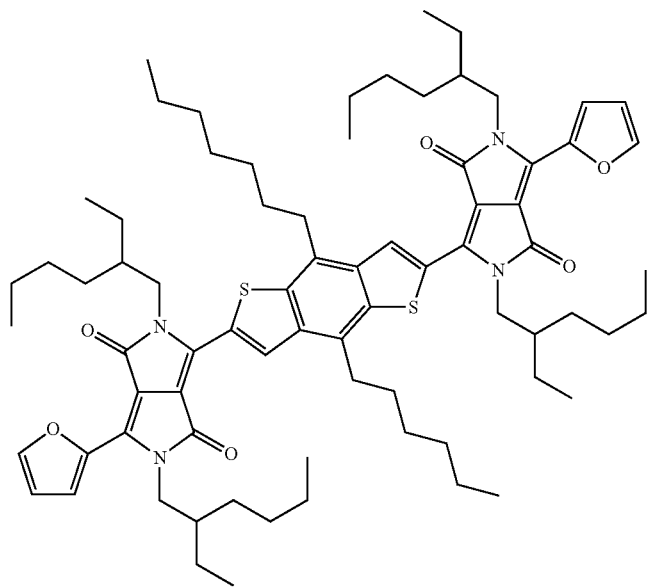
(A-10)
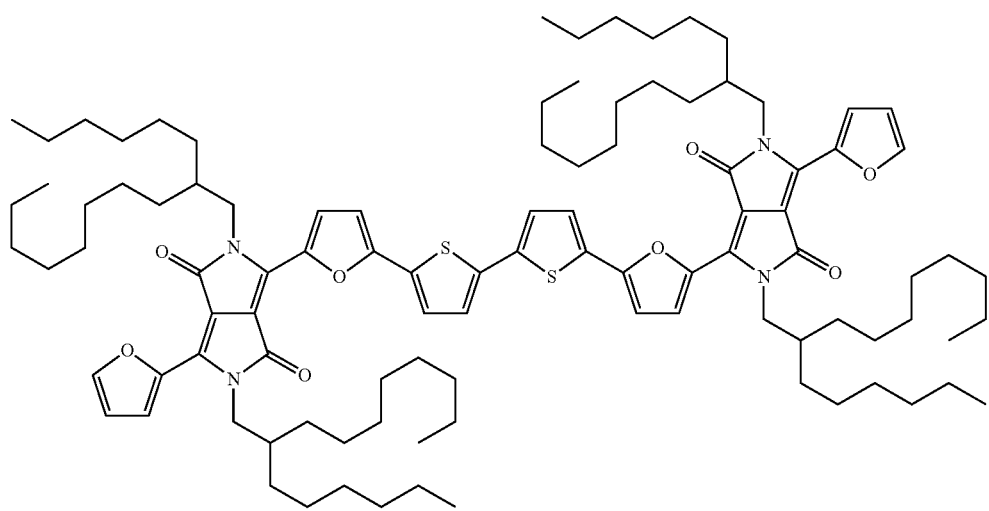
(A-11)
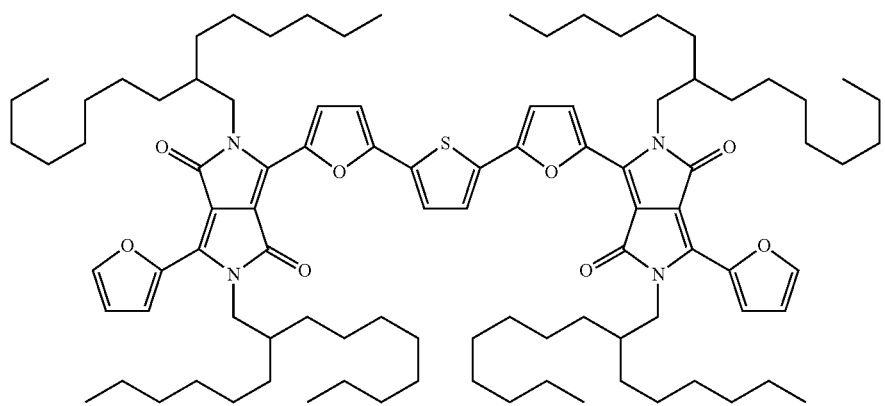

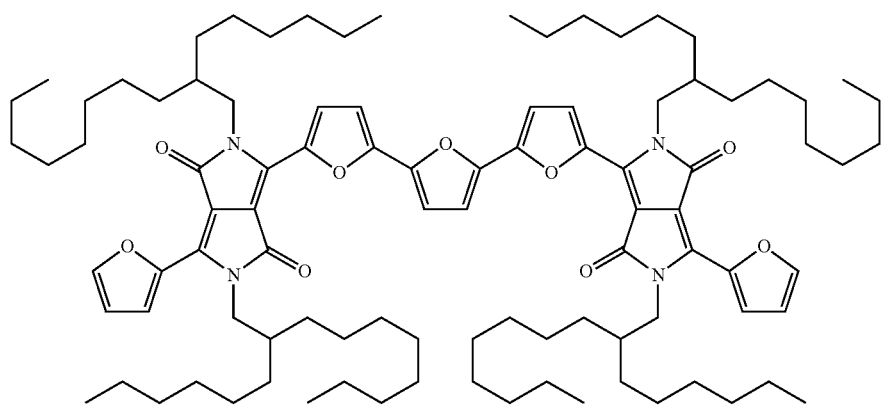
(A-12)
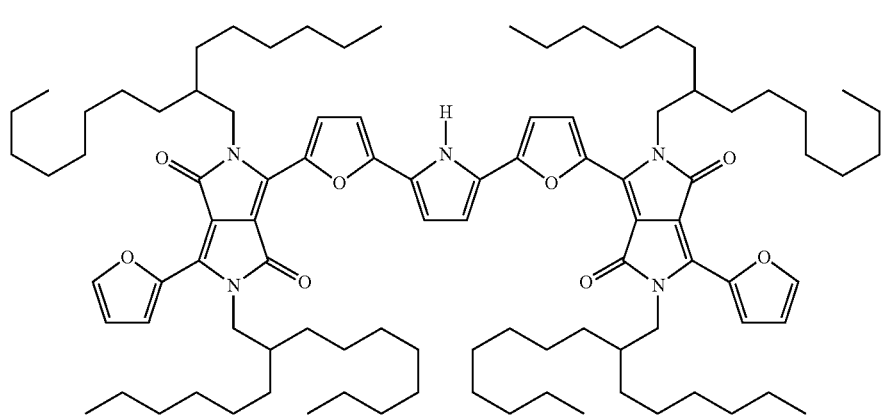
(A-13)
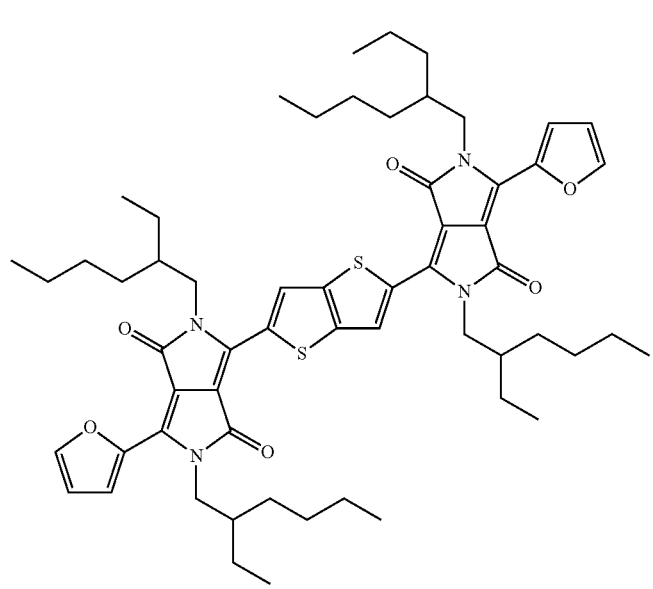
(A-14)

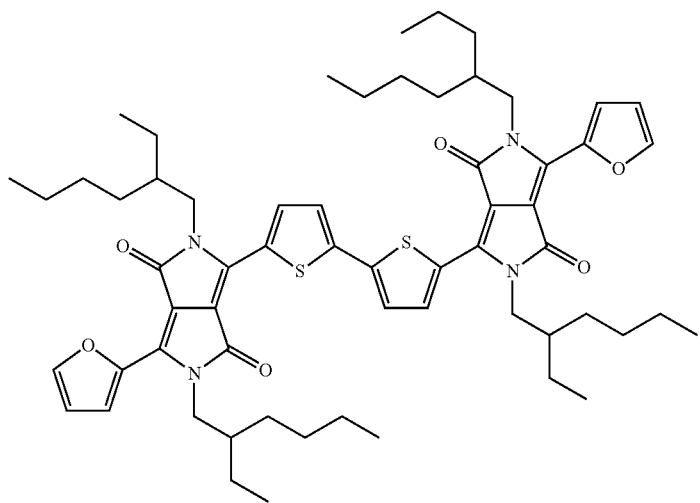
(A-15)
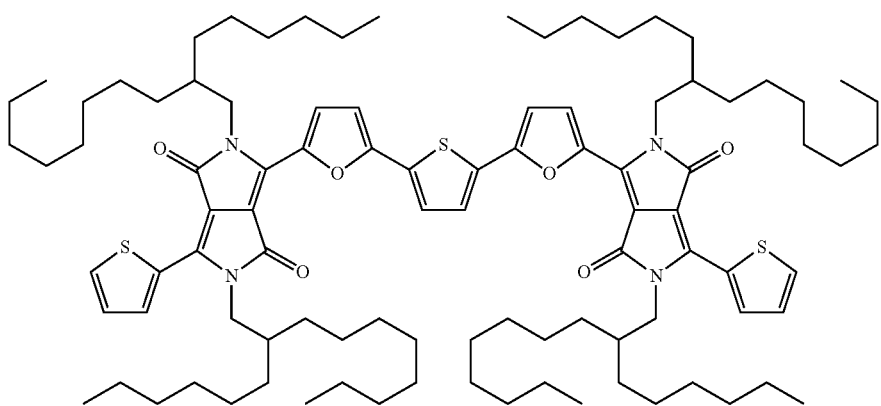
(A-16)
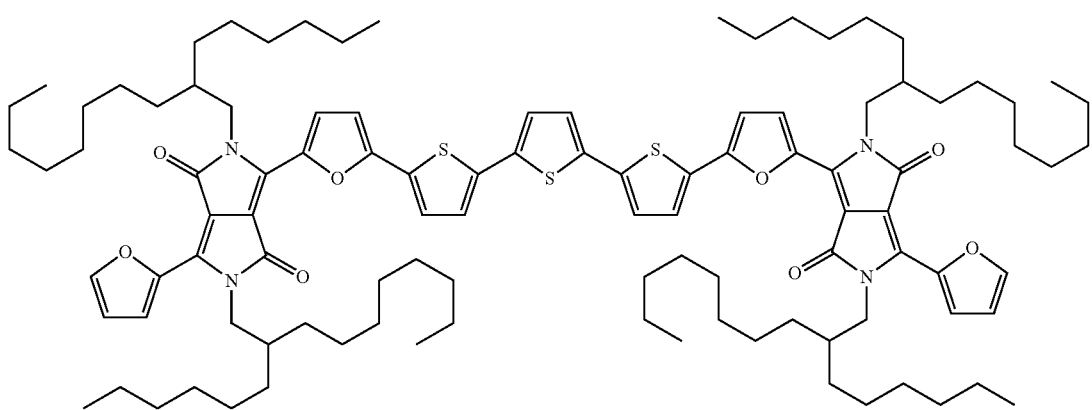
(A-17)

(A-18)
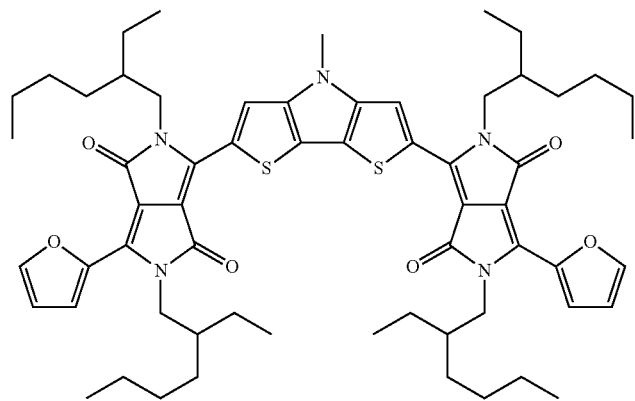
(A-19)
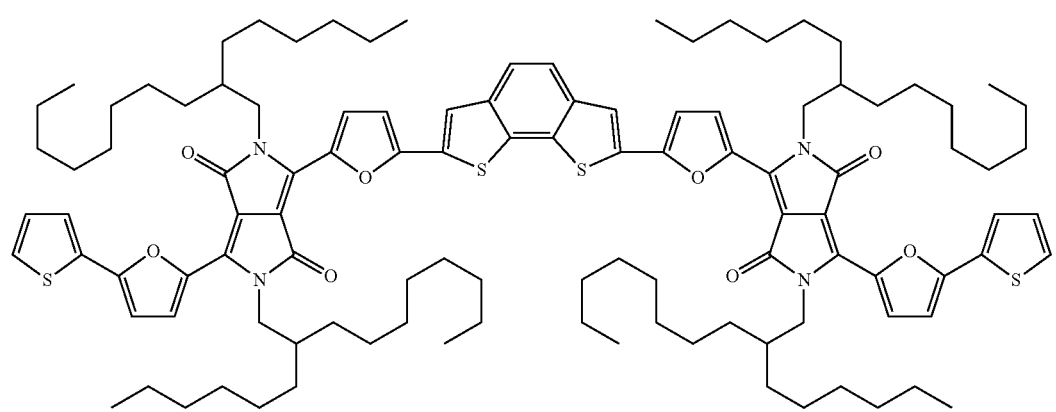
(A-20)
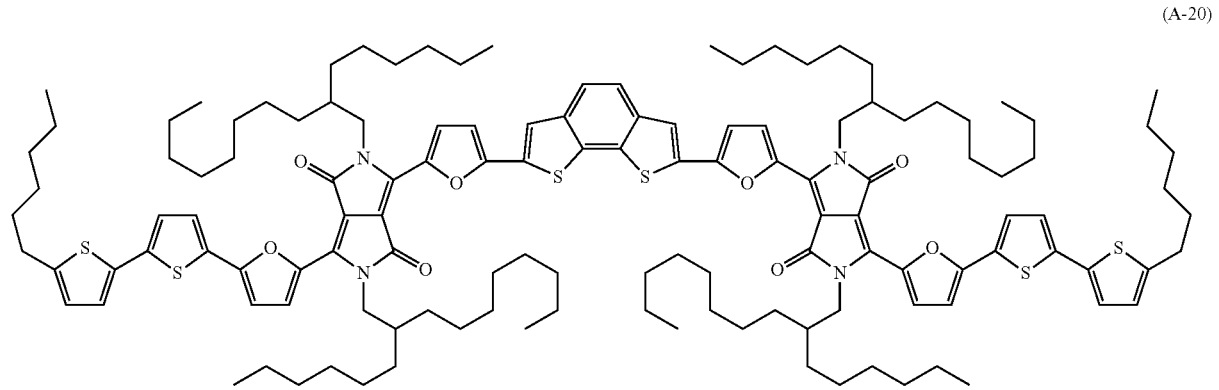

-continued
(A-21)
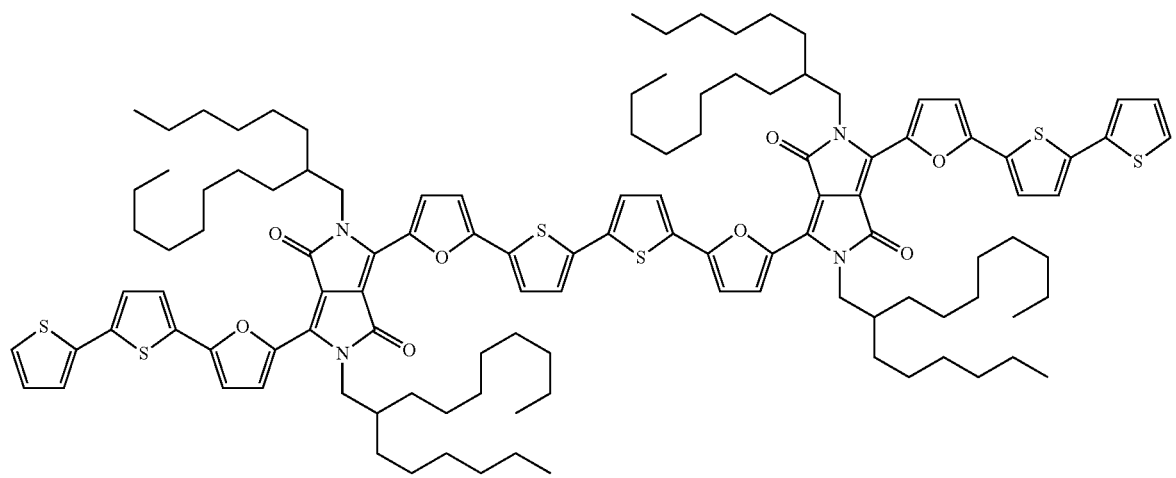
(A-22)
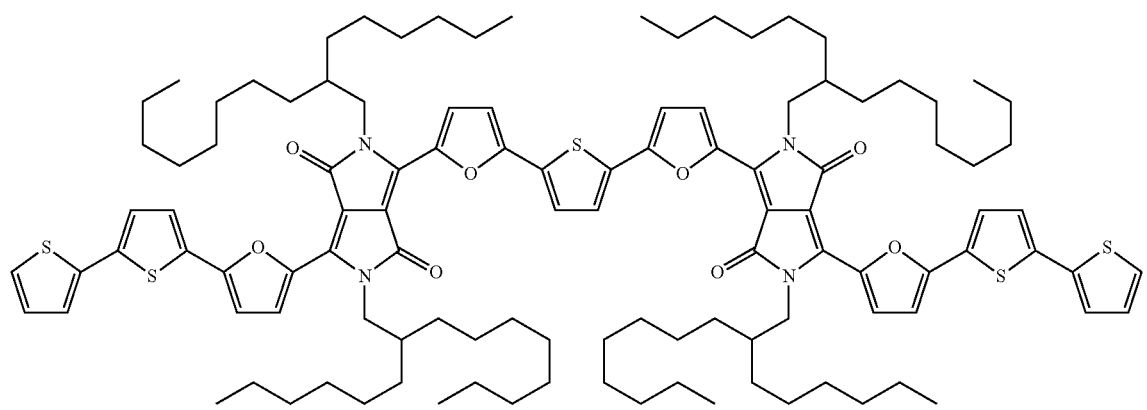
(B-1)
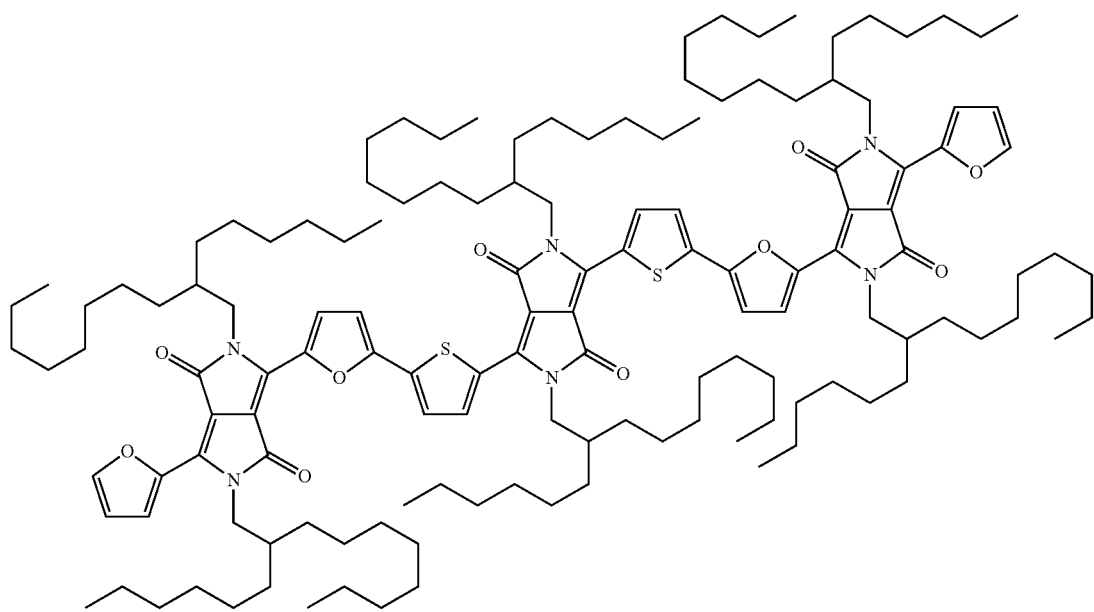

-continued (B-2)

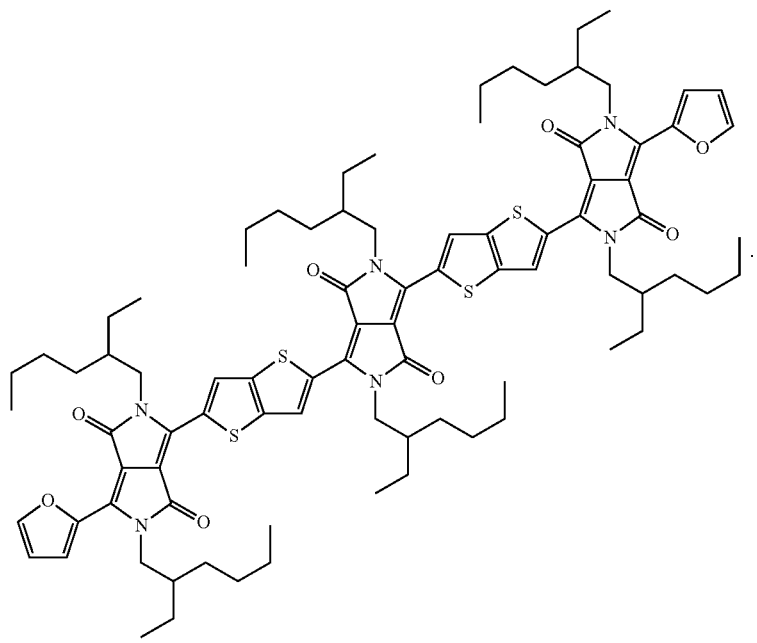

10. A semiconductor device comprising a compound of the formula I as defined in claim 1.

11. A semiconductor device according to claim 10 in the form of a diode, a photodiode, a sensor, an organic field effect transistor, a transistor for flexible displays, or a solar cell.

12. The compound according to claim 2 wherein $R^1$, $R^2$, $R^{1'}$, $R^{2'}$, $R^{1''}$, $R^{2''}$, $R^{1*}$ and $R^{2*}$ may be the same or different and are $C_1$-$C_{50}$alkyl, $C_1$-$C_{50}$haloalkyl, $C_7$-$C_{25}$arylalkyl.

13. The compound according to claim 2, wherein $A^1$ and $A^2$ are independently of each other a group of formula

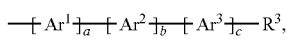

wherein a is 1, b is 0, or 1, c is 0, or 1, $Ar^2$ and $Ar^3$ are independently of each other a group of formula

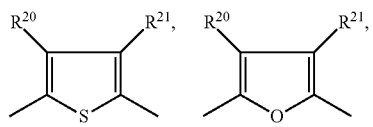

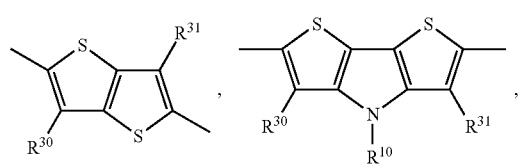

-continued

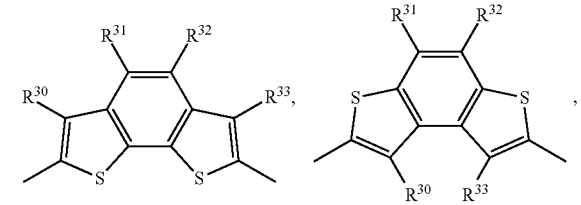

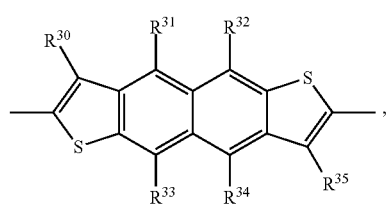

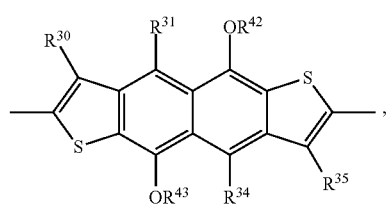

-continued

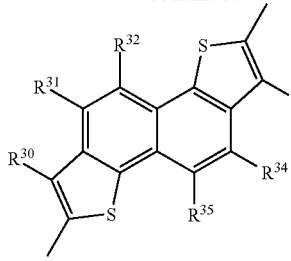
or

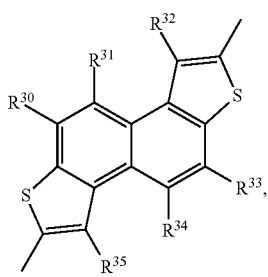

$R^{10}$ is hydrogen, $C_1$-$C_{25}$alkyl or COO—$C_1$-$C_{25}$alkyl, $R^{16}$ and $R^{17}$ are independently of each other hydrogen, halogen, $C_1$-$C_{25}$alkyl, $C_1$-$C_{25}$alkoxy, $C_7$-$C_{25}$arylalkyl, or

$R^x$ is a $C_1$-$C_{12}$alkyl group, or a tri($C_1$-$C_8$alkyl)silyl group, $R^{20}$ and $R^{21}$ are independently of each other hydrogen, or $C_1$-$C_{25}$alkyl, $R^{30}$ to $R^{35}$ are independently of each other hydrogen, or $C_1$-$C_{25}$alkyl, $R^{42}$ and $R^{43}$ are independently of each other $C_1$-$C_{25}$alkyl; and $R^3$ is hydrogen.

14. The compound according to claim 12, wherein $A^1$ and $A^2$ are independently of each other a group of formula

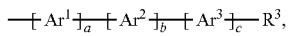

wherein a is 1, b is 0, or 1, c is 0, or 1, $Ar^2$ and $Ar^3$ are independently of each other a group of formula

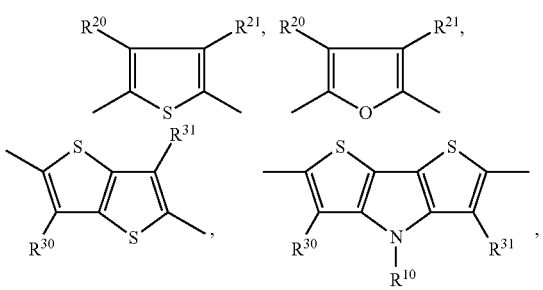

-continued

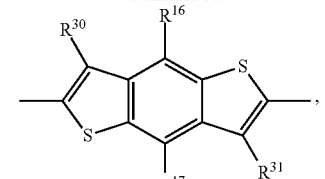

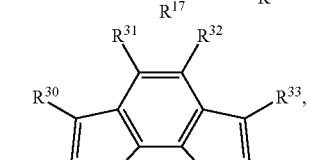

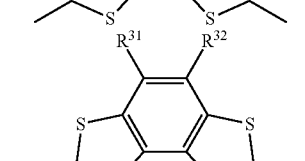

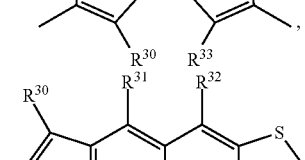

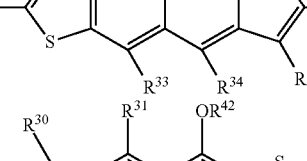

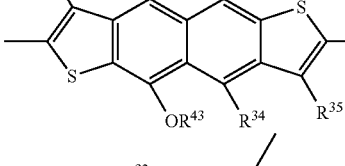

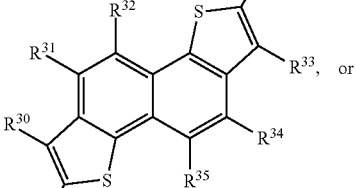

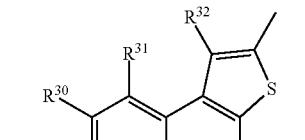

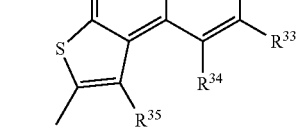

$R^{10}$ is hydrogen, $C_1$-$C_{25}$alkyl or COO—$C_1$-$C_{25}$alkyl, $R^{16}$ and $R^{17}$ are independently of each other hydrogen, halogen, $C_1$-$C_{25}$alkyl, $C_1$-$C_{25}$alkoxy, $C_7$-$C_{25}$arylalkyl, or

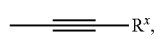

$R^x$ is a $C_1$-$C_{25}$alkyl group, or a tri($C_1$-$C_8$alkyl)silyl group,
$R^{20}$ and $R^{21}$ are independently of each other hydrogen, or $C_1$-$C_{25}$alkyl,
$R^{30}$ to $R^{35}$ are independently of each other hydrogen, or $C_1$-$C_{25}$alkyl,
$R^{42}$ and $R^{43}$ are independently of each other $C_1$-$C_{25}$alkyl; and
$R^3$ is hydrogen.

15. The compound according to claim 14, wherein $A^1$ and $A^2$ are independently of each other a group of formula

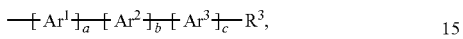

wherein
a is 1, b is 0, or 1, c is 0, or 1,
$Ar^2$ is,

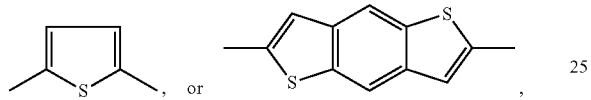

and $R^3$ is H.

16. The compound according to claim 15, wherein $A^3$, $A^4$ and $A^5$ are independently of each other a group of formula

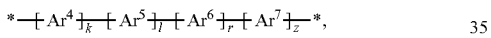

k is 0, 1, or 2; l is 1, 2, or 3; r is 0, or 1; z is 0, 1 or 2;
$Ar^4$, $Ar^5$, $Ar^6$ and $Ar^7$ are independently of each other a group of formula

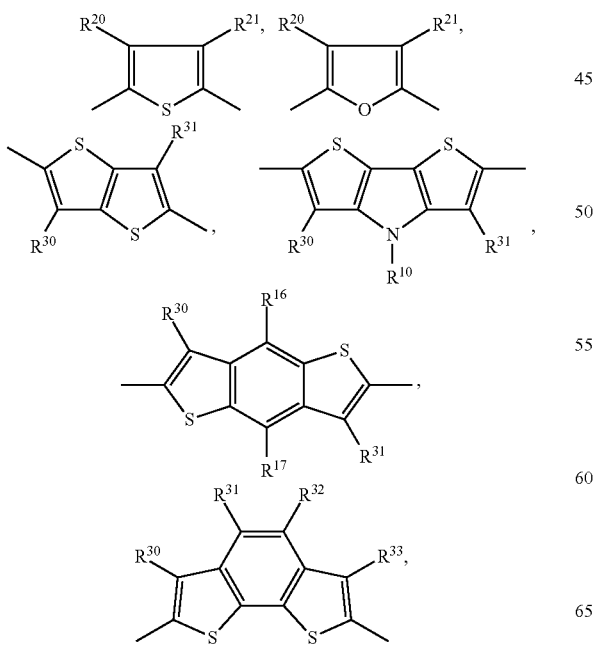

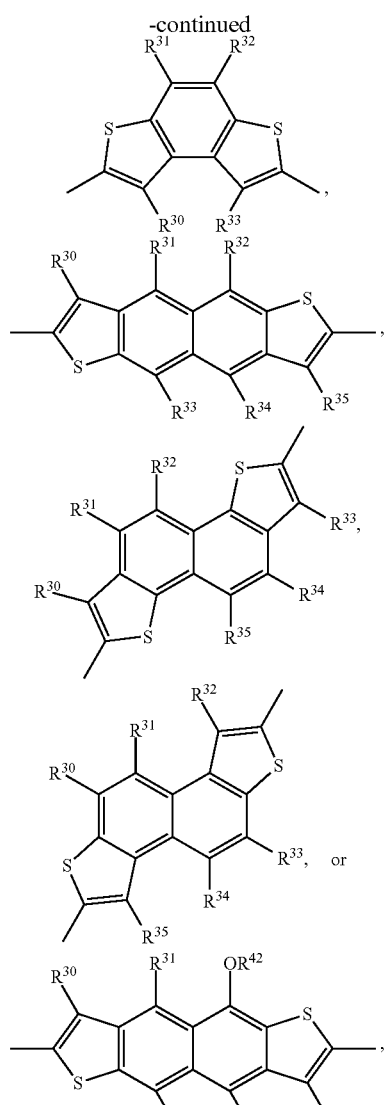

$R^{10}$ is hydrogen, $C_1$-$C_{25}$alkyl or COO—$C_1$-$C_{25}$alkyl,
$R^{16}$ and $R^{17}$ are independently of each other hydrogen, halogen, $C_1$-$C_{25}$alkyl, $C_1$-$C_{25}$alkoxy, $C_7$-$C_{25}$arylalkyl, or

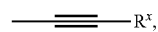

$R^x$ is a $C_1$-$C_{12}$alkyl group, or a tri($C_1$-$C_8$alkyl)silyl group,
$R^{20}$ and $R^{21}$ are independently of each other hydrogen, or $C_1$-$C_{25}$alkyl,
$R^{30}$ to $R^{35}$ are independently of each other hydrogen, or $C_1$-$C_{25}$alkyl, and
$R^{42}$ and $R^{43}$ are independently of each other $C_1$-$C_{25}$alkyl.

17. The compound according to claim 15, wherein $A^3$, $A^4$, and $A^5$ are independently of each other a group of formula

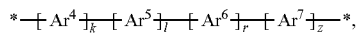

k and z are 0, or 1; l is 1, 2, or 3; r is 0;

Ar⁴ and Ar⁷ are a group of formula
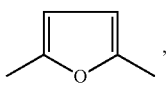
Ar⁵ is a group of formula
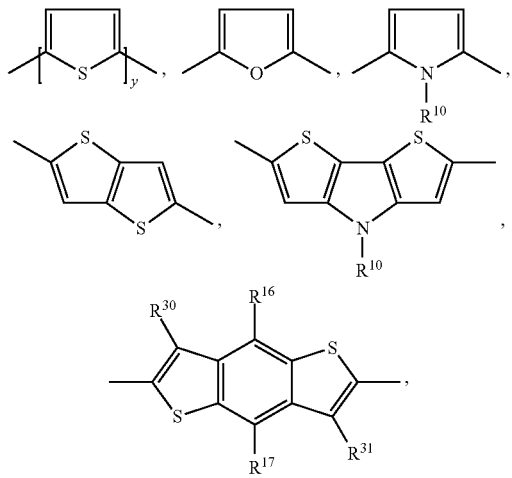
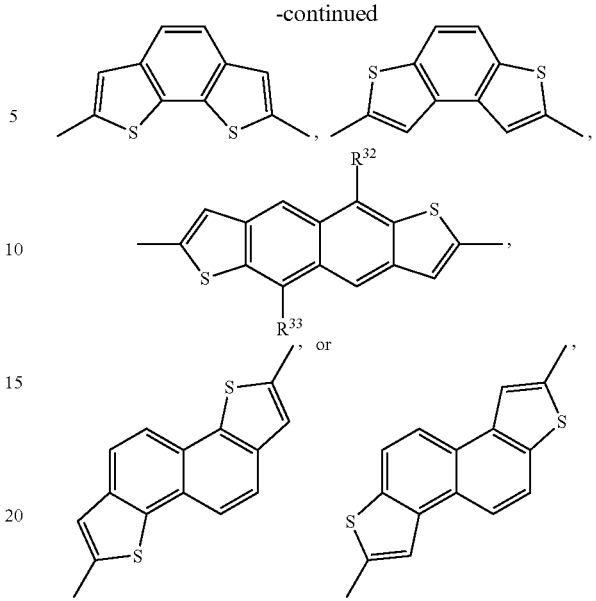
y is 1, 2, or 3,
R¹⁰ is H, or $C_1$-$C_{25}$alkyl,
R¹⁶ and R¹⁷ are H, or $C_1$-$C_{25}$alkyl, and
R³² and R³³ are H, or $C_1$-$C_{25}$alkoxy.
18. The compound according to claim 17 of formula (IIa), (IIb), (IIc), (IIIa), (IIIb) or (IIIc),
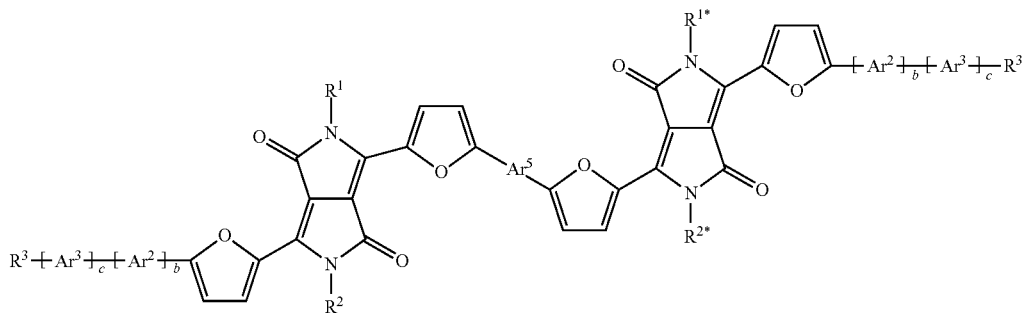
(IIa)
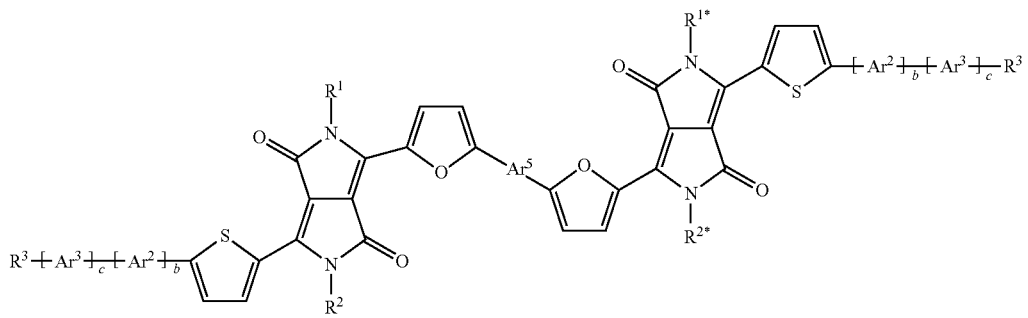
(IIb)

-continued
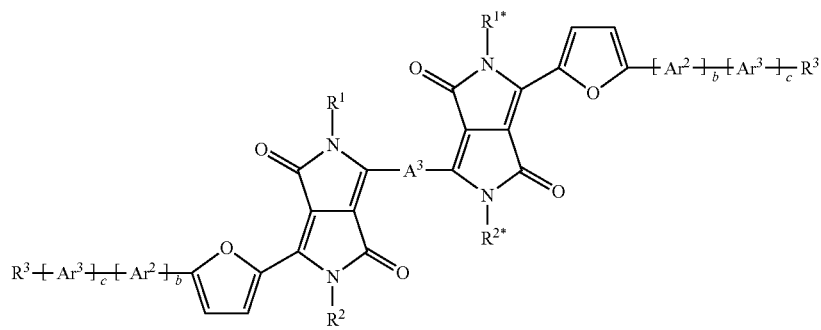
(IIc)
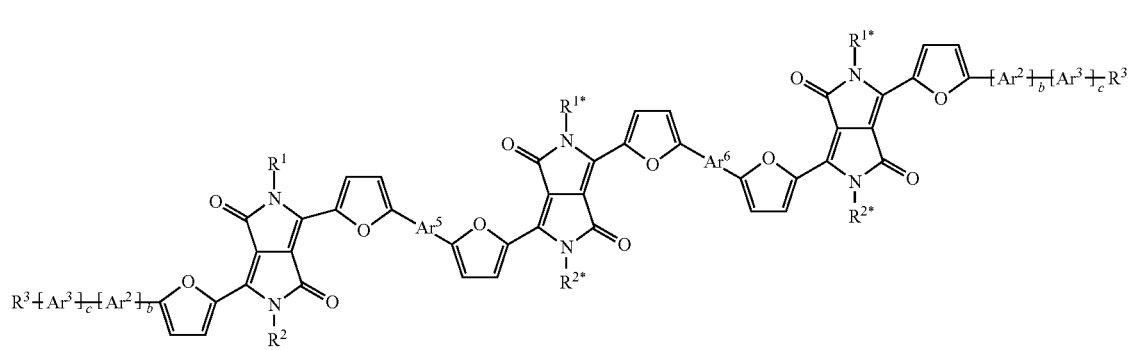
(IIIa)
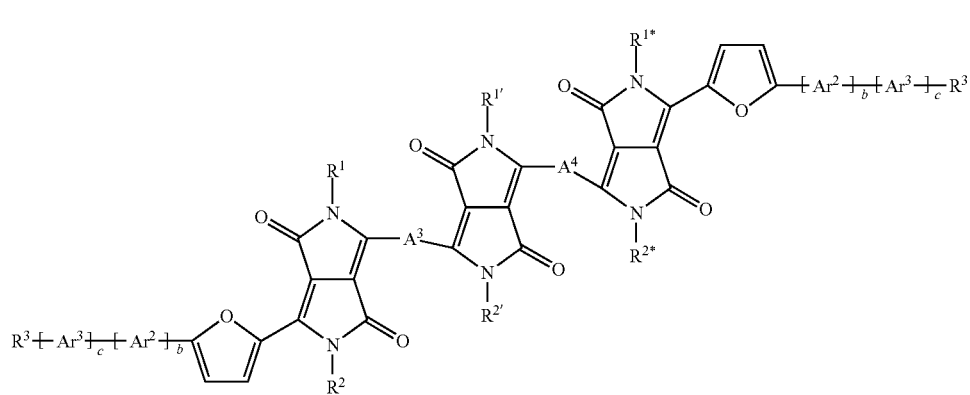
(IIIb)
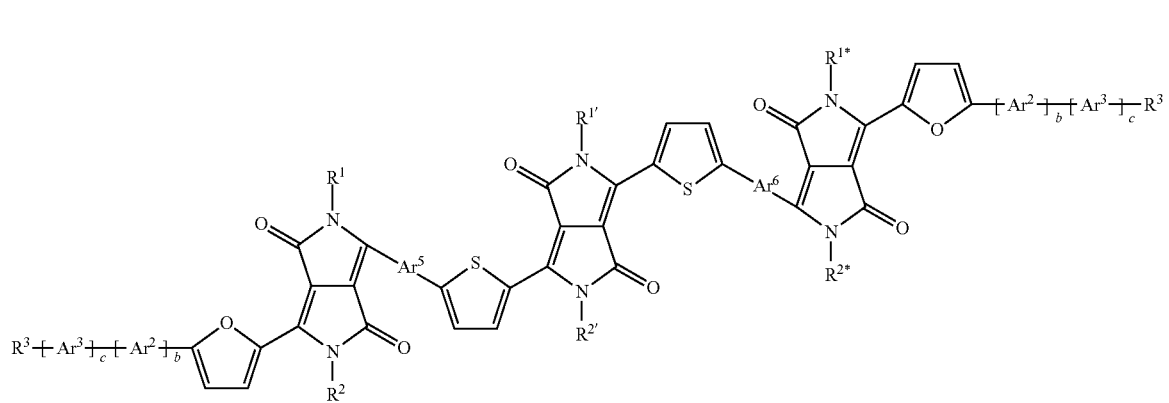
(IIIc)

wherein
b is 0, or 1, c is 0, or 1,
$A^3$, $A^4$, $Ar^5$ and $Ar^6$ are independently of each other a group of formula

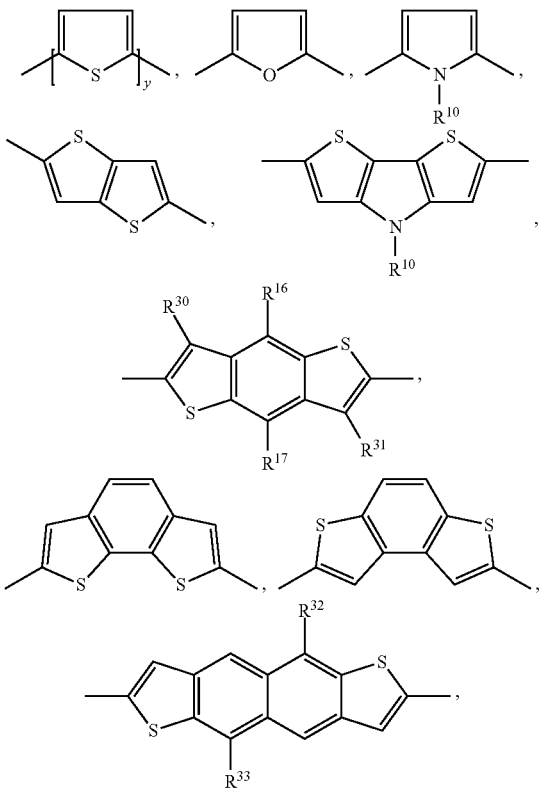

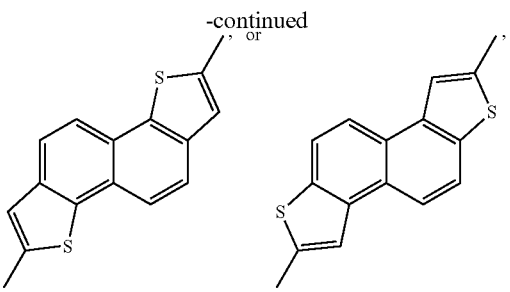

y is 1, 2, or 3,
$Ar^2$ and $Ar^3$ are independently of each other

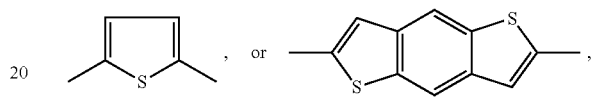

$R^1$, $R^2$, $R^{1'}$, $R^{2'}$, $R^{1''}$, $R^{2''}$, $R^{1*}$ and $R^{2*}$ are selected from hydrogen, $C_1$-$C_{50}$alkyl, $C_1$-$C_{50}$haloalkyl, $C_7$-$C_{25}$arylalkyl, $C_2$-$C_{50}$alkenyl, $C_2$-$C_{50}$haloalkenyl, allyl, $C_5$-$C_{12}$cycloalkyl, phenyl, or naphthyl which can optionally be substituted one or more times with $C_1$-$C_{12}$alkyl or $C_1$-$C_{12}$alkoxy, —O—$C_1$-$C_{18}$alkyl, —CO—$C_5$-$C_{12}$cycloalkyl and —COO—$C_1$-$C_{18}$alkyl, $R^3$ is H, $R^{10}$ is H, or $C_1$-$C_{25}$alkyl, $R^{16}$ and $R^{17}$ are H, or $C_1$-$C_{25}$alkyl, and $R^{32}$ and $R^{33}$ are H, or $C_1$-$C_{25}$alkoxy.

* * * * *